United States Patent
Aerssens et al.

(10) Patent No.: US 10,975,441 B2
(45) Date of Patent: Apr. 13, 2021

(54) R2R1/2 IN DIAGNOSIS AND THERAPY

(71) Applicants: Academisch Ziekenhuis Leiden A/U Leiden Uni Medical Ctr, Leiden (NL); Janssen Pharmaceutica NV, Beerse (BE)

(72) Inventors: Jeroen Marcel Maria Roger Aerssens, Nieuwrode (BE); Ronald Karel Louisa Van Brempt, RC Leiden (NL); Pieter Johan Peeters, Dessel (BE); Ronald Anthonius de Hoogt, Beerse (BE); Marcus Cornelis de Ruiter, RC Leiden (NL)

(73) Assignees: Academisch Ziekenhuis Leiden A/U Leiden Uni Medical Ctr, Leiden (NL); Janssen Pharmaceutica NV, Beerse (BE)

( * ) Notice: Subject to any disclaimer, the term of this patent is extended or adjusted under 35 U.S.C. 154(b) by 129 days.

(21) Appl. No.: 15/383,085

(22) Filed: Dec. 19, 2016

(65) Prior Publication Data
US 2017/0198357 A1    Jul. 13, 2017

Related U.S. Application Data

(63) Continuation of application No. 13/957,760, filed on Aug. 2, 2013, now abandoned, which is a continuation of application No. PCT/IB2012/000177, filed on Feb. 2, 2012.

(30) Foreign Application Priority Data

Feb. 3, 2011 (EP) ..................................... 1250127

(51) Int. Cl.
| | | |
|---|---|---|
| C12Q 1/00 | (2006.01) | |
| C12Q 1/6886 | (2018.01) | |
| A61K 48/00 | (2006.01) | |
| C12N 15/113 | (2010.01) | |
| C12Q 1/6883 | (2018.01) | |
| C07K 14/435 | (2006.01) | |
| A61K 38/17 | (2006.01) | |
| C12Q 1/6888 | (2018.01) | |
| G01N 33/68 | (2006.01) | |
| G01N 33/574 | (2006.01) | |

(52) U.S. Cl.
CPC ............ *C12Q 1/6886* (2013.01); *A61K 38/17* (2013.01); *A61K 48/005* (2013.01); *C07K 14/435* (2013.01); *C12N 15/113* (2013.01); *C12N 15/1136* (2013.01); *C12Q 1/6883* (2013.01); *C12Q 1/6888* (2013.01); *G01N 33/574* (2013.01); *G01N 33/6893* (2013.01); *C12N 2310/11* (2013.01); *C12N 2310/14* (2013.01); *C12Q 2600/158* (2013.01)

(58) Field of Classification Search
CPC .................................................... C12Q 1/6886
See application file for complete search history.

(56) References Cited

U.S. PATENT DOCUMENTS

| | | | | |
|---|---|---|---|---|
| 2007/0072175 A1* | 3/2007 | Cooper | ................ | C12Q 1/6876 435/5 |
| 2010/0291551 A1* | 11/2010 | Belouchi | .............. | C12Q 1/6883 435/6.11 |

FOREIGN PATENT DOCUMENTS

| | | |
|---|---|---|
| WO | WO 2008/067195 A2 | 6/2008 |
| WO | WO 2008/112177 A2 | 9/2008 |

OTHER PUBLICATIONS

GenBank:BC086894.1, Mus musculus cDNA clone Image:6765411, retrieved Nov. 19, 2014, 2 pages.
GenBank:BC147104.1, Mus musculus RIKEN cDNA 2200001115 gene, mRNA, retrieved Nov. 19, 2014, 2 pages.
GenBank: EDL24876.1, "Riken cDNA 2200001115, partial [Mus musculus]", retrieved Nov. 19, 2014, 2 pages.
RecName: Full=Protein FAM25. [Nov. 30, 2010, online] retrieved from NCBI accession No. Q8CF02: Protein, http://www.ncbi.nlm.nih.gov/protein/81900188?sat=14&satkey=508584, 2 pages.
RecName: Full=Protein FAM25. [Jan. 11, 2011, online] retrieved from NCBI Protein, accession No. Q5VTM1, http://www.ncbi.nlm.nih.gov/protein/122063472?sat=14&satkey=508859, 3 pages.

(Continued)

*Primary Examiner* — Valarie E Bertoglio
(74) *Attorney, Agent, or Firm* — Myers Bigel, P.A

(57) ABSTRACT

The present invention stems from the finding that two genes designated R2R[1] and R2R[2], play important roles in tissue development and cancer biology. In particular, the inventors have discovered that these two genes are expressed in pulmonary cells and are required for late branching morphogenesis of pulmonary epithelium and endothelium and support the development/maintenance of the refined three dimensional architecture of the lung. These genes are essential in the squamous differentiation program and development/maintenance of the progenitor (Krt14 expressing) cell pool. Moreover, the inventors have identified crucial roles for these genes in cancer biology, particularly processes associated with the acquisition of an immortal and metastatic phenotype (including cancer progression and metastasis) and pulmonary and cardiac development. Accordingly, the invention provides compounds and methods for use in the treatment of cardiac and pulmonary diseases and well as in cancer.

8 Claims, 43 Drawing Sheets
Specification includes a Sequence Listing.

(56) References Cited

OTHER PUBLICATIONS

RecName: Full=UPF0574 protein C9orf169 homolog. [Nov. 30, 2010, online] retrieved from NCBI Protein, accession No. Q9D1E4 http://www.ncbi.nlm.nih.gov/protein/81904729?sat=14&satkey=422307, 3 pages.
SubName: Full=Novel protein [Oct. 5, 2010, online] retrieved from UniProtKB/TrEMBL, accession No. B8A4K4 http://www.uniprot.org/uniprot/B8A4K4.txt?version=12, 2 pages.
International Search Report and Written Opinion, PCT/IB2012/000177, dated May 31, 2012.
Database Geneseq [Online]. Nov. 13, 2008. "Crohn's disease associated polypeptide SEQ ID No. 761", retrieved from EBI accession No. ATK90136. 2 pp.
Database Geneseq [Online]. Mar. 5, 2009. "Human schizophrenia related amino acid sequence SEQ ID:929", retrieved from EBI accession No. GSP:AUZ53610. 2 pp.
Database Geneseq [Online]. Jul. 10, 2008. "DNA fragments of a human Tox gene, 44680", retrieved from EBI accession No. GSN:ARC00629. 2 pp.
Database UniProt [Online]. Mar. 3, 2009. "SubName: Full=Novel protein", retrieved from EBI accession No. UNIPROT:B8A4K4. 1 p.
Lin S et al. Misexpression of MIA disrupts lung morphogenesis and causes neonatal death. Developmental Biology. 2008; 316: 441-455.
Ng Y-S et al. Differential expression of VEGF isoforms in mouse during development and in the adult. Developmental Dynamics. 2001; 220: 112-121.
Von Gise A and PU WT. Endocardial and epicardial epithelial to mesenchymal transitions in heart development and disease. Circ Res. 2012; 110: 1628-1645.
Kovacic JC et al. Epithelial-to-mesenchymal and endothelial-to-mesenchymal transition from cardiovascular development to disease. Circulation. 2012; 125: 1795-1808.
Thiery JP et al. Epithelial-mesenchymal transitions in development and disease. Cell. Nov. 25, 2009; 139: 871-890.
Zeisberg EM et al. Endothelial-to-mesenchymal transition contributes to cardiac fibrosis, Nature Medicine. Aug. 2007; 13(8): 952-961.
Soofiyani SR et al. Gene therapy, early promises, subsequent problems, and recent breakthroughs. Advanced Pharmaceutical Bulletin, 2013: 3(2); 249-255.
Extended European Search Report corresponding to 19165320.3, dated Oct. 4, 2019 (12 pp).
Database Geneseq (Online) Apr. 3, 2008 'Human protein AQUA peptide SEQ ID No. 332.' retrieved from EBI accession No. GSP: ADQ66790.
Database GenBank (Online) Jan. 28, 2009, 'Novel nucleic acids' XP002655015, Database accession No. DL491673.
Database Geneseq (Online) Jun. 28, 2007 'Biomarker salivary peptide, SEQ ID: 5.' XP002655016, retrieved from EBI acccession No. GSP: AFU70535. Database accession No. AFU70535.
GenBank [online] Accession No. BC018787, Mar. 4, 2003 uploaded [retrieved on Jun. 26, 2020] Definition: *Homo sapiens,* clone Image: 4876018, mRNA.
GenBank [online] Accession No. NM_026415, Dec. 29, 2010 uploaded, [retrieved on Jun. 26, 2020]. Definition: Mus musculus RIKEN cDNA 2310002J15 gene (2310002J15Rik), mRNA.
GenBank [online] Accession No. NM_183278.Dec. 29, 2010 uploaded, [retrieved on Jun. 26, 2020] Definition: Mus musculus RIKEN cDNA 2200001115 gene (2200001I15Rik).
GenBank [online]. Accession No. NM_001146157, Dec. 27, 2010 uploaded [retrieved on Jun. 26, 2020] Definition: Homo sapiens family with sequence similarity25, member A (FAM25A), mRNA.
Japanese Office Action corresponding to JP 2019-101144; dated Jul. 6, 2020 (7 pages, including English translation).
WDB Co., Ltd. [online], Research Glossary RT-PCR Method, Internet Archive: Wayba ck Machine, Published: Jun. 27, 2010, [Search Date: Jun. 26, 2020], <https: // web .archive.org/web/20100627015423/http://www.kenq.net/dic/34.html>.
Eguchi et al. "[Title Unknown]" Pharmacia, 44(3): 203-207 (2008) (19 pages including English translation).
Japanese Office Action corresponding to JP 2017-38119; dated Jun. 8, 2020 (46 pages, including English translation).

* cited by examiner

```
                            (1)   1          10          20          30         41
     hR4RA__ENST00000343959  (1)   -----------------------------------------
         R4Ra_pDONR201       (1)   ACACTGACACGGACCGAAGGAGTGGAAAAAGCTTTACCTGT
              Consensus      (1)
                                                                        Section 2
                           (42)  42          50          60          70         82
     hR4RA__ENST00000343959  (1)  -ACTGTCTGCTGCCACACGATGCTGGGAGGCCTGGGGAAGC
         R4Ra_pDONR201      (42)  CACTGTCTGCTGCCATACGATGCTGGGAGGCCTGGGGAAGC
              Consensus     (42)   ACTGTCTGCTGCCA ACGATGCTGGGAGGCCTGGGGAAGC
                                                                        Section 3
                           (83)  83          90         100         110        123
     hR4RA__ENST00000343959 (41)  TGGCTGCCGAAGGCCTGGCCCACCGCACCGAGAAGGCCACC
         R4Ra_pDONR201      (83)  TGGCGGCCGAGGGCCTGGCCCACCGCACAGAGAAAGCCACT
              Consensus     (83)  TGGC GCCGA GGCCTGGCCCACCGCAC GAGAA GCCAC
                                                                        Section 4
                          (124) 124         130         140         150        164
     hR4RA__ENST00000343959 (82)  GAGGGAGCCATTCATGCCGTGGAAGAAGTGGTGAAGGAGGT
         R4Ra_pDONR201     (124)  GGGGGAGCAGTTCACGCAGTGGAAGAGGTGGTGAGCGAGGT
              Consensus    (124)  G GGGAGC  TTCA GC GTGGAAGA GTGGTGA  GAGGT
                                                                        Section 5
                          (165) 165         170         180         190        205
     hR4RA__ENST00000343959 (123) GGTGGGACACGCCAAGGAGACTGGAGAGAAAGCCATTGCTG
         R4Ra_pDONR201     (165) GGTGGGCCACGCCAAGGAGGTTGGAGAGAAGACCATTAATG
              Consensus    (165) GGTGGG CACGCCAAGGAG  TGGAGAGAA  CCATT  TG
                                                                        Section 6
                          (206) 206         220         230            246
     hR4RA__ENST00000343959 (164) AAGCCATAAAGAAAGCCCAAGAGTCAGGGGACAAAAAGATG
         R4Ra_pDONR201     (206) ACGCCCTAAAGAAAGCCCAAGAATCAGGAGACAGGGTGGTG
              Consensus    (206) A GCC TAAAGAAAGCCCAAGA TCAGG GACA    G TG
                                                                        Section 7
                          (247) 247         260         270            287
     hR4RA__ENST00000343959 (205) AAGGAAATCACTGAGACAGTGACCAACACAGTCACAAATGC
         R4Ra_pDONR201     (247) AAGGAGGTCACTGAGAAGGTCACCCACACCATCACTGATGC
              Consensus    (247) AAGGA  TCACTGAGA  GT ACC ACAC  TCAC  ATGC
                                                                        Section 8
                          (288) 288         300         310            328
     hR4RA__ENST00000343959 (246) CATCACCCATGCAGCAGAGAGTCTGGACAAACTTGGACAGT
         R4Ra_pDONR201     (288) TGTTACCCATGCGGCAGAAGGCCTGGAAGACTGGGACAGT
              Consensus    (288)   T ACCCATGC GCAGA  G CTGG  A ACT GGACAGT
                                                                        Section 9
                          (329) 329         340         350            369
     hR4RA__ENST00000343959 (287) GAGTGCACCTGCTACCACGGC----CCTTCCCCAGTCTCAA
         R4Ra_pDONR201     (329) GAGCCTGCCTACCAGCATGGCTGGCCCTTCCTGAAGGTCAA
              Consensus    (329) GAG   CCT C A CA GGC     CCTTCC  A  TCAA
```

FIG. 8

```
                                                                       Section 1
                            (1)   1          10          20          34
Translation of hR4RA__ENST00000343959 (1)  MLGGLGKLAAEGLAHRTEKATEGAIHAVEEVVKE
Translation of R4Ra_pDONR201          (1)  MLGGLGKLAAEGLAHRTEKATGGAVHAVEEVVSE
                        Consensus     (1)  MLGGLGKLAAEGLAHRTEKAT GA HAVEEVV E
                                                                       Section 2
                           (35)  35         40          50              68
Translation of hR4RA__ENST00000343959 (35) VVGHAKETGEKAIAEAIKKAQESGDRKMKEITET
Translation of R4Ra_pDONR201         (35) VVGHAKEVGEKTINDALKKAQESGDRVVKEVTEK
                        Consensus    (35) VVGHAKE GEK I DA KKAQESGDR MKEITE
                                                                       Section 3
                           (69)  69         80          90
Translation of hR4RA__ENST00000343959 (69) VTNTVTNAITHAAESLDKLGQ-
Translation of R4Ra_pDONR201         (69) VTHTITDAVTHAAEGLGRLGQ-
                        Consensus    (69) VT TIT  AITHAAE L KLGQ
```

FIG. 9

```
                                              ─────────────────── Section 10
                           (370) 370       380       390       400       410
     hR4Rd_ENST00000359069 (370) CCCTCAGAGCCCAGGCCTGGGCTGCCACCCACCTGAGGACG
   R4Rd_2310002J15Rikcontig   (1) ----------------------------------------
                 Consensus (370)
                                              ─────────────────── Section 11
                           (411) 411       420       430       440       451
     hR4Rd_ENST00000359069 (411) AGGGCTGGGCCAGCTGTCGTGCTCCAGTTGCTGGGGCCTCT
   R4Rd_2310002J15Rikcontig   (1) -----GTGACTGGCTGCTGT-CTCTAGTTGTTGAGGCCTCT
                 Consensus (411)      G C   GCTG   GT CTC AGTTG TG GGCCTCT
                                              ─────────────────── Section 12
                           (452) 452      460       470       480       492
     hR4Rd_ENST00000359069 (452) TGGGATCTTGGG---AACCCCAT-CTCT-GAGCCCC-----
   R4Rd_2310002J15Rikcontig  (36) TGGGATCTYGGCGCTMACMCCWTGCTYTAGWGACTCCGATA
                 Consensus (452) TGGGATCT GG     AC CC T CT  T  G G C  C
                                              ─────────────────── Section 13
                           (493) 493       500       510       520       533
     hR4Rd_ENST00000359069 (483) --------GCCCCA-TGGCCCCGCCCCTCCCAAGGAGGGA
   R4Rd_2310002J15Rikcontig  (77) GCTCCCRMGGCTCCAGTGSASMCCTCGGKCGGNGGNAGGGA
                 Consensus (493)         GC CCA TG    C    C    C   G AGGGA
                                              ─────────────────── Section 14
                           (534) 534       540       550       560       574
     hR4Rd_ENST00000359069 (514) AAAGGCGGCTGCCAGTCGCTCAACTCAG--GCACTGGGACC
   R4Rd_2310002J15Rikcontig (118) AAAGGCACTTGCTGGTAGCTCTGCTCACCCGCACTGGGACC
                 Consensus (534) AAAGGC    TGC GT GCTC  CTCA   GCACTGGGACC
                                              ─────────────────── Section 15
                           (575) 575      580       590       600       615
     hR4Rd_ENST00000359069 (553) TAGAGCTCAGAAGACGAGAGGACAGACTGCCGTGTTGCCA
   R4Rd_2310002J15Rikcontig (159) TGGAGCTG-GAGGACTAAGAAGACAGACGGC--TGCTGCTT
                 Consensus (575) T GAGCT  GA GAC  AGA GACAGAC GC   TG TGC
                                              ─────────────────── Section 16
                           (616) 616       630       640       656
     hR4Rd_ENST00000359069 (594) -CCACAGGCTGGACCATGGACCCCAAGAGATGGTCGTCAA
   R4Rd_2310002J15Rikcontig (197) GCCACAGCCTGGACCATGGACCCCATGAGATGGTTGTGAA
                 Consensus (616)  CCACAG CTGGACCATGGACCCCA GAGATGG GT AA
                                              ─────────────────── Section 17
                           (657) 657       670       680       697
     hR4Rd_ENST00000359069 (634) GAACCCATATGCCCACATCAGCATCCCCCGGGCTCACCTGC
   R4Rd_2310002J15Rikcontig (238) GAATCCATATGCCCACATCAGCATTCCTCGGGCTCACCTGC
                 Consensus (657) GAA CCATATGCCCACATCAGCAT CC  CGGGCTCACCTGC
                                              ─────────────────── Section 18
                           (698) 698       710       720       738
     hR4Rd_ENST00000359069 (675) GGCCTGACCTGGGGCAGCAGTTAGAGGTGGCTTCCACCTGT
   R4Rd_2310002J15Rikcontig (279) GCTCTGACCTGGGGCAGCAGTTAGAGGAGGTTCCTTCTTCA
                 Consensus (698) G  CTGACCTGGGGCAGCAGTTAGAGG GG T  C   T
```

FIG. 10

```
                                                                                  Section 19
                          (739) 739        750        760              779
hR4Rd_ENST00000359069     (716) TCCTCATCCTCGGAGATGCAGCCCCTGCCAGTGGGGCCCTG
R4Rd_2310002J15Rikcontig  (320) TCTTCCTCCTCTGAGACTCAGCCTCTGCCTGCAGGAACATG
              Consensus   (739) TC  TC  TCCTC  GAGA   CAGCC CTGCC G  GG  C TG
                                                                                  Section 20
                          (780) 780        790        800        810        820
hR4Rd_ENST00000359069     (757) TGCCCCAGAGCCAACCCACCTCTTGCAGCCGACCGAGGTCC
R4Rd_2310002J15Rikcontig  (361) TATCCCAGAGCCAGTGGGCCTCTTACAAACTACTGAAGCCC
              Consensus   (780) T   CCCAGAGCCA       CCTCTT CA   C AC GA G CC
                                                                                  Section 21
                          (821) 821        830        840        850        861
hR4Rd_ENST00000359069     (798) CAGGGCCCAAGGGCGCCAAGGGTAACCAGGGGGCTGCCCCC
R4Rd_2310002J15Rikcontig  (402) CTGGGCCCAAAGGTATCAAGGGCATCAAGGGTACTGCTCCT
              Consensus   (821) C GGGCCCAA GG   CAAGGG A C AGGG   CTGC CC
                                                                                  Section 22
                          (862) 862        870        880        890        902
hR4Rd_ENST00000359069     (839) ATCCAGAACCAGCAGGCCTGGCAGCAGCCTGGCAACCCCTA
R4Rd_2310002J15Rikcontig  (443) GAGCACGGCCAGCAGACCTGGCAGTCACCCTGCAATCCCTA
              Consensus   (862)    CA    CCAGCAG CCTGGCAG  CC    GCAA CCCTA
                                                                                  Section 23
                          (903) 903        910        920        930        943
hR4Rd_ENST00000359069     (880) CAGCAGCAGTCAGCGCCAGGCCGGACTGACCTACGCTGGCC
R4Rd_2310002J15Rikcontig  (484) TAGCAGTGGGCAACGTCCATCGGGACTGACTTATGCTGGCC
              Consensus   (903)  AGCAG    G  CA CG C    C GGACTGAC  TA GCTGGCC
                                                                                  Section 24
                          (944) 944        950        960        970        984
hR4Rd_ENST00000359069     (921) CTCCGCCCGCGGGGCGCGGGGATGACATCGCCCACCACTGC
R4Rd_2310002J15Rikcontig  (525) TGCCACCTGTAGGGCGTGGTGATGACATTGCCCACCACTGC
              Consensus   (944)   CC CC  G   GGGCG GG GATGACAT GCCCACCACTGC
                                                                                  Section 25
                          (985) 985        990       1000       1010       1025
hR4Rd_ENST00000359069     (962) TGCTGCTGCCCCTGCTGCCACTGCTGCCACTGCCCCCCCTT
R4Rd_2310002J15Rikcontig  (566) TGCTGCTGCCCTTGCTGCTCCTGCTGCCACTGTCCTCGCTT
              Consensus   (985) TGCTGCTGCCC  TGCTGC  CTGCTGCCACTG CC C CTT
                                                                                  Section 26
                         (1026) 1026       1040       1050       1066
hR4Rd_ENST00000359069    (1003) CTGCCGCTGCCACAGCTGCTGCTGCTGTGTCATCTCCTAGC
R4Rd_2310002J15Rikcontig  (607) CTGCCGTTGTCACAGCTGTT------GTGTTATCTCCTAGC
              Consensus  (1026) CTGCCG TG CACAGCTG T      GTGT ATCTCCTAGC
                                                                                  Section 27
                         (1067) 1067       1080       1090       1107
hR4Rd_ENST00000359069    (1044) CCAGCCCACCCTGCCAGGGCCAGGACCCAGACTTCAGCAAA
R4Rd_2310002J15Rikcontig  (642) -----TGACTATTGAACCTCCAGGGCTGTG----CAGCCCA
              Consensus  (1067)      AC  T   A    CCAGG C  G    CAGC  A
```

FIG. 10 (Cont'd.)

```
                                                                          Section 28
                            (1108) 1108         1120        1130              1148
    hR4Rd_ENST00000359069 (1085) TGTGGCTCACACAGTGCCGGGACATGCCGGGACATGCGGGG
    R4Rd_2310002J15Rikcontig (674) GGTTCCTG-CTCAATGCCAAAGTGTTGCTGGACATCAGGAG
                Consensus (1108)    GT   CT   C CA TGCC       T   C GGACAT   GG G
                                                                          Section 29
                            (1149) 1149         1160        1170              1189
    hR4Rd_ENST00000359069 (1126) TGGCTGTTGTCATGGGCGTCTGCCCCTTCACACCAGGCACT
    R4Rd_2310002J15Rikcontig (714) CAGCCGTTGTCATGAGCATCAGCCATTTCCTGCCCTGAGCA
                Consensus (1149)     GC GTTGTCATG GC TC GCC   TTC    CC   G  C
                                                                          Section 30
                            (1190) 1190         1200        1210       1220   1230
    hR4Rd_ENST00000359069 (1167) GGGGCTCAGACCCACCAGGAAGGTGGCCGTTCAGCCCGAGC
    R4Rd_2310002J15Rikcontig (755) GGGGAGCCTGTCCACCAG--------CGTTCAGCTGTAGC
                Consensus (1190) GGGG   C     CCACCAG              CGTTCAGC   AGC
                                                                          Section 31
                            (1231) 1231         1240        1250       1260   1271
    hR4Rd_ENST00000359069 (1208) -TCCTGAAACGGAATCCCAGGTCCTGGC-----TGG-----
    R4Rd_2310002J15Rikcontig (787) CTTCTGGAATAGGGTTCCAGCCACTAGCCATGTTGGCAACA
                Consensus (1231)    T CTG AA   G  T CCAG   CT GC      TGG
                                                                          Section 32
                            (1272) 1272         1280        1290       1300   1312
    hR4Rd_ENST00000359069 (1238) AGAGGGACACCCCTGATTACCTT-AAGGCCCAGGCAATAAA
    R4Rd_2310002J15Rikcontig (828) ACAGGGACACCCTTCACGTCCTGCAAGACTTTGGCAATAAA
                Consensus (1272) A AGGGACACCC T A     CCT   AAG C   GGCAATAAA
                                                                          Section 33
                            (1313) 1313         1320        1330       1340   1353
    hR4Rd_ENST00000359069 (1278) GCAGGGTGATCTTC---------------------------
    R4Rd_2310002J15Rikcontig (869) GCAGGATGAGCGTTGCTGNNCCTGNTGAAAANAAAMWAAAW
                Consensus (1313) GCAGG TGA C T
```

FIG. 10 (Cont'd.)

Section 1
                                              (1) 1         10        20          33
Translation of hR4Rd_ENST00000359069          (1) MAPPLPRREKAAASRSTQALGPRAQKTERTDCR
Translation of R4Rd_2310002J15Rikcontig       (1) ---------------------------------
                              Consensus       (1)
                                                                                                    Section 2
                                             (34) 34       40        50          66
Translation of hR4Rd_ENST00000359069          (34) VATTGWTMDPQEMVVKNPYAHISIPRAHLRPDL
Translation of R4Rd_2310002J15Rikcontig       (1) ------MDPHEMVVKNPYAHISIPRAHLRSDL
                              Consensus      (34)        MDP EMVVKNPYAHISIPRAHLR DL
                                                                                                    Section 3
                                             (67) 67              80              99
Translation of hR4Rd_ENST00000359069          (67) GQQLEVASTCSSSSEMQPLPVGPCAPEPTHLLQ
Translation of R4Rd_2310002J15Rikcontig       (27) GQQLEEVPSSSSSSETQPLPAGTCIPEPVGLLQ
                              Consensus      (67) GQQLE    S SSSSE QPLP G C PEP   LLQ
                                                                                                    Section 4
                                            (100) 100      110      120         132
Translation of hR4Rd_ENST00000359069         (100) PTEVPGPKGAKGNQGAAPIQNQQAWQQPGNPYS
Translation of R4Rd_2310002J15Rikcontig      (60) TTEAPGPKGIKGIKGTAPEHGQQTWQSPCNPYS
                              Consensus     (100) TE PGPKG KG   G AP    QQ WQ P NPYS
                                                                                                    Section 5
                                            (133) 133      140      150         165
Translation of hR4Rd_ENST00000359069         (133) SSQRQAGLTYAGPPPAGRGDDIAHHCCCPCCH
Translation of R4Rd_2310002J15Rikcontig      (93) SGQRPSGLTYAGLPVGRGDDIAHHCCCPCCS
                              Consensus     (133) S QR AGLTYAG PP GRGDDIAHHCCCPCC
                                                                                                    Section 6
                                            (166) 166           184
Translation of hR4Rd_ENST00000359069         (166) CCHCPPFCRCHSCCCCVIS
Translation of R4Rd_2310002J15Rikcontig     (126) CCHCPRFCRCHSCCVIS--
                              Consensus     (166) CCHCP FCRCHSCC

FIG. 11

VEGF-A (VEGF$^{164}$ dependent upregulation of R2R$^1$ in the developing ventricular septum of the mouse embryo. Left = wild-type, right = VEGF$^{120/120}$ knockout mouse, lacing the VEGF$^{164}$ isoform.

R2R1/2 IN DIAGNOSIS AND THERAPY

RELATED APPLICATIONS

This application is a continuation application of U.S. application Ser. No. 13/957,760, filed Aug. 2, 2013, now abandoned, which is a continuation application of PCT Application No. PCT/IB2012/000177, filed Feb. 2, 2012, and published in English on Aug. 27, 2015, as International Publication No. WO 2012/127289 A1, which claims the priority to European Patent Application No. 11250127.5, filed Feb. 3, 2011, the disclosure of each of which is incorporated herein by reference in its entirety.

STATEMENT REGARDING ELECTRONIC FILING OF A SEQUENCE LISTING

A Sequence Listing in ASCII text format, submitted under 37 C.F.R. § 1.821, entitled 9013-128TSCT2_ST25.txt, 12,492 bytes in size, generated on Dec. 19, 2016 and filed via EFS-Web, is provided in lieu of a paper copy. The Sequence Listing is incorporated herein by reference into the specification for its disclosures.

FIELD OF THE INVENTION

The present invention provides novel genes that support the development/maintenance of the refined three-dimensional architecture of the lung as well as medicaments and compositions for treating pulmonary diseases and/or conditions.

BACKGROUND OF THE INVENTION

The expression of intermediate filament (Krt6), EDC (Epidermal Differentiation Complex) and SCC (Stratified epithelium-secreted protein gene complex) genes permits cellular survival in hostile environments. This expression profile leads to squamous differentiation and is a hallmark of skin epithelial cells. The inventors found that this transcriptional program is also vital for the refinement of pulmonary architecture (late branching morphogenesis): cells in distal airways and blood vessels need to assume a flat shape and acquire mechanical flexibility in an oxygen-rich environment. Proteins encoded by the intermediate filament group and associated EDC and SCC genes permit this kind of cell shape and flexibility. At the same time, the lung needs to maintain progenitor cells that are able to differentiate in cells capable of building such proteins. These progenitor or basal cells typically express the intermediate filament gene Krt14.

The lung is exposed to vast amounts of mechanical and oxidative stress and resembles the skin in this respect. The squamous differentiation program as mentioned above is the primary line of defence. Cells that line the distal airways and blood vessels of the lung need to withstand this stress and need to be replaced in case of cell death by a pool of progenitor cells.

Two human pathologies stand out by failure of this system.
1. Bronchopulmonary dysplasia (BPD): Lungs of infants, which are born prematurely, are more susceptible to lung injury such as mechanical stress. Also, lungs of premature infants surviving lung injury often heal with significant scarring or bronchopulmonary dysplasia (BPD). These lungs have a limited or underdeveloped regenerative potential.
2. Chronic obstructive pulmonary disease (COPD): Lungs of adult COPD patients seem to respond inappropriately to noxious stimuli such as smoking. Although they develop a barrier against these stimuli, their lack of regenerative capabilities in case of cell death leads to deformation of lung airways and blood vessels. Both BPD and COPD lead to significant morbidity and mortality.

SUMMARY OF THE INVENTION

The present invention stems from the finding that two genes play important roles in tissue development and cancer biology. In particular, the inventors have discovered that these two genes are expressed in pulmonary cells and are required for late branching morphogenesis of pulmonary epithelium and endothelium and support the development/maintenance of the refined three dimensional architecture of the lung. These genes are essential in the squamous differentiation program and development/maintenance of the progenitor (Krt14 expressing) cell pool. Moreover, the inventors have identified crucial roles for these genes in cancer biology, particularly processes associated with the acquisition of an immortal and metastatic phenotype (including cancer progression and metastasis) and cardiac development.

The inventors have ascertained the sequences of the murine and human forms of these genes. In view of their co-ordinated expression and function as regenerative genes for respiratory cells, the inventors have designated these genes $R2R^1$ and $R2R^2$. For simplicity, the bulk of this specification will use the term "$R2R^{1/2}$" which is intended to represent the longer phrase "$R2R^1$ and/or $R2R^2$"

Accordingly, references to the $R2R^{1/2}$ are to be understood as encompassing all mammalian forms of these genes including, for example, human and rodent (mouse, rabbit, guinea pig, rat etc) forms. Furthermore, in addition to encompassing the entire $R2R^1$ and/or $R2R^2$ gene sequences, it is to be understood that these designations also encompass fragments, portions, mutants, derivatives and/or homologous/orthologues of any of the genes described herein. In this regard, it should be understood that the term "$R2R^1$" encompasses the murine sequence encoded by the cDNA sequences designated 2200001115Rik or RIKEN cDNA 2200001115 as well as the seven human homologues designated FAM25A, FAM25B, FAM25C, FAM25D, FAM25E, FAM25G and FAM25HP.

In addition, where appropriate, the term "$R2R^{1/2}$" encompasses the proteinaceous products of the $R2R^1$ and/or $R2R^2$ genes or fragments or portions thereof.

In particular, the term "$R2R^{1/2}$" or indeed either of the terms "$R2R^1$" or "$R2R^2$", encompass the sequences given as SEQ ID NOS: 1-12 below or fragments, portions, analogues, variants or derivatives thereof.

The sequence of an exemplary transcript of the murine $R2R^1$ gene is given below as SEQ ID NO: 1

```
                                            SEQ ID NO: 1
acactgacacggaccgaaggagtggaaaaagctttacctgtcactgtctg ctgccatacgATGCTGGGAGGCCTGGGGAAGCTGGCGGCCGAGGGCCTGG

CCCACCGCACAGAGAAAGCCACTGGGGGAGCAGTTCACGCAGTGGAAGAG

GTGGTGAGCGAGGTGGTGGGCCACGCCAAGGAGGTTGGAGAGAAGACCAT

TAATGACGCCCTAAAGAAAGCCCAAGAATCAGGAGACAGGGTGGTGAAGG

AGGTCACTGAGAAGGTCACCCACACCATCACTGATGCTGTTACCCATGCG
```

GCAGAAGGCCTGGGAAGACTGGGACAGtgagcctgcctaccagcatggct ggcccttcctgaaggtcaataaagagtgtgaaacgtgaaaaaaaaaaaa aaataacaaaaaaaaaaaaaaaaa The coding or translated part of this sequence is underlined and comprises some 267 nucleotides. This particular portion of SEQ ID NO: 1 has been designated SEQ ID NO: 2.

One of skill in this field will appreciate that the 267 translated nucleotides yield a protein comprising 89 amino acids and having the following sequence (designated SEQ ID NO: 3)

SEQ ID NO: 3
MLGGLGKLAAEGLAHRTEKATGGAVHAVEEVVSEVVGHAKEVGEKTINDA

LKKAQESGDRVVKEVTEKVTHTITDAVTHAAEGLGRLGQ

In addition, the inventors have ascertained the complete sequence of an exemplary human transcript of the R2R[1] gene and this is given as SEQ ID NO: 4 below:

SEQ ID NO: 4
actgtctgctgccacacgATGCTGGGAGGCCTGGGGAAGCTGGCTGCCGA

AGGCCTGGCCCACCGCACCGAGAAGGCCACCGAGGGAGCCATTCATGCCG

TGGAAGAAGTGGTGAAGGAGGTGGTGGGACACGCCAAGGAGACTGGAGAG

AAAGCCATTGCTGAAGCCATAAAGAAAGCCCAAGAGTCAGGGGACAAAAA

GATGAAGGAAATCACTGAGACAGTGACCAACACAGTCACAAATGCCATCA

CCCATGCAGCAGAGAGTCTGGACAAACTTGGACAGtgagtgcacctgcta ccacggccttccccagtctcaataaaaagccatgacatgtg The coding or translated part of this sequence is underlined and comprises some 267 nucleotides. This particular portion of SEQ ID NO: 4 has been designated SEQ ID NO: 5.

One of skill in this field will appreciate that the 267 translated nucleotides yield a protein comprising 89 amino acids and having the following sequence (designated SEQ ID NO: 6)

SEQ ID NO: 6
MLGGLGKLAAEGLAHRTEKATEGAIHAVEEVVKEVVGHAKETGEKAIAEA

IKKAQESGDKKMKEITETVTNTVTNAITHAAESLDKLGQ

The sequence of an exemplary transcript of the murine R2R[2] gene is given below as SEQ ID NO: 7

SEQ ID NO: 7
gtgactggctgctgtctctagttgttgaggcctcttgggatctyggcgct macmccwtgctytagwgactccgatagctcccrmggctccagtgsasmcc tcggkcggnggnagggaaaaggcacttgctggtagctctgctcacccgca ctgggacctggagctggaggactaagaagacagacggctgctgcttgcca cagcctggaccATGGACCCCCATGAGATGGTTGTGAAGAATCCATATGCC

CACATCAGCATTCCTCGGGCTCACCTGCGCTCTGACCTGGGGCAGCAGTT

AGAGGAGGTTCCTTCTTCATCTTCCTCCTCTGAGACTCAGCCTCTGCCTG

CAGGAACATGTATCCCAGAGCCAGTGGGCCTCTTACAAACTACTGAAGCC

CCTGGGCCCAAAGGTATCAAGGGCATCAAGGGTACTGCTCCTGAGCACGG

CCAGCAGACCTGGCAGTCACCCTGCAATCCCTATAGCAGTGGGCAACGTC

CATCGGGACTGACTTATGCTGGCCTGCCACCTGTAGGGCGTGGTGATGAC

ATTGCCCACCACTGCTGCTGCTGCCCCTTGCTGCTCCTGCTGCCACTGTCC

TCGCTTCTGCCGTTGTCACAGCTGTTGTGTTATCTCCtagctgactattg aacctccagggctgtgcagcccaggttcctgctcaatgccaaagtgttgc tggacatcaggagcagccgttgtcatgagcatcagccatttcctgccctg agcaggggagcctgtccaccagcgttcagctgtagccttctggaataggg ttccagccactagccatgttggcaacaacagggacacccttcacgtcctg caagactttggcaataaagcaggatgagcgttgctgnncctgntgaaaan aaamwaaawacwgccgttgtcacarcygttrtgttatctmmkagstgacw attgtaammtycagrgctgtrmagcccrggkksckgctcaatgccaaagt gttgmtgsmcmtcrggrgsrgccaagcttttacgcggtacccgggattttt tttgtacaaaaaggggcccccctattagg The coding or translated part of this sequence is underlined and comprises some 426 nucleotides. This particular portion of SEQ ID NO: 7 has been designated SEQ ID NO: 8.

One of skill in this field will appreciate that the 426 translated nucleotides yield a protein comprising 142 amino acids and having the following sequence (designated SEQ ID NO: 9)

SEQ ID NO: 9
MDPHEMVVKNPYAHISIPRAHLRSDLGQQLEEVPSSSSSSETQPLPAGTC

IPEPVGLLQTTEAPGPKGIKGIKGTAPEHGQQTWQSPCNPYSSGQRPSGL

TYAGLPPVGRGDDIAHHCCCCPCCSCCHCPRFCRCHSCCVIS

In addition, the inventors have ascertained the complete sequence of an exemplary human transcript of the R2R[2] gene and this is given as SEQ ID NO: 10 below:

SEQ ID NO: 10
cttgaacccgggaggcagaggttgcagtgagccgagatcgcgcagctgca ctccagcctgggcaacagagcaagactccatctcagaaaagaagcagaaa gcctccaagagccaatggctctcaagcatcttggtctctgctaagaagag gctcagaggcttagaagccctgcctcgccggggcttttgaggtgtgtgagc aatggctggggactgcaggcccgggaatctgagggcctcaccccacttcc tttccagagccgtgacctcaggctcacctcctgccctcctctcaggcaag ctgcagatgccctttagggccaggccatgcccggatgtgaggggctga gtcactggtttggcagtgcccctcagagcccaggcctgggctgccaccca cctgaggacgagggctgggccagctgtcgtgctccagttgctgggcctc ttgggatcttgggaacccatctctgagcccgccccATGGCCCCGCCCC

TCCCAAGGAGGGAAAAGGCGGCTGCCAGTCGCTCAACTCAGGCACTGGGA

CCTAGAGCTCAGAAGACCGAGAGGACAGACTGCCGTGTTGCCACCACAGG

-continued

CTGGACCATGGACCCCCAAGAGATGGTCGTCAAGAACCCATATGCCCACA

TCAGCATCCCCCGGGCTCACCTGCGGCCTGACCTGGGGCAGCAGTTAGAG

GTGGCTTCCACCTGTTCCTCATCCTCGGAGATGCAGCCCCTGCCAGTGGG

GCCCTGTGCCCCAGAGCCAACCCACCTCTTGCAGCCGACCGAGGTCCCAG

GGCCCAAGGCCGCCAAGGGTAACCAGGGGGCTGCCCCCATCCAGAACCAG

CAGGCCTGGCAGCAGCCTGGCAACCCCTACAGCAGCAGTCAGCGCCAGGC

CGGACTGACCTACGCTGGCCCTCCGCCCGCGGGGCGCGGGGATGACATCG

CCCACCACTGCTGCTGCTGCCCCTGCTGCCACTGCTGCCACTGCCCCCCC

TTCTGCCGCTGCCACAGCTGCTGCTGCTGTGTCATCTCCtagcccagccc accctgccagggccaggacccagacttcagcaaatgtggctcacacagtg ccgggacatgccgggacatgcggggtggctgttgtcatgggcgtctgccc cttcacaccaggcactggggctcagacccaccaggaaggtggccgttcag cccgagctcctgaaacggaatcccaggtcctggctggagagggacacccc tgattaccttaaggcccaggcaataaagcagggtgatcttc The coding or translated part of this sequence is underlined and comprises some 552 nucleotides. This particular portion of SEQ ID NO: 10 has been designated SEQ ID NO: 11.

One of skill in this field will appreciate that the 552 translated nucleotides yield a protein comprising 184 amino acids and having the following sequence (designated SEQ ID NO: 12)

SEQ ID NO: 12
MAPPLPRREKAAASRSTQALGPRAQKTERTDCRVATTGWTMDPQEMVVKN

PYAHISIPRAHLRPDLGQQLEVASTCSSSSEMQPLPVGPCAPEPTHLLQP

TEVPGPKGAKGNQGAAPIQNQQAWQQPGNPYSSSQRQAGLTYAGPPPAGR

GDDIAHHOCCCPCCHCCHCPPFCRCHSCCCCVIS

As such, the present invention relates to the genes encoded by the sequences designated as SEQ ID NOS: 1, 2, 4, 5, 7, 8, 10 and 11, as well as any fragments, portions, mutants, variants, derivatives and/or homologues/orthologues thereof. Typically, fragments, portions, mutants, variants, derivatives and/or homologues/orthologues are functional or active—that is, they retain the function of the wild type $R2R^{1/2}$ genes.

The term "mutants" may encompass naturally occurring mutants or those artificially created by the introduction of one or more nucleic acid additions, deletions, substitutions or inversions.

One of skill in this field will readily understand that genes homologous to the human and murine $R2R^{1/2}$ genes detailed above may be found in a number of different species, including, for example, other mammalian species. Homologous genes may exhibit as little as approximately 20 or 30% sequence homology or identity however, in other cases, homologous genes may exhibit at least 40, 50, 60, 65 70, 75, 80, 85, 90, 91, 92, 93, 94, 95, 96, 97, 98, 99% homology to the various nucleotide sequences given above. As such, homologous genes from other species are to be included within the scope of this invention.

Using the various nucleic acid and amino acid sequences described herein, one of skill in the art could readily identify related sequences in other species, such as other mammals etc. For example, nucleic acid obtained from a particular species may be probed using the probes described herein, for homologous or closely related sequences.

In addition, it should be understood that the present invention also relates to the products of the genes encompassed by this invention and in particular the peptides encoded by SEQ ID NOS: 3, 6, 9 and 12. Furthermore, fragments, portions, analogues, variants, derivatives of any of these or homologous and/or identical proteins are also within the scope of this invention. Typically, fragments, portions, derivatives, variants and/or homologues are functional or active—that is they retain the function of the wild type $R2R^{1/2}$ protein.

In addition, proteins, polypeptides/peptides homologous/identical to any of the proteins encoded by SEQ ID NOS: 3, 6, 9 and 12 are also within the scope of this invention. Protein or polypeptide/peptide sequences which are considered as homologous or identical to any of the sequences described herein may exhibit as little as 20% or 30% sequence identity/homology. However, homologous/identical sequences may be at least 40, 50, 60, 65, 70, 75, 80, 85, 90, 95, 96, 97, 98 or 99% homologous or identical. Insofar as the invention relates to fragments of any of the protein or polypeptide/peptide sequences described herein, it should be understood that a fragment may comprise anywhere between about 10 and n−1 amino acids (where "n" is the number of amino acids in the complete sequence). For example, a fragment may comprise about 10, 15, 20, 30, 40, 50, 60, 70, 80, 90, 100, 110, 120 or about 125 amino acids (the maximum number of amino acids being determined by the number of amino acids in the complete sequence)—such fragments/portions may be referred to as peptide fragments. In one embodiment, the peptide fragments may be antigenic and/or immunogenic—that is to say, they retain the ability to bind antibodies exhibiting specificity, affinity and/or selectivity for the native (complete) antigen—such as those encoded by SEQ ID NOs: 3, 6, 9 and 12.

One of skill in this field will readily understand that for the various nucleic acid sequences and polypeptides described herein, natural variations due to, for example, polymorphisms, may exist between $R2R^{1/2}$ genes and proteins isolated from any given species. In addition, it is well known in the art, that the degeneracy of the genetic code permits substitution of one or more bases in a codon without alteration to the primary amino acid sequence. As such, genetic degeneracy may be exploited in order to yield variant nucleic acid sequences which encode peptide or protein sequences substantially identical to the antigen sequences described herein. Indeed, variant sequences provided by this invention may manifest as proteins and/or genes that exhibit one or more amino acid/nucleic acid substitutions, additions, deletions and/or inversions relative to a reference sequence (for example any of the sequences described above).

As such, it is to be understood that all such variants, especially those that are functional or display the desired activity, are to be included within the scope of this invention.

In other embodiment, the invention relates to derivatives of any of the $R2R^{1/2}$ sequences described herein. The term "derivatives" may encompass $R2R^{1/2}$ gene or peptide sequences which, relative to those described herein, comprise one or more amino acid substitutions, deletions, additions and/or inversions.

Additionally, or alternatively, analogues of the various peptides described herein may be produced by introducing one or more conservative amino acid substitutions into the primary sequence. One of skill in this field will understand that the term "conservative substitution" is intended to embrace the act of replacing one or more amino acids of a protein or peptide with an alternate amino acid with similar properties and which does not substantially alter the physcio-chemical properties and/or structure or function of the native (or wild type) protein. Analogues of this type are also encompassed with the scope of this invention.

As is well known in the art, the degeneracy of the genetic code permits substitution of one or more bases in a codon without changing the primary amino acid sequence. Consequently, although the sequences described in this application are known to encode the $R2R^{1/2}$ proteins described herein, the degeneracy of the code may be exploited to yield variant nucleic acid sequences which encode the same primary amino acid sequences.

As stated, the present inventors have discovered that the $R2R^{1/2}$ genes (and their protein products) are involved in pulmonary and cardiac morphogenesis events (such as cell signalling/transition etc.) and support the development of the three dimensional architecture of the lung and heart. As such, a first aspect of this invention provides the $R2R^{1/2}$ genes and/or $R2R^{1/2}$ proteins, for use as medicaments or for use in treating diseases affecting cell/tissue development/structure, differentiation, proliferation and/or morphogenesis. For example, the $R2R^{1/2}$ genes and/or $R2R^{1/2}$ proteins may be for use in treating, for example pulmonary and/or cardiac diseases and/or conditions as well as cancer—particularly cancers affecting tissues of the pulmonary or cardiac system.

In certain embodiments, the invention may provide the $R2R^{1/2}$ genes and/or $R2R^{1/2}$ proteins for use in modulating cell transition events such as, for example, mesenchymal to epithelial transition (MET) events and events involved in the reverse process, epithelial to mesenchymal transition (EMT).

In a second aspect, the present invention provides the $R2R^{1/2}$ genes and/or $R2R^{1/2}$ proteins for use in treating pulmonary diseases and/or conditions or their use in the manufacture of a medicament for the treatment of pulmonary diseases and/or conditions.

In a further aspect, the invention provides the $R2R^1$ gene and/or protein for use in treating cardiac diseases. In one embodiment, the $R2R^1$ gene and/or protein may be used to treat diseases affecting the development/structure, differentiation, proliferation and/or morphogenesis of cardiac cells/tissues. In one embodiment, the invention may provide the $R2R^1$ gene and/or protein for use in treating diseases and/or conditions affecting the development and/or formation of the ventricular septum.

In a further aspect, the invention provides the $R2R^1$ gene and/or protein for use in treating cancer. In one embodiment, the $R2R^1$ gene and/or protein may be used to treat cancers affecting a variety of tissues including, for example, pulmonary and/or cardiac tissue. More generally, the invention may extend to the treatment of any cancer involving aberrant/defective MET/EMT processes. Examples of at least some of the cancers which may be treated using the genes and/or proteins of the invention are detailed below.

It is reiterated that the terms "$R2R^1$", "$R2R^2$" and "$R2R^{1/2}$" encompass not only the complete gene/peptide sequences as described above, but also fragments, analogues, homologues, orthologues, variants and derivatives thereof.

The terms "pulmonary disease" or "pulmonary condition" may include pathologies of the lung such as those affecting lung development or the 3D architecture of pulmonary tissues. For example, "pulmonary diseases" may include diseases and/or conditions affecting the epithelial cells lining the airways of the lung, the endothelial cells of the pulmonary vessel network and/or the differentiation and/or growth of these cells. As such, pulmonary diseases may include diseases affecting pulmonary morphogenesis pathways and events. Pulmonary diseases and/or conditions affecting the differentiation of certain pulmonary cell types (for example the squamous epithelial cells) or the generation and/or maintenance of progenitor (basal) cell populations may also be treated with the compounds, medicaments and methods described herein. By way of specific example, diseases such as Bronchopulmonary Dysplasia (BPD) and/or Chronic obstructive pulmonary disease (COPD) may be treated using the compounds described herein. In other embodiments, the terms "pulmonary disease" or "pulmonary condition" may include cell proliferation or neoplastic disorders such as cancer, including, for example, non-small cell lung cancer (NSCLC) and/or small cell lung cancer (SCLC).

The terms "cardiac disease" or "cardiac condition" may include pathologies of the heart such as those affecting cardiac development or the 3D architecture of cardic tissues. Cardiac diseases may include diseases affecting cardiac morphogenesis pathways and events, in particular mesenchymal to epithelial and epithelial to mesenchymal transition. By way of specific example, diseases such as atrial and ventricular septal defects, atrioventricular canal defects, malformation of cardiac (atrioventricular) valves' and coronary arteries may be treated using the compounds described herein.

It should also be understood that since the $R2R^{1/2}$ genes/proteins described herein have been shown to play a role in morphogenesis events (such as cell signalling etc.) and support the development of the three dimensional architecture of complex tissues such as the lung and/or heart, they may find application in regenerative medicine. By way of example, where stem cells (for example adult, embryionic or reprogrammed somatic cells (such as iPS cells) are used to repair or reconstruct, for example, damaged or diseased tissue, the proteins and/or genes provided by this invention may be used to facilitate tissue development.

The $R2R^{1/2}$ protein and genes play an important role in the morphogenesis events of the lung and heart as gatekeepers of epithelial to mesenchymal and mesenchymal to epithelial transition, Therefore, they may find application in cancer biology and cancer treatment. By way of example, diseases such as transformation of localized cancer to cancer metastasis may be treated using compounds described herein.

In addition to providing various uses and medicaments involving the $R2R^{1/2}$ genes and/or proteins described herein, the present invention also provides methods of treating subjects suffering from any of the diseases and/or conditions described herein, including any of the cardiac/pulmonary diseases and/or conditions outlined above. As such a third aspect of this invention provides a method of treating a cardiac/pulmonary disease and/or condition comprising the steps of administering to a subject in need thereof, a therapeutically effective amount of the $R2R^1$ and/or $R2R^2$ genes and/or $R2R^1$ and/or $R2R^2$ proteins described herein.

Where a cardiac or pulmonary disease or condition results from, or is associated with, a lack of, or defective, $R2R^{1/2}$ gene and/or protein expression/function, the use of a functional $R2R^{1/2}$ gene or protein as described herein, may provide a means of restoring normal (or wild type) $R2R^{1/2}$ gene/protein function so as to treat and/or alleviating the symptoms of the disease or condition.

It will be appreciated that the uses, medicaments and methods of treatment described herein may require the generation of recombinant R2R$^{1/2}$ genes/proteins and as such, the present invention further contemplates methods of generating and/or expressing recombinant R2R$^{1/2}$ genes and/or proteins. One of skill in this field will appreciate that PCR techniques may be exploited to selectively obtain R2R$^{1/2}$ gene sequences from a variety of sources including, for example, lung tissue. These sequences may be ligated to various expression or regulatory control sequences such as, for example, promoter, operator, inducer, enhancer and/or silencer elements, ribosome binding sites and/or terminator sequences. Suitable regulatory or expression control sequences may be selected by those skilled in this field for any given host. In a further embodiment, the PCR derived R2R$^{1/2}$ gene sequences may be introduced into a vector (such as a plasmid or expression cassette). In one embodiment, the vector may further comprise a nucleotide sequence of a tag or label to assist in protein purification procedures.

A host cell may be transformed with the vector and maintained under conditions suitable to induce expression of the R2R$^{1/2}$ gene sequence and production of recombinant R2R$^{1/2}$. Vectors into which R2R$^{1/2}$ gene sequences (or fragments thereof) have been cloned, may be introduced or transfected into cells using a variety of techniques—such techniques may otherwise be referred to as transfection protocols. Transfection protocols utilise conditions which render cell membranes permeable to compounds such as nucleic acids. By way of example, it may be possible to facilitate the transfection of vectors, including expression vectors, into cells using electroporation, heat shock, chemical compounds such, for example, calcium phosphate, stronitium phosphate, microinjection techniques and/or gene guns.

Techniques used to purify recombinant proteins generated in this way are known and, where the recombinant protein is tagged or labelled, these may include the use of, for example, affinity chromatography techniques.

In view of the above, the fourth and fifth aspects of this invention provide an expression vector comprising an R2R$^{1/2}$ gene sequence and a host cell transformed therewith, respectively.

In addition to providing the R2R$^{1/2}$ genes and/or proteins as a means of treating various diseases and/or conditions (for example cardiac and/or pulmonary diseases and/or conditions), the present invention also provides compounds capable of modulating the expression of the R2R$^{1/2}$ genes and which may be useful in the treatment of conditions that result from, or are associated with R2R$^{1/2}$ gene/protein over-expression. Such compounds may be oligonucleotides, preferably antisense oligonucleotides which may take the form of, for example DNA and/or RNA. In one embodiment, the oligonucleotides are RNA molecules known to those skilled in this field as small/short interfering and/or silencing RNA and which will be referred to hereinafter as siRNA. Such siRNA oligonucleotides may take the form of native RNA duplexes or duplexes that have been modified in some way (for example by chemical modification) to be nuclease resistant. Additionally, or alternatively, the siRNA oligonucleotides may take the form of short hairpin RNA (shRNA) expression or plasmid constructs that correspond to, or comprise, the siRNAs described herein.

The oligonucleotides provided by this invention may be designed to modulate the expression the R2R$^{1/2}$ genes. By analysing native or wild-type R2R$^{1/2}$ sequences and with the aid of algorithms such as BIOPREDsi, one of skill in the art could easily determine or computationally predict nucleic acid sequences that have an optimal knockdown effect for these genes (see for example: http://www.biopredsi.org/start.html). Accordingly, the skilled man may generate and test an array or library of different oligonucleotides to determine whether or not they are capable of modulating the expression of the R2R$^{1/2}$ genes.

In view of the above, the antisense oligonulcoeotides and/or siRNA molecules described herein may be used (i) treat any of the diseases and/or conditions described herein—in particular (ii) to treat pulmonary diseases and/or disorders, (iii) to treat cardiac diseases and/or conditions and (iv) to treat cancer. Furthermore, the antisense oligonulcoeotides and/or siRNA molecules described herein may be used in the manufacture of medicaments for treating the diseases outlined as (i)-(iv) above or in methods of treating subjects suffering from such diseases and/or disorders.

In addition, antibodies (or antigen binding fragments thereof) capable of binding to the R2R$^{1/2}$ proteins may be useful in the treatment of the diseases and/or conditions described herein, including, for example, cardiac and/or pulmonary diseases and/or conditions. Antibodies which block or neutralise the function of the R2R$^{1/2}$ proteins may be particularly useful where a disease and/or condition results from over expression of an R2R$^{1/2}$ protein. The techniques used to generate monoclonal antibodies (mAbs) are well known and can easily be exploited to generate mAbs specific for either of the R2R$^1$ and/or R2R$^2$ proteins or fragments thereof. Similarly, the processes used to generate polyclonal antibodies are also well established and may be used to generate antibodies specific for either of the R2R$^1$ and/or R2R$^2$ proteins or fragments thereof.

Other compounds useful in the treatment of diseases and/or conditions described herein (for example cardiac and/or pulmonary conditions and/or disorders or cancer) may include for example, proteins, peptides, amino acids, carbohydrates and other small organic molecules.

In addition to the above, isolated R2R$^{1/2}$ nucleotide and/or protein sequences may be used as the basis for the design of probes and/or primers for use in ex vivo and/or in situ detection and expression studies. Typical detection studies include, for example, polymerase chain reaction (PCR), hybridisation studies, sequencing protocols and immunological and/or Southern/Northern blotting detection techniques.

In principle any polynucleotide (or oligonucleotides) or polypeptide fragment designed from the sequences described above may be used in said detection and/or expression studies.

Typically, polynucleotide fragments for use as probes and/or primers, will comprise 10-30 nucleotides (although other lengths may be useful for certain applications) and exhibit a degree of specificity for a particular sequence and will not bind unrelated sequences. Similarly, polypeptide fragments to be used as probes may also be relatively short and typically may comprise 5-20 amino acids (although other slightly shorter or longer lengths may be useful for some applications).

It will be readily understood that careful selection of the primer/probe sequence and the use of stringent (preferably highly stringent) hybridisation conditions will minimise any non-selective binding.

Accordingly, oligonucleotides probe and/or primer sequences having at least 50%, at least 75%, at least 90% or at least 95% complementarity as well as those having exact (i.e. 100%) complementarity to all or part of the nucleotide sequences described herein are to be considered as encompassed within this invention.

Hybridisation between a probe/primer and a nucleic acid sequence (such as any described herein) may be effected at a temperature of about 40° C.-75° C. in 2-6×SSC (i.e. 2-6× NaCl 17.5 g/l and sodium citrate (SC) at 8.8 g/l) buffered saline containing 0.1% sodium dodecyl sulphate (SDS). Of course, depending on the degree of similarity between the probe/primer and the sequence, buffers with a reduced SSC concentration (i.e. 1×SSC containing 0.1% SDS, 0.5×SSC containing 0.1% SDS and 0.1×SSC containing 0.1% SDS).

Polypeptide probes having at least 30%, 50%, 70%, 75%, 80%, 85%, 90% or 95% identity as well as those having exact (i.e. 100% identity) to all or part of the amino acid sequences disclosed herein, are to be considered as within the scope of this invention.

As such, a further aspect of this invention provides oligonucleotides probes and/or primers designed to hybridise to all or part of a sequence selected from the group consisting of SEQ ID NOS: 1; 2; 4; 5; 7; 8; 10 and 11. In addition, a further aspect provides polypeptide probes designed to bind to all or part of a sequence selected from the group consisting of SEQ ID NOS: 3; 6; 9 and 12

In another aspect the present invention provides a method of diagnosing a pulmonary disease or condition and/or susceptibility thereto, wherein the method comprises determining if the $R2R^1$ and/or $R2R^2$ genes in a subject are aberrantly expressed.

Subjects diagnosed as suffering from, for example cancer and/or a cardiac and/or pulmonary disease and/or condition may exhibit aberrant (i.e. increased or decreased) $R2R^1$ and/or $R2R^2$ gene/protein expression. The term "aberrant expression" should be understood to encompass levels of gene expression that are either increased and/or decreased relative to the expression observed in sample derived from a healthy subject or a subject who is not suffering from the diseases and/or condition (namely a cardiac or pulmonary disease and/or condition or cancer).

The term "sample" should be understood as including samples of bodily fluids such as whole blood, plasma, serum, saliva, sweat and/or semen. In other instances "samples" such as tissue biopsies and/or scrapings may be used. In particular lung tissue biopsies and/or scrapings may be used. In addition, a sample may comprise a tissue or gland secretion and washing protocols may be used to obtain sample of fluid secreted into, for example, the lung. Suitable washing protocols may include broncho-alveolar lavage procedures. One of the skill in this field will appreciate that the samples described above may yield quantities of $R2R^{1/2}$ nucleic acid (i.e. DNA or RNA) and/or $R2R^{1/2}$ proteins, peptides (or fragments thereof). Furthermore, these methods may comprise the first step of providing a sample from a subject suspected of suffering from a pulmonary disease and/or condition or who may be at risk of developing a pulmonary disease and/or condition.

An increase in the level of $R2R^1$ and/or $R2R^2$ gene/protein expression may be associated with any of the diseases and/or conditions described above or susceptibility thereto. For example an increase in $R2R^{1/2}$ gene/protein expression may be indicative of excessive cellular proliferation and/or differentiation—and may be associated with, for example, a neoplastic condition such as cancer (i.e. lung cancer). Decreases in $R2R^1$ and/or $R2R^2$ gene/protein expression may be indicative of pathological conditions characterised by poor or impaired cardiac/lung development. Such conditions may result in tissue injury (due to mechanical stresses acting within the heart/lung), scarring, loss of structural integrity of the heart/lung and deformed or damaged lung airways or cardiac structure.

One of skill in the art will be familiar with the techniques that may be used to identify levels of proteins and/or genes, such as the $R2R^{1/2}$ genes and/or proteins, in samples such as those listed above.

Such techniques may include, for example, polymerase chain reaction (PCR) based techniques such as real-time PCR (otherwise known as quantitative PCR). In the present case, real time-PCR may used to determine the level of expression of the genes encoding the $R2R^1$ and/or $R2R^2$ proteins. Typically, and in order to quantify the level of expression of a particular nucleic acid sequence, reverse transcriptase PCR may be used to reverse transcribe the relevant mRNA to complementary DNA (cDNA). Preferably, the reverse transcriptase protocol may use primers designed to specifically amplify an mRNA sequence of interest. Thereafter, PCR may be used to amplify the cDNA generated by reverse transcription.

Typically, the cDNA is amplified using primers designed to specifically hybridise with a certain sequence and the nucleotides used for PCR may be labelled with fluorescent or radiolabelled compounds.

One of skill in the art will be familiar with the technique of using labelled nucleotides to allow quantification of the amount of DNA produced during a PCR. Briefly, and by way of example, the amount of labelled amplified nucleic acid may be determined by monitoring the amount of incorporated labelled nucleotide during the cycling of the PCR.

Further information regarding the PCR based techniques described herein may be found in, for example, PCR Primer: A Laboratory Manual, Second Edition Edited by Carl W. Dieffenbach & Gabriela S. Dveksler: Cold Spring Harbour Laboratory Press and Molecular Cloning: A Laboratory Manual by Joseph Sambrook & David Russell: Cold Spring Harbour Laboratory Press.

Other techniques that may be used to determine the level of $R2R^1$ and/or $R2R^2$ gene expression in a sample include, for example, Northern and/or Southern Blot techniques. A Northern blot may be used to determine the amount of a particular mRNA present in a sample and as such, could be used to determine the amount of $R2R^1$ and/or $R2R^2$ gene expression. Briefly, mRNA may be extracted from, for example, a cell based or cell free system modified to include expressible $R2R^1$ and/or $R2R^2$ genes using techniques known to the skilled artisan, and subjected to electrophoresis. A nucleic acid probe, designed to hybridise (i.e. complementary to) an mRNA sequence of interest—in this case the mRNA encoding the $R2R^1$ and/or $R2R^2$ proteins, may then be used to detect and quantify the amount of a particular mRNA present in a sample.

Additionally, or alternatively, a level of $R2R^1$ and/or $R2R^2$ gene expression may be identified by way of microarray analysis. Such a method would involve the use of a DNA microarray that comprises nucleic acid derived from the $R2R^1$ and/or $R2R^2$ genes. To identify the level of $R2R^1$ and/or $R2R^2$ gene expression, one of skill in the art may extract the nucleic acid, preferably the mRNA from a system (either cell based or cell free) subjected to the method described in the first aspect of this invention, and subject it to an amplification protocol such as, reverse transcriptase PCR to generate cDNA. Preferably, primers specific for a certain mRNA sequence—in this case the sequences encoding the $R2R^1$ and/or $R2R^2$ genes may be used.

The amplified $R2R^1$ and/or $R2R^2$ cDNA may be subjected to a further amplification step, optionally in the presence of labelled nucleotides (as described above). Thereafter, the optionally labelled amplified cDNA may be contacted with the microarray under conditions that permit binding with the DNA of the microarray. In this way, it may be possible to identify a level of $R2R^1$ and/or $R2R^2$ gene expression.

Further information regarding the above described techniques may be found in, for example, PCR Primer: A Laboratory Manual, Second Edition Edited by Carl W. Dieffenbach & Gabriela S. Dveksler: Cold Spring Harbour Laboratory Press and Molecular Cloning: A Laboratory Manual by Joseph Sambrook & David Russell: Cold Spring Harbour Laboratory Press.

In order to determine the level of $R2R^{1/2}$ proteins in a sample, immunological techniques exploiting agents capable of binding $R2R^{1/2}$ proteins, may be used.

In one embodiment, the diagnostic methods described above may comprise the step of contacting a substrate (or portion thereof) with a sample to be tested, under conditions which permit the association, interaction, binding and/or immobilization of any $R2R^{1/2}$ protein present in the sample, to said substrate.

Suitable substrates may include, for example, glass, nitrocellulose, paper, agarose and/or plastics. A substrate such as, for example, a plastic material, may take the form of a microtitre plate.

Alternatively, the substrate to be contacted with the sample to be tested may comprise an agent capable of binding $R2R^{1/2}$ protein(s). Preferably, the agent capable of binding the $R2R^{1/2}$ proteins is/are bound to the substrate (or at least a portion thereof). Suitable binding agents may include, for example, antibodies such as monoclonal or polyclonal antibodies and/or other types of peptide or small molecule capable of binding to the $R2R^{1/2}$ proteins. It is to be understood that this definition applies to all types of binding agent mentioned herein. As such, the substrate (or a portion thereof) may be contacted with the sample to be tested under conditions that permit binding or interaction between the agents capable of binding the $R2R^{1/2}$ protein and any $R2R^{1/2}$ protein present in the sample.

Any $R2R^{1/2}$ protein bound to the substrate or agents capable of binding the $R2R^{1/2}$ protein(s), may be detected with the use of a further agent capable of binding the $R2R^{1/2}$ protein(s) (referred to hereinafter as the "primary binding agent"). Additionally, or alternatively, the primary binding agents may have affinity for, or bind to, $R2R^1/R2R^2$ protein: substrate complexes or complexes comprising the $R2R^{1/2}$ proteins and the abovementioned agents capable of binding the $R2R^{1/2}$ proteins.

The primary binding agents may be conjugated to moieties which permit them to be detected (referred to hereinafter as "detectable moieties"). For example, the primary agents may be conjugated to an enzyme capable of reporting a level via a colorimetric chemiluminescent reaction. Such conjugated enzymes may include but are not limited to Horse Radish Peroxidase (HRP) and Alkaline Phosphatase (AlkP). Additionally, or alternatively, the primary binding agents may be conjugated to a fluorescent molecule such as, for example a fluorophore, such as FITC, rhodamine or Texas Red. Other types of molecule that may be conjugated to binding agents include radiolabelled moieties.

Alternatively, any $R2R^{1/2}$ protein bound to the substrate or agents capable of binding the $R2R^{12}$ proteins, may be detected by means of a yet further binding agent (referred to hereinafter as "secondary binding agents") having affinity for the primary binding agents. Preferably, the secondary binding agents are conjugated to detectable moieties.

The amount of primary binding agent (or secondary binding agent bound thereto) bound to $R2R^{1/2}$ protein(s), may represent the level of $R2R^{1/2}$ protein(s) present in the sample tested.

In one embodiment, the methods for identifying a level of $R2R^{1/2}$ protein, may take the form of "dip-stick" test, wherein a substrate (or portion thereof) is contacted with a sample to be tested under conditions which permit the binding of any $R2R^{1/2}$ protein(s) present in the sample to the substrate or a binding agent bound or immobilised thereto.

In a further embodiment, the methods may take the form of an immunological assay such as, for example, an enzyme-linked immunosorbent assay (ELISA). An ELISA may take the form of a "capture" ELISA wherein, a sample to be tested is contacted with a substrate, and any $R2R^{1/2}$ protein(s) present in the sample is/are "captured" or bound by a binding agent (capable of binding the $R2R^{1/2}$ proteins) bound or immobilized to the substrate. Alternatively, the sample may be contacted with the substrate under conditions that permit "direct" binding between any $R2R^{1/2}$ protein(s) present in the sample and the substrate.

Each of the ELISA methods described above may comprise a "direct" $R2R^{1/2}$ protein detection step or an "indirect" identification step. ELISAs involving such steps may be known as "direct" ELISAs or "indirect" ELISAs.

A "direct" ELISA may involve contacting the sample to be tested with a substrate under conditions that permit the binding of any $R2R½$ protein(s) present in the sample to the substrate and/or a binding agent bound thereto. After an optional blocking step, bound $R2R^{1/2}$ protein(s) may be detected by way of an agent capable of binding the $R2R^{1/2}$ proteins (i.e. a primary binding agent). Preferably, the primary binding agents are conjugated to a detectable moiety.

An "indirect" ELISA may comprise the further step of, after contacting the $R2R^{1/2}$ protein(s) with a primary binding agent, using a further binding agent (secondary binding agent) with affinity or specificity for the primary binding agent. Preferably, the secondary binding agent may be conjugated to a detectable moiety.

Other immunological techniques which may be used to identify a level of $R2R^{1/2}$ protein in a sample include, for example, immunohistochemistry wherein binding agents, such as antibodies capable of binding the $R2R^{1/2}$ protein(s), are contacted with a sample, preferably a tissue sample, under conditions which permit binding between any $R2R^{1/2}$ protein(s) present in the sample and the $R2R^{1/2}$ protein binding agent. Typically, prior to contacting the sample with the binding agent, the sample is treated with, for example a detergent such as Triton X100. Such a technique may be referred to as "direct" immunohistochemical staining.

Alternatively, the sample to be tested may be subjected to an indirect immunohistochemical staining protocol wherein, after the sample has been contacted with a $R2R^{1/2}$ protein binding agent, a further binding agent (a secondary binding agent) which is specific for, has affinity for, or is capable of binding the $R2R^{1/2}$ protein binding agent, is used to detect $R2R^{1/2}$ protein/binding agent complexes.

The skilled man will understand that in both direct and indirect immunohistochemical techniques, the binding agent or secondary binding agent may be conjugated to a detectable moiety. Preferably, the binding agent or secondary binding agent is conjugated to a moiety capable of reporting a level of bound binding agent or secondary binding agent, via a colorimetric chemiluminescent reaction.

In order to identify the levels of $R2R^{1/2}$ protein(s) present in the sample, one may compare the results of an immunohistochemical stain with the results of an immunohistochemical stain conducted on a reference sample. By way of example, a sample that reveals more or less bound $R2R^{1/2}$ protein binding agent (or secondary binding agent) than in a reference sample, may have been provided by a subject with a particular disease and/or condition.

Other techniques that exploit the use of agents capable of binding the R2R½ proteins include, for example, techniques such as Western blot or dot blot. A Western blot may involve subjecting a sample to electrophoresis so as to separate or resolve the components, for example the proteinaceous components, of the sample. The resolved components may then be transferred to a substrate, such as nitrocellulose. In order to identify any $R2R^{1/2}$ protein(s) present in the sample, the substrate may be contacted with a binding agent capable of binding $R2R^{1/2}$ protein(s) under conditions which permit binding between any $R2R^{1/2}$ protein(s) present in the sample and the agents capable of binding $R2R^{1/2}$ protein(s).

Advantageously, the agents capable of binding $R2R^{1/2}$ protein(s) may be conjugated to a detectable moiety.

Alternatively, the substrate may be contacted with a further binding agent having affinity for the binding agent(s) capable of binding $R2R^{1/2}$ protein(s). Advantageously, the further binding agent may be conjugated to a detectable moiety.

In the case of a dot blot, the sample or a portion thereof, may be contacted with a substrate such that any $R2R^{1/2}$ protein(s) present in the sample is bound to or immobilised on the substrate. Identification of any bound or immobilised $R2R^{1/2}$ protein(s) may be conducted as described above.

In any of the abovementioned techniques, the amount of primary or secondary binding agent detected is representative of, or proportional to, the amount of $R2R^{1/2}$ protein present in the sample. Furthermore, the results obtained from any or all of the diagnostic methods described herein may be compared with the results obtained from reference or control samples derived from healthy subjects known not to be suffering from, or susceptible to, a particular disease or disorder (such as, for example a cardiac and/or pulmonary disease or disorder and/or cancer).

A further aspect of this invention provides a method of identifying or obtaining agents which modulate the expression of the $R2R^1$ and/or $R2R^2$ genes, said method comprising the steps of contacting the $R2R^1$ and/or $R2R^2$ genes with a test agent and detecting any modulation of $R2R^{1/2}$ gene expression.

One of skill in this field will appreciate that a method such as that described in this 9th aspect of the invention may be conducted in systems such as, for example, cell based or cell free systems, modified to include the $R2R^1$ and/or $R2R^2$ genes. By way of example, cells may be transfected with nucleic acid comprising either the $R2R^1$ or $R2R^2$ gene. In one embodiment, the nucleic acid may take the form of a vector (for example a plasmid or expression cassette as described above).

In one embodiment, the results obtained from the methods described above may be compared to those obtained from a control method in which the $R2R^1$ and/or $R2R^2$ genes have not been contacted with a test agent. In this way, it may be possible to determine whether or not said agent is capable of modulating the expression of the $R2R^1$ and/or $R2R^2$ genes. Where the level of $R2R^1$ and/or $R2R^2$ gene expression is less or greater than the level of expression detected in the control method, the test agent may be useful as a modulator of $R2R^1$ and/or $R2R^2$ gene expression. Where the level of expression is the same as that observed in the control methods, the test agent is most likely not capable of modulating the expression of the $R2R^1$ and/or $R2R^2$ genes.

Suitable test agents may take the form of nucleic acids, for example the antisense oligonucleotides described above, proteins, peptides, amino acids, antibodies (and fragments thereof), carbohydrates and other small organic molecules.

In further aspect, the present invention provides pharmaceutical compositions comprising the $R2R^{1/2}$ genes/proteins described above, antisense oligonucleotides (DNA or RNA) as described herein and/or any of the agents identified by the methods provided by the 9th aspect of this invention and which are capable of modulating the expression or function of the $R2R^1$ and/or $R2R^2$ genes/proteins, in association with a pharmaceutically acceptable excipient, carrier or diluent. Such compositions may find application in, for example, the treatment of the various diseases and/or conditions described herein including the cardiac and/or pulmonary diseases and/or cancers described above.

Preferably, the pharmaceutical compositions provided by this invention are formulated as sterile pharmaceutical compositions. Suitable excipients, carriers or diluents may include, for example, water, saline, phosphate buffered saline, dextrose, glycerol, ethanol, ion exchangers, alumina, aluminium stearate, lecithin, serum proteins, such as serum albumin, buffer substances such as phosphates, glycine, sorbic acid, potassium sorbate, partial glyceride mixtures of saturated vegetable fatty acids, water salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycon, sodium carboxymethylcellulose, polyacrylates, waxes, polyethylene-polypropylene-block polymers, polyethylene glycol and wool fat and the like, or combinations thereof.

Said pharmaceutical formulation may be formulated, for example, in a form suitable for oral, parenteral or topical administration. In one embodiment, the pharmaceutical composition may be formulated such that it can be inhaled. Compositions that are to be administered by inhalation may take the form of fine powders or solutions which can be aerosolised and inhaled as droplets. One of skill in this field will be familiar with devices that may be used to deliver compositions directly to the lung by, for example, inhalation. The droplet or particle size of the composition can be altered such that the drug can access different regions of the lung. For example, once inhaled, small particles or droplets may penetrate deep into the lung tissue and in some cases may reach the alveoli.

Pharmaceutical compositions formulated for topical administration may be presented as an ointment, solution or a suspension in an aqueous or non-aqueous liquid, or as an oil-in-water liquid emulsion.

Compounds capable of modulating the $R2R^1$ and/or $R2R^2$ genes, such as, for example, those identified by the methods described herein or the $R2R^{1/2}$ gene/protein fragments, antisense oligonucleotides, and antibodies described herein, may find further application as modulators of cell differentiation. As stated, the inventors have determined that the $R2R^1$ and $R2R^2$ genes and their products are involved in the pathways that modulate the differentiation of pulmonary epithelial cells, particularly the squamous epithelial cells generated from the pulmonary epithelial progenitor or basal cell population (i.e. $Krt14^{+ve}$ cells).

Compounds that modulate cell (for example, pulmonary epithelial cell) differentiation may be particularly useful in the treatment of disorders such as BPD which yield damaged and scarred lungs with a reduced or underdeveloped regenerative potential. As such, by administering or using a compound which modulates cell differentiation, it may be possible to improve or restore the regenerative potential of the lung. One of skill in this field will readily understand that compounds capable of enhancing or promoting R2R$^1$ and/or R2R$^2$ gene expression or which restore the function of these genes may be particularly useful.

In a further aspect, the present invention provides an animal model for studying tissue development and/or cell transition events as well as certain diseases and/or conditions (including cardiac and/or pulmonary diseases and/or conditions and cancer). In one embodiment, the animal model may be generated by manipulating or modulating (i.e. up or down regulating) the expression of the R2R$^{1/2}$ genes/proteins. Additionally or alternatively, an animal model may be generated by disrupting R2R$^{1/2}$ gene expression. As described above, the disclosure of a number of human and murine R2R$^{1/2}$ gene/protein sequences herein ensure that the skilled man could readily manipulate/modulate these sequences in situ to generate animal models. For example, "knock-out" animals may be created, that is, the expression of R2R$^{1/2}$ gene sequences is reduced or substantially eliminated. Such models are useful for testing the effects of drugs potentially useful in the treatment of the diseases and/or disorders described herein and/or for determining the function or role of a particular gene. Alternatively, animal models in which the expression of the R2R$^{1/2}$ genes/proteins are upregulated, may also be created. In this way, the efficacy and function of drugs aimed at suppressing upregulated R2R$^{1/2}$ gene/protein expression may be tested. It is also possible to investigate the effect of upregulated R2R$^{1/2}$ gene protein expression in these animals.

In other embodiments, substitutions, additions, deletions and/or inversions may be introduced into the R2R$^{1/2}$ gene sequences in order to effect changes in the activity of the proteins and to help elucidate the function of certain domains, amino acids and the like. Additionally, or alternatively, knockout animals, such as those described above, may be transformed with any of the gene sequences described herein. This is particularly useful where the effect of a variant or mutated R2R$^{1/2}$ gene or efficacy of a drug or compound capable of suppressing the expression or function of said variant or mutated sequence, is to be investigated. The present invention will now be described in detail with reference to the following Figures which show:

BRIEF DESCRIPTION OF THE DRAWINGS

FIG. 4A. Volcanoplot showing on the y-axis the significance of each gene for testing whether the expression profile over embryonic age differs between the Vegf+/+ and Vegf120/120 genotypes (based on LIMMA). The x-axis shows the fold change in induction when comparing the 2 genotypes, Vegf+/+ versus Vegf120/120 at E16.5. Upregulation of Krt6a, EDC and SCC genes in wild type ker+ cells is highlighted. FIG. 4B. Airway epithelial cells in E16.5 Vegf+/+ lungs defined by anti-cytokeratin 4, 5, 6, 8, 10, 13, and 18 staining. Distal airway cells develop a flat or squamous cell morphology (yellow arrow) in contrast to their proximal neighbours (white arrow) FIG. 4C. Allocation of differential expression along chromosome 3. This highlights the downregulation of the genes in the EDC of Vegf120/120 as compared to wildtype.

FIG. 5A: IF=Intermediate Filament Keratins (red) group anchoring to the Desmosome (orange) containing Dsc1. Pkp1 (purple) links Intermediate Keratin Filaments to Cadherin proteins of the Adherens type junction (yellow). Pkp1 also regulates the protein content of the Desmosome. EDC and SCC cluster genes interact with Intermediate Filament Keratins. The star symbol highlights the upregulated genes and gene clusters in the Intermediate Filament network. Upregulation of Eps8l1 (coding for an actin-capping protein) coordinates Intermediate Filament with Actin remodelling.

FIG. 5B: Volcanoplot showing on the y-axis the significance of each gene for testing whether the expression profile over embryonic age differs between endothelial cells of Vegf+/+ and Vegf120/120 genotypes (based on LIMMA). The x-axis shows the fold change in induction when comparing the 2 genotypes, Vegf+/+ versus Vegf120/120 at E16.5. The Krt, Dsc1, Pkp1, EDC and SCC cluster genes are highlighted. The Krt genes upregulated in wild type Vegf+/+ il+ cells differ from the Krt genes expressed in the equivalent wild type ker+ cells. Krt14 and Krt1 are trademark basal cell genes.

FIG. 5C: Immunofluorescent image (40× magnification) of GS-IB4 isolectin staining cells (il+ cells) in wild type E16.5 embryonic lungs. Il+ cells follow the same architectural pattern of the ker+ cells of the distal airways.

FIG. 8: cDNA sequence alignments of the human hR4RA transcript (=human $R2R^1$) versus mouse R4Ra transcript (=mouse $R2R^1$). It should be noted that the largest contig constructed from sequenced RIKEN cDNA 2200001115 gene clones is referred to as 'mouse R4Ra transcript (=mouse $R2R^1$)'.

FIG. 9: Protein sequence alignments of the translated human hR4RA (=human $R2R^1$) transcript versus translated mouse R4Ra (=mouse $R2R^1$) transcript.

FIG. 10: cDNA sequence alignments of the human hR4RD transcript (=human $R2R^2$) versus mouse R4Rd transcript (=mouse $R2R^2$). It should be noted that the largest contig constructed from sequenced RIKEN cDNA 2310002J15 gene clones is referred to as 'mouse R4Rd transcript (=mouse $R2R^2$)'.

FIG. 11: Protein sequence alignments of the translated human hR4RD (=human $R2R^2$) transcript versus translated mouse R4Rd (=mouse $R2R^2$) transcript.

FIG. 14A: RTqPCR: siRNA mediated knockdown of VEGFA and $VEGF^{165}$ expression leads to knockdown of KRT14 (basal cell marker) expression. KRT14 relative expression (PGK1 normalized), VEGFA and $VEGF^{165}$ are plotted versus siRNA. Included are two negative controls (called nr 10 and 11). siRNA directed against KRT14 expression is included as a positive control. FIGS. 14B-14C: siRNA VEGFA is directed against all VEGFA isoforms.

FIGS. 15A-15J depict the significance of changes in gene expression after administration during 24 h of an siRNA directed against VEGF. FIGS. 15A-15J are created by automated pathway analysis. All pathways are involved in keratinocyte differentiation: basal cell regeneration and squamous differentiation.

FIG. 16A illustrates the downregulation of FAM25 (Hs04194072_m1) expression (PGK1 normalized) after 24 h administration of the respective siRNA's in PBEC's. The human $R2R^2$ homologue: Two siRNA's (numbered 15 and 17) designed against C9orf169 (at concentrations of 5 and 20 nM respectively) were selected on the basis of their ability to downregulate C9orf169 expression in PBEC's. C9orf169 expression was evaluated by microarray analysis and RTqPCR. Probes for C9orf169 are present on the Affymetrix HT HG-U219 Human Gene Expression Array. FIG. 16B illustrates the downregulation (assessed by microarray analysis) of C9orf169 expression after 24 h administration of the respective siRNA's in PBEC's. The administration of siRNA's directed against the FAM25 family or VEGFA has no effect on C9orf169 expression. siRNA's directed against $R2R^1$ (human FAM25 family) and $R2R^2$ (human C9orf169) downregulate KRT14 expression and is the response similar to the one observed after administration of siRNA's directed against VEGFA and $VEGF^{165}$ siRNA mediated knockdown of the FAM25 family and C9orf169 leads to downregulation of KRT14 gene expression (basal cell marker). This response is most obvious after administration of siRNA's directed against C9orf169.

FIG. 16C illustrates the downregulation KRT14 expression (PGK1 normalized) after 24 h administration of the respective siRNA's in PBEC's. Included are also the siR-NA's directed against VEGFA and KRT14 for reason of comparison.

FIG. 19B illustrates the expression of ATP5A1 among global changes in gene expression of the oxidative phosphorylation pathway.

Figure 25A:
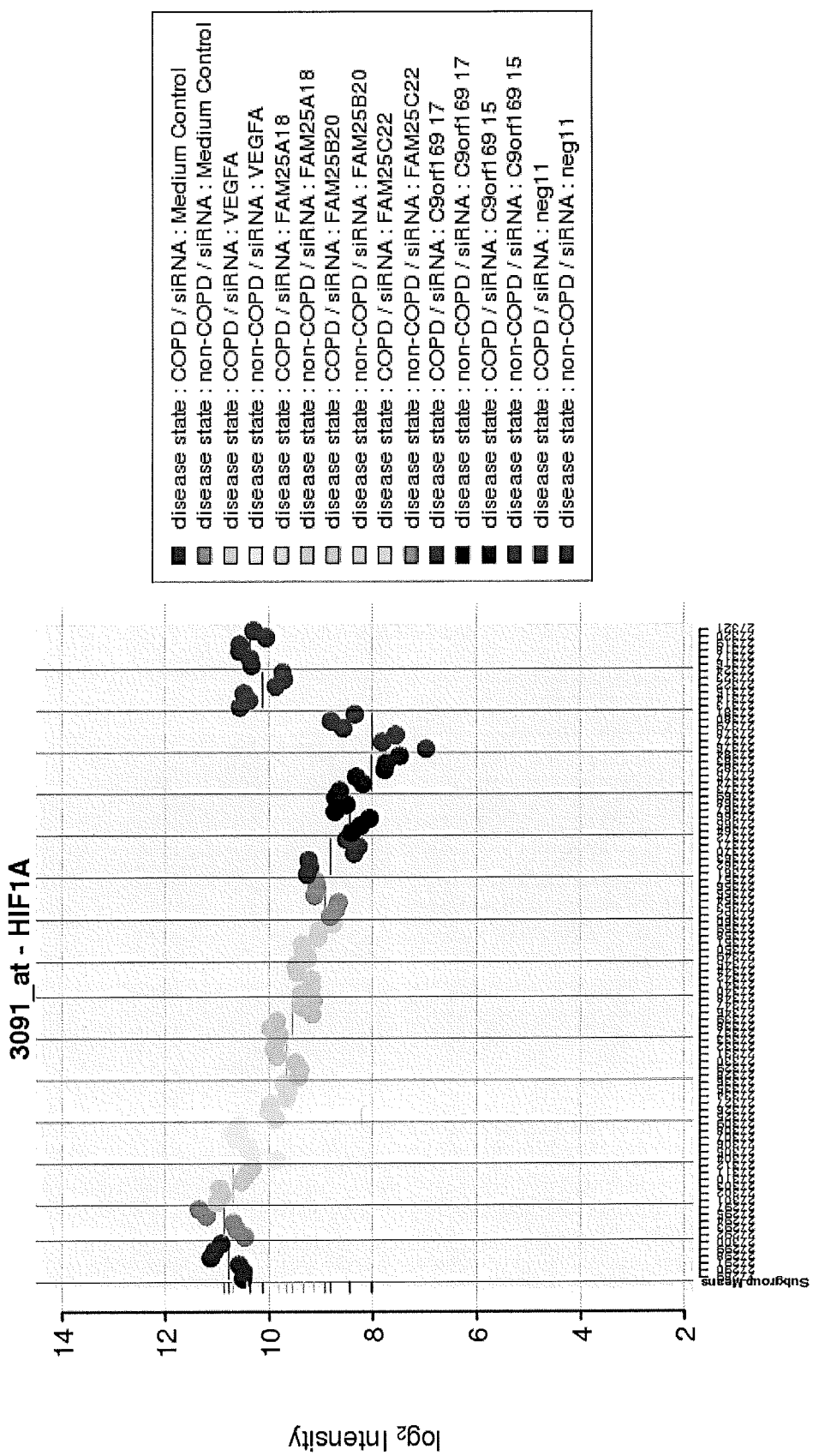
FIGS. 25A-25C: The expression of HIF1A (see Box 5 in FIG. 17) is tightly regulated by the expression of the human R2R homologues. siRNA mediated knockdown of the human R2R homologues will downregulate HIF1A expression (FIG. 25A). The downstream HIF1A effects on cellular respiration (oxidative phosphorylation) were described in 3 (see FIG. 17 Cellular respiration). The R2R homologues drive 'PERP type p53-p63' and HIF1A expression. As such 'tough' epithelial cells, equipped with the HIF1A armory, could develop unlimited growth potential under the influence of VEGFA/VEGF[165]. However, we observe at the same time that the epithelial cells are precluded from entering an immortal state. Expression of the R2R homologues will act as a brake for the expression of genes that could immortalize the cell. This is very obvious in the case of BCL2A1 (FIG. 25B), an anti-apoptosis gene whose expression confers resistance to therapy in cancer cells. siRNA mediated knockdown of the R2R homologues leads to upregulation of BCL2A1 expression. The R2R homologues act as a brake for BCL2A1 expression.
Figure 25B:
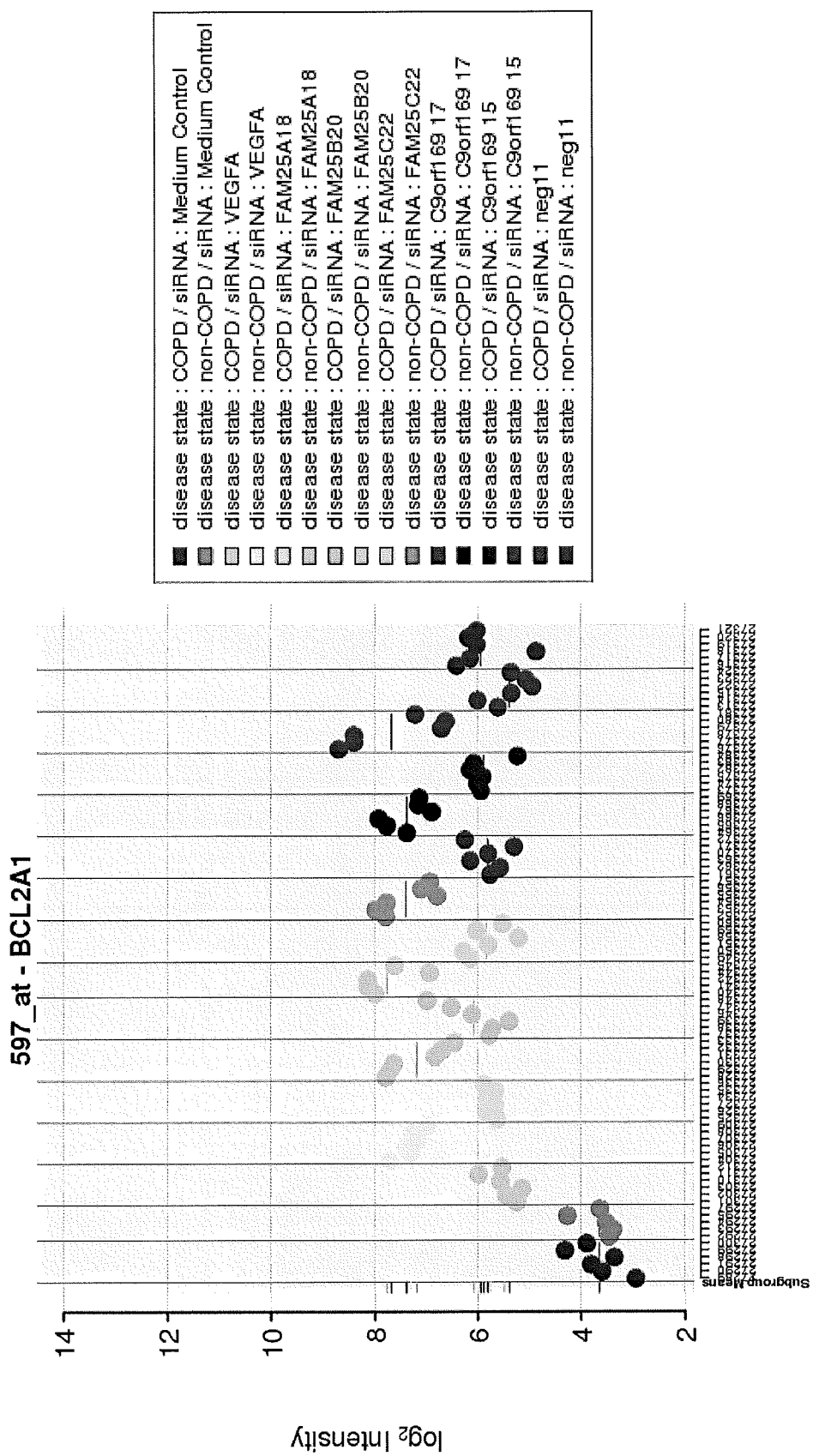
Figure 25C:
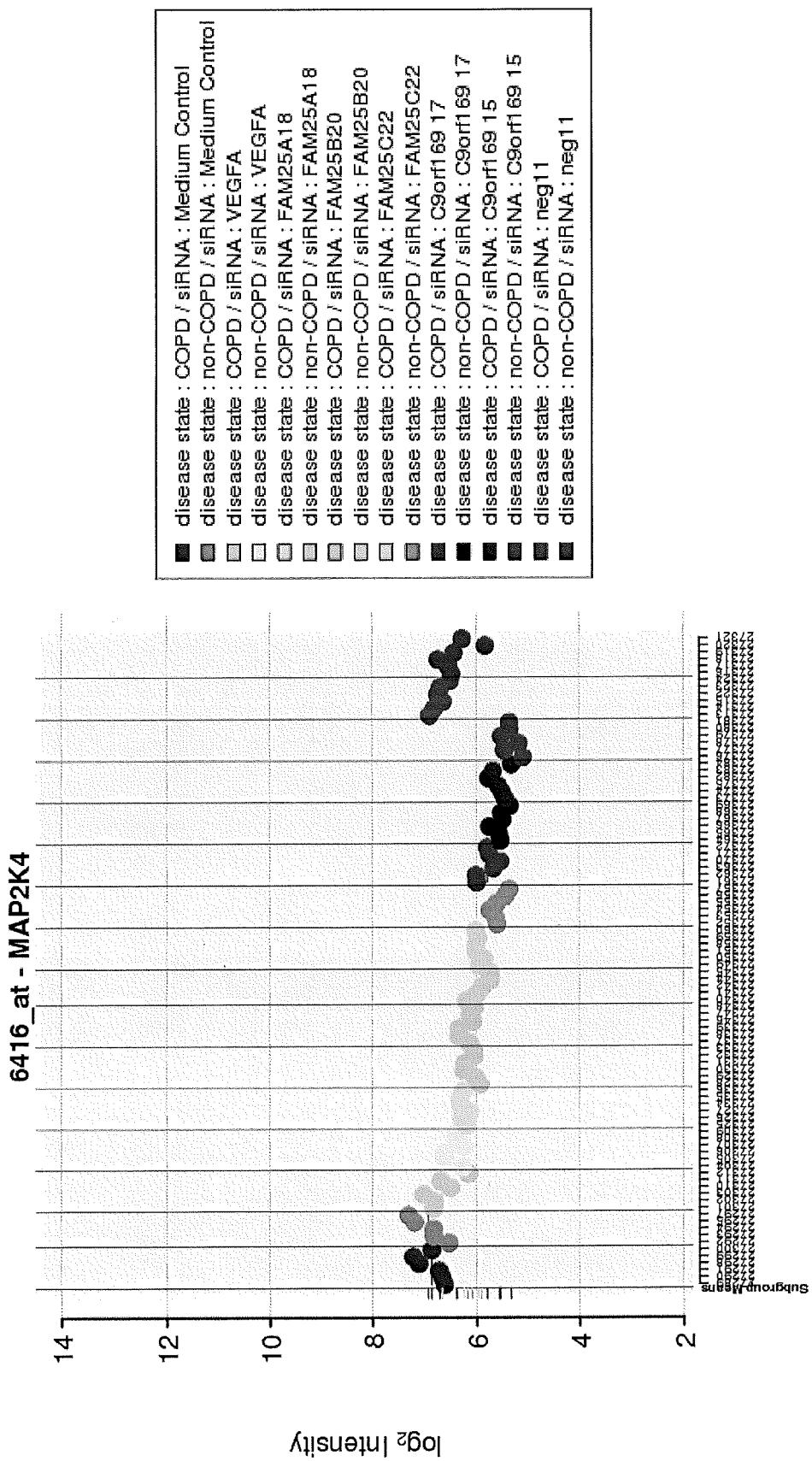

R2R homologues will also promote the expression of genes that permit cells to enter apoptosis if needed. This is demonstrated by siRNA mediated knockdown of the R2R homologues: the knockdown will cause a downregulation MAP2K4 (FIG. 25C) a tumor suppressor in lung adenocarcinoma.

Table 1. RIKEN cDNA 2200001I15 gene and RIKEN cDNA 2310002J15 gene among the top list of genes in SAM analysis of differential gene expression on E16.5 in wild type and Vegf120/120 knockout anti-cytokeratin 4-5-6-8-10-13-18 staining cells.

Table 2. RIKEN cDNA 2200001I15 gene and RIKEN cDNA 2310002J15 gene among the top list of genes in SAM analysis of differential gene expression on E16.5 in wild type and Vegf120/120 knockout GS-IB4 staining cells.

Table 3. Distribution of embryos according to age and Vegf genotype status. wt/wt=homozygous wild type (Vegf+/+), 120/wt=heterozygous Vegf120/+, and 120/120=homozygous Vegf120/120 knockout. (NG= not genotyped because of poor embryologic morphology).

TABLE 1

| Probe Set ID | Variance | UniGene ID | Alignments | Gene Title | Gene Symbol |
| --- | --- | --- | --- | --- | --- |
| 1448745_s_at | 44.327 | Mm.1121 | Chr3: 92166199-92169061 | Loricrin | Lor |
| 1451613_at | 25.931 | Mm.208047 | Chr3: 93405151-93418973 | Homerin | Hmr |
| 1449986_at | 21.731 | Mm.160339 | Chr16: 88647705-8864865 | RIKEN cDNA 2310034C09 gene | 2310034C09Rk |
| 1440186_s_at | 19.595 | Mm.44242 | Chr5: 36523188-36523428 | RIKEN cDNA 2310020A21 gene | 2310020A21Rik |
| 1421575_at | 18.532 | Mm.358728 | Chr16: 88666693-8866767 | RIKEN cDNA 2310057N15 gene | 2310057N15Rik |
| 1453218_at | 16.908 | Mm.292458 | Chr3: 92764649-92766321 | RIKEN cDNA 1110014K05 gene | 1110014K05Rik |
| 1459897_a_at | 16.677 | Mm.250717 | Chr7: 30460230-30464892 | suprabasin | Sbsn |
| 1420676_at | 16.402 | Mm.41969 | Chr3: 92731934-92733718 | Small proline rich-like 3 | Sprrl3 |
| 1420358_at | 13.819 | Mm.353193 | Chr16: 88647705-8870935 | Keratin associated protein 13 | Krtap13 |
| 1437019_at | 13.44 | Mm.27156 | Chr14: 33180971-3318446 | RIKEN cDNA 2200001I15 gene | 2200001I15RiK ← |
| 1456248_at | 12.776 | Mm.46390 | Chr3: 93078529-93078825 | RIKEN cDNA 2310002A05 /// LOC630971 gene | 2310002A05Rik /// LOC630971 |
| 1434227_at | 12.373 | Mm.268157 | Chr7: 30496664-30499855 | Keratin differentiation associated protein | Krtdap |
| 1420677_x_at | 12.312 | Mm.41969 | Chr3: 92731934-92733718 | Small proline rich-like 3 | Sprrl3 |
| 1439630_x_at | 12.212 | Mm.250717 | Chr7: 30463567-30464893 | suprabasin | Sbsn |
| 1420350_at | 11.873 | Mm.279773 | Chr3: 92754015-92755718 | Small proline rich-like 2 | Sprrl2 |
| 1428781_at | 11.64 | Mm.30138 | Chr7: 30485165-30489826 | RIKEN cDNA | 1110014F24Rik |
| 1452732_at | 11.02 | Mm.183043 | Chr6: 86593812-86595336 | RIKEN cDNA | 2300003P22Rik |
| 1419394_s_at | 10.266 | Mm.21567 | Chr3: 90754997-90755961 | S100 calcium binding protein (calgranulin a) | S100a8 |
| 1453092_at | 10.127 | Mm.35806 | Chr3: 93099607-93101077 | RIKEN cDNA 2300002G24 gene | 2300002G24Rik |
| 1435111_at | 9.396 | Mm.32861 | Chr7: 24063581-24063867 | RIKEN cDNA 2310011E23 gene | 2310011E23Rik |
| 1419709_at | 9.22 | Mm.136573 | Chr16: 36369769-3637463 | Stefin A3 | Stfa3 |
| 1435761_at | 9.202 | Mm.383370 | Chr16: 36196367-3620461 | Stefin A3 | Stfa3 |
| 1422784_at | 7.244 | Mm.302399 | Chr15: 101517949-101522 | Keratin Complex 2, basic, gene 6a | Krt2-6a |
| 1435760_at | 7.165 | Mm.300592 | Chr18: 42299151-4229971 | Cystatin A | Csta |
| 1448756_at | 6.71 | Mm.2128 | Chr3: 90778558-90781225 | S100 calcium binding protein A9 (calgranulin-B) | S100a9 |

TABLE 1-continued

| Probe Set ID | Variance | UniGene ID | Alignments | Gene Title | Gene Symbol |
|---|---|---|---|---|---|
| 1447669_s_at | 6.627 | Mm.215394 | Chr13: 13619774-1362001 | Guanine nucleotide binding protein (G Protein Subunit Gamma 4) | GnG4 |
| 1425336_x_at | 5.61 | Mm.422886 | Chr17: 33606481-3361073 | histocompatibility 2, K1, K region | H2-K1 |
| 1437145_s_at | 5.455 | Mm.46431 | Chr2: 25060827-25061091 | RIKEN cDNA | 2310002J15Rik ← |
| 1420741_x_at | 5.247 | Mm.291782 | Chr3: 92862612-92864302 | RIKEN cDNA | 2310069N01Rik |
| 1442339_at | 4.062 | Mm.187847 | Chr16: 36076009-3608118 | Stefin A2 like 1 | Stfa2L1 |
| 1427492_at | 3.963 | Mm.34964 | ChrX: 108755370-1087622 | Premature ovarian failure 1B | Pof1b |
| 1418722_at | 3.693 | Mm.236225 | Chr9: 110265012-1102681 | Neutrophilic granule protein | Ngp |
| 1419409_at | 3.69 | Mm.291769 | Chr3: 92741051-92741651 | Small proline rich-like 5 | Sprrl5 |
| 1436936_s_at | 3.42 | Mm.274770 | ChrX: 99684922-99685968 | Inactive X specific transcripts | Xist |
| 1427262_at | 3.408 | Mm.274770 | ChrX: 99663093-99685936 | Inactive X specific transcripts | Xist |
| 1430567_at | 3.377 | Mm.35369 | Chr18: 44114683-4414781 | Serine peptidase inhibitor, Kazal type 5 | Spink5 |
| 1422667_at | 3.336 | Mm.38498 | Chr11: 99947848-9995203 | Keratin complex 1, acidic, gene 15 | Krt1-15 |
| 1448881_at | 3.243 | Mm.26730 | Chr8: 112464257-1124682 | Haptoglobin | Hp |
| 1423547_at | 2.71 | Mm.45436 | Chr10: 116681442-116686 | Lysozyme | Lyzs |
| 1449586_at | 1.939 | Mm.4494 | Chr1: 137687809-1377356 | Plakophilin 1 | Pkp1 |
| 1449133_at | 1.932 | Mm.331191 | Chr3: 92569339-92571288 | Small proline-rich 1A | Sprr1a |
| 1449106_at | 1.901 | Mm.200916 | Chr11: 54746194-5475379 | Glutathione peroxidase 3 | Gpx3 |
| 1452543_a_at | 1.862 | Mm.2258 | Chr19: 9150684-9154982 | Secretoglobin, family 1A, member 1 | Scgb1a1 |
| 1450633_at | 1.859 | Mm.21075 | Chr13: 3837003-3837919 | Calmodulin 4 | Calm4 |
| 1459898_at | 1.826 | Mm.250717 | Chr7: 30460230-30464892 | suprabasin | Sbsn |
| 1429565_s_at | 1.815 | Mm.292457 | Chr3: 93103210-93104462 | Late cornified envelope 5A | Lce5a |
| 1429540_at | 1.727 | Mm.34382 | Chr7: 25076381-25078481 | Cornifelin | Cnfn |
| 1453801_at | 1.597 | Mm.180200 | Chr3: 94427502-94432590 | Thioesterase superfamily member 5 | Them5 |
| 1422672_at | 1.568 | Mm.140151 | Chr3: 92522208-92524192 | Small proline-rich protein 1B | Sprr1b |

TABLE 2

| Probe Set ID | Variance | UniGene ID | Gene Title | Gene Symbol |
|---|---|---|---|---|
| 1449586_at | 32.877 | Mm.4494 | plakophilin 1 | Pkp1 |
| 1423935_x_at | 30.173 | Mm.6974 | keratin complex 1, acidic, gene 14 | Krt1-14 |
| 1460347_x_at | 28.662 | Mm.6974 | keratin complex 1, acidic, gene 14 | Krt1-14 |
| 1438856_x_at | 23.207 | Mm.268618 | serine (or cysteine) peptidase inhibitor, clade B, member 5 | Serpinb5 |
| 1422667_at | 21.017 | Mm.38498 | keratin complex 1, acidic, gene 15 | Krt1-15 |
| 1422481_at | 20.962 | Mm.183137 | keratin complex 2, basic, gene 1 | Krt2-1 |
| 1424096_at | 20.14 | Mm.383993 | keratin complex 2, basic, gene 5 | Krt2-5 |
| 1451613_at | 20.135 | Mm.208047 | hornerin | Hrnr |
| 1453218_at | 18.792 | Mm.292458 | RIKEN cDNA 1110014K05 gene | 1110014K05Rik |
| 1441941_x_at | 18.5 | Mm.268618 | serine (or cysteine) peptidase inhibitor, clade B, member 5 | Serpinb5 |
| 1456203_at | 17.757 | — | RIKEN cDNA 1110020A10 gene | 1110020A10Rik |
| 1434227_at | 16.95 | — | keratinocyte differentiation associated protein | Krtdap |
| 1429067_at | 16.396 | — | calpain, small subunit 2 | Capns2 |
| 1440186_s_at | 16.186 | Mm.378865 | Transcribed locus | — |
| 1419709_at | 15.648 | Mm.136573 | stefin A3 | Stfa3 |
| 1422939_at | 14.807 | Mm.337362 | serine (or cysteine) peptidase inhibitor, clade B (ovalbumin), member 3B | Serpinb3b |
| 1422308_a_at | 14.219 | Mm.20973 | lectin, galactose binding, soluble 7 | Lgals7 |
| 1437019_at | 13.876 | Mm.27156 | RIKEN cDNA 2200001I15 gene | 2200001I15Rik ← |
| 1450633_at | 13.842 | Mm.21075 | calmodulin 4 | Calm4 |
| 1421117_at | 12.773 | Mm.336625 | dystonin | Dst |
| 1421752_a_at | 12.718 | Mm.268618 | serine (or cysteine) peptidase inhibitor, clade B, member 5 | Serpinb5 |
| 1418799_a_at | 12.316 | Mm.1225 | procollagen, type XVII, alpha 1 | Col17a1 |
| 1453801_at | 11.671 | Mm.180200 | thioesterase superfamily member 5 | Them5 |
| 1422940_x_at | 11.333 | Mm.337362 | serine (or cysteine) peptidase inhibitor, clade B (ovalbumin), member 3B | Serpinb3b |
| 1436392_s_at | 11.112 | Mm.3629 | transcription factor AP-2, gamma | Tcfap2c |
| 1452166_a_at | 10.901 | Mm.22662 | keratin complex 1, acidic, gene 10 | Krt1-10 |
| 1449938_at | 10.491 | Mm.1001 | placental protein 11 related | Pp11r |
| 1421040_a_at | 10.27 | Mm.371562 | glutathione S-transferase, alpha 2 (Yc2) | Gsta2 |
| 1437232_at | 10.198 | Mm.107214 | bactericidal/permeability-increasing protein-like 2 | Bpil2 |
| 1424623_at | 9.782 | Mm.268618 | serine (or cysteine) peptidase inhibitor, clade B, member 5 | Serpinb5 |
| 1418748_at | 9.085 | Mm.20940 | caspase 14 | Casp14 |
| 1418158_at | 9.029 | Mm.20894 | transformation related protein 63 | Trp63 |
| 1430551_s_at | 8.917 | Mm.195937 | lipase-like, ab-hydrolase domain containing 3 | Lipl3 |
| 1430550_at | 8.679 | Mm.195937 | lipase-like, ab-hydrolase domain containing 3 | Lipl3 |
| 1435761_at | 8.652 | Mm.136573 | stefin A3 | Stfa3 |
| 1448397_at | 8.545 | Mm.25652 | gap junction membrane channel protein beta 6 | Gjb6 |
| 1459898_at | 8.407 | Mm.250717 | suprabasin | MGI: 2446326 |
| 1422672_at | 8.373 | Mm.140151 | small proline-rich protein 1B | Sprr1b |
| 1459897_a_at | 8.371 | Mm.250717 | suprabasin | MGI: 2446326 |

TABLE 2-continued

| Probe Set ID | Variance | UniGene ID | Gene Title | Gene Symbol |
|---|---|---|---|---|
| 1428781_at | 8.218 | Mm.30138 | RIKEN cDNA 1110014F24 gene | 1110014F24Rik |
| 1419492_s_at | 8.128 | Mm.5341 | defensin beta 1 | Defb1 |
| 1439183_at | 8.102 | Mm.218784 | N-acylsphingosine amidohydrolase (alkaline ceramidase) 3 | Asah3 |
| 1419491_at | 8.028 | Mm.5341 | defensin beta 1 | Defb1 |
| 1427263_at | 7.99 | — | inactive X specific transcripts | Xist |
| 1416930_at | 7.471 | Mm.878 | lymphocyte antigen 6 complex, locus D | Ly6d |
| 1435760_at | 7.251 | Mm.300592 | cystatin A /// similar to Stefin homolog | MGI: 3524930 /// LOC547252 |
| 1439630_x_at | 7.031 | Mm.250717 | suprabasin | MGI: 2446326 |
| 1435639_at | 6.509 | — | RIKEN cDNA 2610528A11 gene | 2610528A11Rik |
| 1424976_at | 6.23 | Mm.120274 | ras homolog gene family, member V | Rhov |
| 1455519_at | 6.163 | Mm.383274 | desmoglein 1 beta | Dsg1b |
| 1455715_at | 5.932 | Mm.373656 | PREDICTED: *Mus musculus* RIKEN cDNA 2700099C18 gene (2700099C18Rik), mRNA | — |
| 1434534_at | 5.693 | — | — | — |
| 1426048_s_at | 5.603 | Mm.85544 | transcription factor AP-2, alpha | Tcfap2a |
| 1449500_at | 5.535 | Mm.66015 | serine (or cysteine) peptidase inhibitor, clade B, member 7 | Serpinb7 |
| 1430582_at | 5.508 | Mm.133101 | SNF2 histone linker PHD RING helicase | Shprh |
| 1435670_at | 5.464 | Mm.137021 | transcription factor AP-2 beta | Tcfap2b |
| 1422588_at | 5.427 | Mm.358617 | keratin complex 2, basic, gene 6b | Krt2-6b |
| 1445187_at | 5.408 | Mm.329504 | RIKEN cDNA 9430070O13 gene /// gene model 979, (NCBI) | 9430070O13Rik /// Gm979 |
| 1421996_at | 5.28 | Mm.85544 | transcription factor AP-2, alpha | Tcfap2a |
| 1423323_at | 5.278 | Mm.154045 | tumor-associated calcium signal transducer 2 | Tacstd2 |
| 1452228_at | 5.242 | Mm.257819 | RIKEN cDNA 4930451A13 gene | 4930451A13Rik |
| 1449959_x_at | 5.214 | Mm.23784 | small proline rich-like 9 | Sprrl9 |
| 1419731_at | 5.211 | Mm.14098 | cytochrome P450, family 2, subfamily b, polypeptide 19 | Cyp2b19 |
| 1442279_at | 5.14 | Mm.312133 | Enhancer of polycomb homolog 1 (*Drosophila*) (Epc1), transcript variant 1, mRNA | Epc1 |
| 1455408_at | 5.008 | Mm.24880 | RIKEN cDNA 4732472I07 gene | 4732472I07Rik |
| 1416271_at | 4.925 | Mm.28209 | PERP, TP53 apoptosis effector | Perp |
| 1418722_at | 4.888 | Mm.236225 | neutrophilic granule protein | Ngp |
| 1437351_at | 4.809 | Mm.224814 | CXXC finger 4 | Cxxc4 |
| 1440162_x_at | 4.662 | Mm.208144 | hypothetical protein A630043P06 | A630043P06 |
| 1426641_at | 4.647 | Mm.266679 | tribbles homolog 2 (*Drosophila*) | Trib2 |
| 1442349_at | 4.643 | Mm.259334 | RIKEN cDNA C630028N24 gene | C630028N24Rik |
| 1425624_at | 4.593 | Mm.209005 | EPM2A (laforin) interacting protein 1 | Epm2aip1 |
| 1460039_at | 4.577 | Mm.297371 | POU domain, class 3, transcription factor 1 | Pou3f1 |
| 1440523_at | 4.562 | Mm.98096 | retinal short chain dehydrogenase reductase 2 | MGI: 2668443 |
| 1431211_s_at | 4.438 | Mm.180200 | thioesterase superfamily member 5 | Them5 |
| 1447329_at | 4.351 | — | — | — |
| 1443687_x_at | 4.344 | — | — | — |
| 1420988_at | 4.306 | Mm.311585 | polymerase (DNA directed), eta (RAD 30 related) | Polh |
| 1456248_at | 4.189 | Mm.46390 | RIKEN cDNA 2310002A05 gene | 2310002A05Rik |
| 1430000_at | 4.157 | — | RIKEN cDNA B230117O15 gene | B230117O15Rik |
| 1446490_at | 4.154 | Mm.29966 | Polypyrimidine tract binding protein 2, mRNA (cDNA clone MGC: 11671 IMAGE: 3709255) | Ptbp2 |
| 1441909_s_at | 4.1 | Mm.225253 | RIKEN cDNA 9530066K23 gene | 9530066K23Rik |
| 1427747_a_at | 4.035 | Mm.9537 | lipocalin 2 | Lcn2 |
| 1437145_at | 3.994 | Mm.46431 | RIKEN cDNA 2310002J15 gene | 2310002J15Rik ← |
| 1419463_at | 3.985 | Mm.20897 | chloride channel calcium activated 2 | Clca2 |
| 1441440_at | 3.976 | Mm.277366 | autophagy-related 4C (yeast) | Atg4c |
| 1437705_at | 3.854 | — | — | — |
| 1418028_at | 3.846 | Mm.19987 | dopachrome tautomerase | Dct |
| 1442786_s_at | 3.804 | Mm.270469 | DNA segment, Chr 5, Brigham & Women's Genetics 0860 expressed | D5Bwg0860e |

TABLE 3

| | | | |
|---|---|---|---|
| E7733 E12.5 | A | wt/wt | |
| | B | wt/120 | |
| | C | 120/120 | |
| | D | wt/120 | |
| | E | wt/120 | |
| | F | wt/wt | |
| | G | wt/wt | |
| | H | 120/120 | |
| E7734 E12.5 | A | 120/120 | |
| | B | wt/120 | |
| | C | wt/120 | |
| | D | wt/120 | |
| | E | wt/120 | |
| | F | wt/120 | |
| | G | wt/120 | |
| | H | 120/120 | |
| | I | wt/wt | |
| | K | 120/120 | |
| E7232 E14.5 | A | 120/wt | |
| | B | 120/wt | |
| | C | 120/120 | |
| | D | wt/wt | |
| | E | 120/wt | |
| | F | 120/wt | |
| | G | wt/wt | |
| | H | 120/120 | |
| | I | 120/wt | |

TABLE 3-continued

|  |  |  |
|---|---|---|
|  | K | wt/wt |
|  | L | wt/wt |
| E7494 E14.5 | A | 120/120 |
|  | B | wt/wt |
|  | C | 120/wt |
|  | D | 120/wt |
|  | E | 120/120 |
|  | F | 120/wt |
|  | G | 120/wt |
|  | H | 120/wt |
|  | I | wt/wt |
| E7119 E16.5 | A | 120/wt |
|  | B | 120/wt |
|  | C | 120/120 |
|  | D | 120/wt |
|  | E | 120/wt |
|  | F | 120/wt |
|  | G | 120/120 |
|  | H | 120/wt |
|  | I | wt/wt |
|  | J | 120/wt |
|  | K | 120/wt |
|  | L | 120/wt |
| E7477 E16.5 | A | 120/120 |
|  | B | wt/wt |
|  | C | ? |
|  | D | 120/+ |
|  | E | wt/wt |
|  | F | wt/wt |
|  | G | ? |
|  | H | 120/wt |
|  | I | 120/wt |
|  | K | 120/wt |
|  | L | 120/120 |
| E7478 E16.5 | A | 120/120 |
|  | B | wt/wt |
|  | C | 120/wt |
|  | D | 120/wt |
|  | E | 120/wt |
|  | F | 120/120 |
|  | G | wt/wt |
|  | H | 120/wt |
|  | I | 120/wt |
|  | K | wt/wt |
|  | L | 120/120 |
|  | M | wt/wt |

DETAILED DESCRIPTION

Introduction

The R2R genes, transcripts and respective proteins were discovered in a VEGF mouse knockout model. The Vegf120/120 knockout mouse is unable to produce the Vegf$^{164}$ and Vegf$^{188}$ isoforms (Vegf$^{164}$ is the homologue of human VEGF$^{165}$). The lungs of Vegf120/120 knockout mice are hypoplastic at birth and peripheral airway and vascular differentiation becomes severely impaired in Vegf120/120 knockout embryonic lungs. A genomics approach led to the discovery that Vegf$^{164}$ in the mouse and VEGF$^{165}$ in man drive a very specific gene expression program. This program consists of two components. The first component is the (re)generation of basal cells of the airway epithelium: basal cells are the source of at least the cellular population of the proximal airways. The basal cells also generate strong intercelullar connections by building hemidesmosome and focal adhesion connections. The basal cells strengthen their intracellular architecture by the intermediate filament proteins KRT14 and KRT5. These two proteins are glued to the (hemi)desmosome.

The second component is a differentiation program: it's a 'fortification program' ('squamous differentiation') of the cells lining the airways. These cells need to be tough at birth, as they will be exposed to mechanical stress and high levels of oxygen. The fortification is made possible by a family of proteins that strengthen cellular architecture. This family of proteins consists of the intermediate filament group and the proteins that strengthen the intermediate filaments (SPRR proteins, LOR, HRNR, etc). These two programs can be summarized under the headings 'keratinocyte differentiation', 'epidermal cell differentiation', 'intermediate filament reorganization', 'cornified envelope', 'keratinocyte differentiation'. 'cytoskeleton remodeling keratin filaments'.

While it is tempting to use the VEGF$^{165}$ protein for the regeneration of damaged lungs in humans, VEGFA and VEGF$^{165}$ are important regulators of a vast diversity of processes in the organism. Hence, the administration of VEGFA or VEGF$^{165}$ would result in too many side effects.

Two novel genes (R2R$^1$ and R2R$^2$) were discovered in the gene expression program that's driven by Vegf$^{164}$ in the mouse and VEGF$^{165}$ in man. These novel genes, their transcripts and translated proteins are not related to the genes and their downstream products of the basal and squamous gene expression program.

Experiments were undertaken to demonstrate that these genes are important modulators of the basal and squamous differentiation program. One of the most important findings of these experiments is that these genes are important modulators of HIF1α and PERP expression in the cell. In our experiments, the R2R genes are positive regulators and interference with this mechanism opens therapeutic possibilities in cancer therapy.

Material and Methods

Mouse Embryos and Tissue Processing.

All animal experiments were approved by the Animal Ethics Committee of Leiden University Medical Center and performed according to the *Guide for the Care and Use of Laboratory Animals* published by the NIH. Heterozygous Vegf+/120 mice were crossed to obtain Vegf120/120 embryos and Vegf+/+ wild type littermates. The morning of the vaginal plug was defined embryonic day (E) 0.5. Pregnant females were sacrificed by cervical dislocation. E12.5, 14.5 and 16.5 embryos were isolated in sterile PBS. The embryonic thoraces were carefully dissected in Rnase-free conditions, placed in tissue freezing medium (TBS, Triangle Biomedical Sciences, Durham N.C.), frozen and stored at −80° C. The distribution of embryos according to age and maternal origin is represented in Table S1.

Cryostat sections (8 μm) were cut and attached to Super-Frost Plus microscope slides (Menzel Gmbh & Co KG, Braunschweig Germany). Sectioning and further immunohistochemical processing of embryonic thoraces of different ages was performed at random.

Immunohistochemistry and Laser Capture Microdissection.

Three tissue sections from each embryonic thorax were selected at the level of the biventricular view of the heart. These were immunohistochemically processed in one batch. The cryostat sections were fixed by placing the slides in cold acetone (4° C.) during 2 minutes after removal from the −80° C. freezer. All further immunohistochemical steps were performed at 4° C., and all buffers and antibody solutions kept at 4° C. Rnase free PBS or D-PBS buffer was prepared by diluting RNAsecure (25×, AM7006, Ambion Tex.) to 1× in the desired buffer. All antibody solutions were prepared in PBS whereas the isolectin GS-IB$_4$ conjugate was diluted in D-PBS. Superase. In (AM2696, Ambion, Austin, Tex.) was added to each antibody solution in a final concentration of 1 U/μl. The slides were air-dried and the tissue sections circumscribed with a hydrophobic barrier pen. After placing the slides on a cold metal block (4° C.), 30 μl of PBS was applied to each tissue section and drained off. Subsequently, 30 μl of mouse anti-keratin pan (4, 5, 6, 8, 10, 13, 18) monoclonal antibody (MAB1636, Chemicon) in a concentration of 10 μg/100 μl was dripped on the specimen. The antibody solution was drained off after 2 minutes and the tissue section gently rinsed with 250 μl of PBS. Thirty μl of Alexa-fluor-488 chicken anti-mouse IgG (H+L) conjugate (A21200, Invitrogen Calif.) in a concentration of 10 μg/100 μl was then applied for 2 minutes, followed again by a gentle wash with 250 μl of PBS. Finally, a third cycle of 2 minutes staining with 30 μl of isolectin GS-IB$_4$ Alexa Fluor 594 conjugate (121413, Invitrogen, Calif.) in a concentration of 10 μg/100 μl completed the staining procedure. The tissue sections were dehydrated at room temperature: 75% EtOH (30 sec), 95% EtOH (30 sec), 100% EtOH (30 sec), 100% EtOH (120 sec), xylene (180 sec). Laser capture microdissection was performed on a Veritas Microdissection Instrument (Arcturus Bioscience Inc., Mountain View, Calif.) immediately after the dehydration steps. We dissected 3×300 to 400 cells (as triplicate samples) from intrapulmonary airways or blood vessels in the embryonic lungs of three tissue sections at the level of the biventricular view of the heart. Cells staining for mouse anti-keratin pan monoclonal antibody/chicken anti-mouse IgG Alexa-fluor-488 conjugate were identified as green fluorescent cells (blue filter). These green fluorescent cells were defined as airway epithelial cells (ker+ cells) and were randomly dissected, irrespective of their proximal or distal airway morphology. Cells staining for isolectin GS-IB$_4$ Alexa-fluor-594 conjugate were identified as red fluorescent cells (green filter). These cells were defined as mesenchymal cells with endothelial features (il+ cells). Staining of cells for both markers was not observed on the three embryonic time points (E 12.5, 14.5, 16.5). In fact, the green and red fluorescent cells could be observed as a positive/negative image from each other. The microdissected ker+ or il+ cells were collected in a Gene Amp tube (Applied Biosystems, Foster City Calif.) filled with 75 μl of RNeasy lysis buffer (RLT; Qiagen, Hilden, Germany) containing 0.14 M β-mercaptoethanol and 200 ng polyinosinic acid (Sigma).

RNA Isolation, Amplification, Labeling, and Microarray Hybridization.

Laser-captured samples were incubated at 42° C. for 20 minutes and then chilled on ice. Samples were stored at −80° C. until further processing. After thawing, an equal volume of 70% ethanol was added to each sample and then transferred to RNeasy MinElute Spin Columns (Qiagen). RNA was cleaned up according to the manufacturer's instructions, eluted in 14 μl of RNase-free water, and adjusted to 4 μl by vacuum drying. Two rounds of linear mRNA amplification were needed to generate sufficient quantities of cRNA. Two-cycle cDNA synthesis and synthesis of biotin-labeled cRNA was performed according to the GeneChip Eukaryotic Sample and Array Processing Manual (Affymetrix, Santa Clara, Calif.). As "spike-in" controls, the GeneChip Poly-A RNA control kit (Affymetrix) was used. MEGAscript T7 kit (Ambion, Austin, Tex.) was used for in vitro transcription of the second cDNA strand in the first round of amplification, yielding 112 to 457 ng of aRNA. The second round of amplification, starting from 100 ng of first round aRNA, yielded 11 to 86 μg of cRNA using the GeneChip in vitro transcription (IVT) labelling kit. Labeled RNA was hybridized to mouse genome MG-430_2.0 GeneChip arrays (Affymetrix). Hybridization was performed using 12.5 μg of biotin-labeled RNA at 45° C. for 16 hours under continuous rotation. Arrays were stained in Affymetrix Fluidics stations using streptavidin-phycoerythrin (SAPE), followed by staining with anti-streptavidin antibody and a second SAPE staining. Subsequently, arrays were scanned with an Agilent Laserscanner (Affymetrix).

Statistical Analysis.

The Affymetrix probe level data were summarized using FARMS (Factor Analysis for Robust Microarray Summarization)[1]. Raw intensities were $\log_2$ transformed to get data normally distributed. First, an unsupervised multivariate projection method, Spectral Map Analysis[2], was applied to reduce the complexity of highly dimensional data (n genes vs. p samples). Spectral Map Analysis provides an unbiased identification of the predominant clusters of genes and subjects that are present in the data set. Second, tests for differential gene expression between the two cellular origins (ker+ versus il+ cells) was performed in LIMMA (Linear Models for Microarray Data)[3], as this method uses information across genes making the analyses stable even for experiments with small number of arrays[3]. Third, differences between Vegf120/120 knockout and wild type littermates in expression profiles over embryonic age were tested through a two-way interaction of Vegf genotype and time, again using LIMMA[3]. The data of E12.5 and E14.5 were pooled, as we were only interested in the contrasting time profile of E16.5 versus E14.5 and E12.5. This test was performed on the ker+ and il+ samples separately, because these two tissues originated from the same embryos. Models like LIMMA assume that all the samples have been randomly and independently collected. Correction for this dependency would have required too complex models if the ker+ and il+ would have been analysed concurrently. Genomic variation from the single interaction of tissue type (ker+ versus il+ samples) was also uncovered by LIMMA analysis. Allocation of differential expression along the whole genome was performed using MACT (Microarray Chromosome Analysis Tool).

Results/Discussion

At birth, $O_2$ and $CO_2$ need to be exchanged in the lung across a large interface of distal airways and blood vessels. Embryonic lung development in the mouse undergoes a striking shift at E (=post conceptual day) 16.5[1]. At this time, the intertwined airway and vascular trees sprout by multiplying and refining their distal branches. The distal airways or respiratory tubules multiply by subdivision into thin walled sacculi before birth. These sacculi eventually develop into postnatal alveoli[2]. Thin walled airways require flat cells to facilitate gas transport. The phenotypic differentiation to flat airway cells, which occurs around E16.5, is therefore a crucial phase in embryonic lung development. Epithelial cells covering the airways originate from branching foregut endoderm. From E16.5, epithelial cells in the distal airway start to flatten out whereas proximal cell preserve their columnar shape. The most distal of these cells will line the sacculi and alveoli and develop a flat or even squamous morphology by E18.5. The capillaries are lined with flat endothelial cells and represent the distal blood vessels of the vascular tree. Endothelial cells covering pulmonary blood vessels derive from mesodermal mesenchyme. Their growth needs to closely match the growth of their epithelial counterparts in order to provide the large alveolar-capillary interface over which gas exchange initiates at birth. Reciprocal crosstalk between endodermally derived airway epithelium and surrounding mesodermal mesenchyme initiates at early lung morphogenesis[3,4]. Starting at E9.5, Fgf10 produced by mesenchymal cells in surrounding mesoderm is the most important cue for branching endoderm. Close interaction with at least Shh, Bmp, TGF-β, and Wnt signaling factors modulates this early branching mechanism. However, the molecular machinery underpinning the later cellular phenotypical changes and epithelial-endothelial crosstalk at E16.5 is less understood.

In order to gain further insight into late lung differentiation after E12.5, we developed a RNA-friendly immunohistochemical staining protocol for laser capture microdissection of epithelial cells in the developing airway. We reasoned that downstream gene expression profiling of RNA isolated from airway cells sharing a common epithelial antigen at different embryonic ages, should highlight their transcriptional changes over time. This program should at least reflect epithelial features, preferably of the pulmonary airway type. The same assumption was tested on pulmonary cells marked for an endothelial marker universally expressed at different embryonic ages. Additionally, a mouse knockout model with late abnormal pulmonary branching morphogenesis was incorporated in this approach. We chose the Vegfl20/120 model, as peripheral airway and vascular differentiation[5,6,7] becomes severely impaired in these Vegfl20/120 knockout embryonic lungs. Wild type epithelial and endothelial cells were expected to express a set of airway and vascular differentiation genes, lacking in their Vegfl20/120 knockout counterparts. Vegfl20/120 mice lack VEGF-A isoforms 164 and 188, but still express isoform 120. VEGF-A isoforms 164 and 188 (VEGF164 and VEGF188) are more tightly bound to the extracellular matrix than the more soluble VEGF120 variant, and concentrate locally around distal airways. The standard view states that pulmonary epithelial cells secrete these VEGF-A isoforms, whereby VEGF164 and VEGF188 encourage local growth of pulmonary endothelial cells through stimulation of receptor tyrosine kinases Flk1 (VEGF receptor-2) and Flt1 (VEGF receptor-1). Confined expansion of endothelial cells refines the pulmonary vascular tree and allows a matching growth of epithelial cells[8,9]. This epithelial-endothelial crosstalk permits gas exchange at birth by the formation of a close bond between the alveoli of the distal airways and the capillaries of the lung vasculature. However, this type of interaction cannot explain the presence of VEGF-A in mesenchymal cells surrounding the distal airway epithelial cells.

Immunohistochemical staining was performed on frozen tissue sections cut from embryonic thoraces isolated at E12.5, E14.5 and E16.5 (FIGS. 2A-2G). The genomic distribution of the embryos is shown in Table S1. We selected antibodies exhibiting sufficient bandwidth for binding epithelial or endothelial antigens in the embryonic time frame of our study. Anti-cytokeratin (directed against cytokeratin 4, 5, 6, 8, 10, 13, and 18) was chosen for labelling of epithelial cells (ker+ cells) lining the airways, as primitive and differentiated epithelial cells globally express intermediate filaments of different keratins. Endothelial cells in the same tissue section were stained with isolectin GS-IB$_4$ (*Griffonia simplicifolia*) Alexa-fluor-594 conjugate, which binds early[10] and late endothelial cells[11,12] in the mouse (il+ cells). Staining of cells for both immunohistochemical markers was not observed on the three embryonic time points. Three hundred to four hundred ker+ and il+ cells were selectively isolated by laser capture microdissection. Two rounds of linear mRNA amplification yielded sufficient cRNA for hybridization to Affymetrix Mouse 430_2.0 Genechips.

Figure 1:
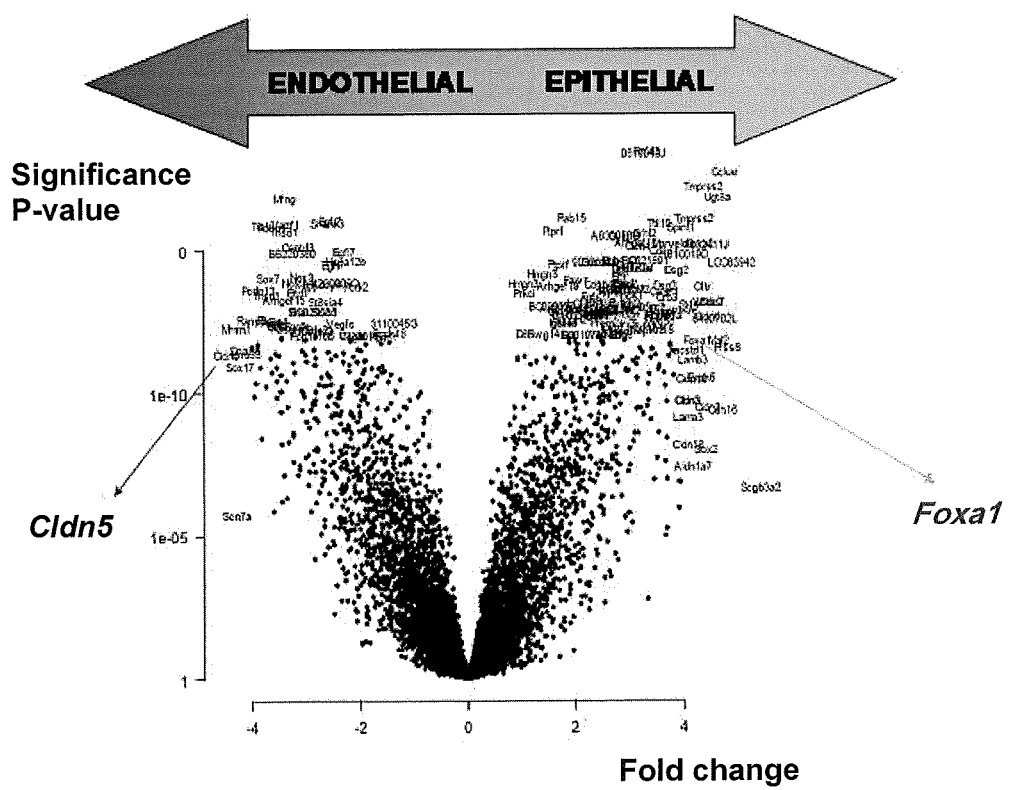
FIG. 1: Comparison of endothelial and epithelial cells from Vegf+/+ at E16.5. Volcanoplot showing on the y-axis the significance of each gene when testing for the effect of cellular origin (based on LIMMA). The x-axis shows the fold change when comparing the 2 tissues. Ker+ cells express archetypical epithelial genes, while il+ cells transcribe representative endothelial genes. Endothelial Cldn5 and epithelial Foxa1 are highlighted because both were also present as top genes in the Y-axis (PC$_2$) of the unsupervised spectral map analysis (see FIG. 3).
Figures 2A, 2B, 2C, 2D, 2E, 2F, 2G:
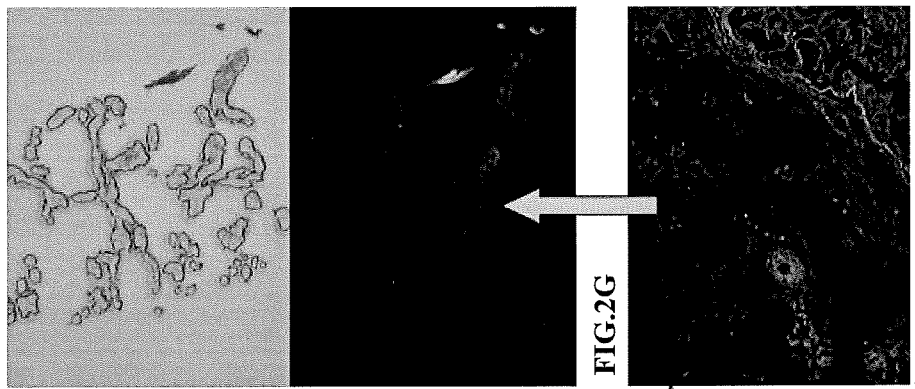
FIGS. 2A-2G: Schematic representation of the laser capture microdissection process. Embryonic thoraces (FIG. 2A) were cut in 8 mm sections and placed on slides (FIG. 2B). Double immunohistochemical staining on these tissue sections (FIG. 2C) with anti-'pan' keratin and GS-IB4 isolectin separated pulmonary airway cells with epithelial (FIG. 2D) distinctiveness from the surrounding cells with endothelial (FIG. 2E) characteristics. Specific cell groups isolated by laser capture microdissection are shown in FIG. 2F and FIG. 2G. (L=lung, H=heart).
Figure 3:
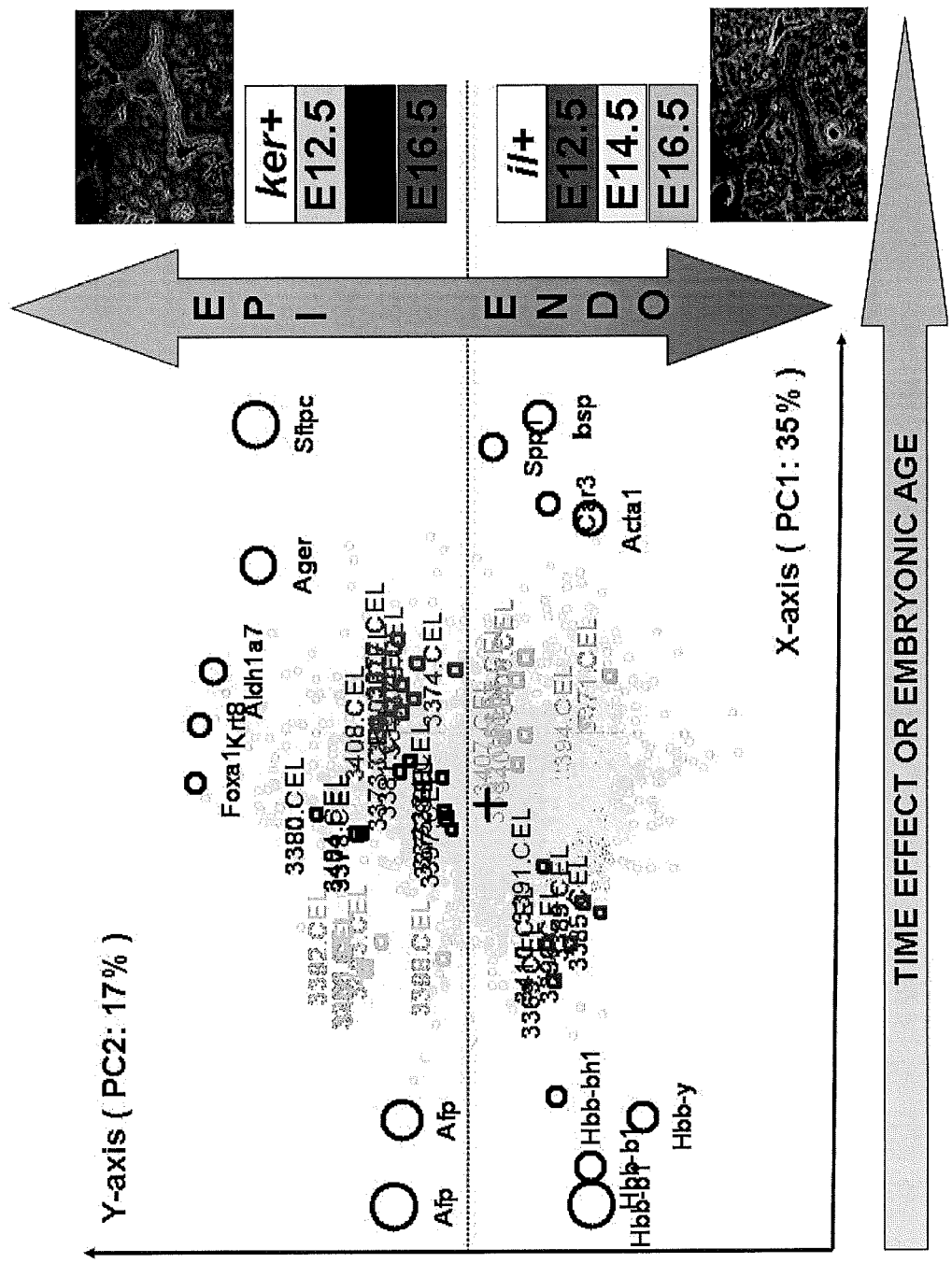
FIG. 3: Spectral map analysis with first principal component (PC1 on X-axis) and second principal component (PC2 on Y-axis). Time effect or embryonic age was uncovered in PC1 (accountable for 35% of the variation in the data set). Gene probes of genes expressed later in embryonic life as Sftpc were located further on the X-axis. Difference in cellular origin (il+ versus ker+ cells) was found in PC2. Gene probes of epithelial genes ('EPI') were located further on the Y-axis in contrast to gene probes of endothelial gene ('ENDO') families. The different sample groups were separated in the spectral map along PC1 (embryonic age) and PC2 (cellular origin). Ker+ samples gathered on the epithelial side of the Y-axis, and il+ samples grouped on the endothelial side. The samples also distributed along the X-axis according to their embryonic age. Samples of later embryonic days were located further on the X-axis. The panel below shows 3 expression profiles: (1) showing the difference between epithelial and endothelial cells for Foxa1 expression, (2) showing the effect of embryonic age for Afp expression and (3) showing the genotype dependent profile over embryonic age for Hmr expression.

First, we examined if downstream gene expression profiling was reflecting differentiation with respect to embryonic age and epithelial versus endothelial origin. Exploratory, unsupervised analysis of gene expression data revealed that gene expression changes during embryonic development accounted for the largest variation (35%) in the data set. This variation was graphically well represented in the first principal component (X-axis or $PC_1$) of a spectral map[13] (FIG. 3). Genes displaying the strongest expression changes over the three embryonic stages lie at the extremes of the X-axis. One of these genes, surfactant associated protein C (Sftpc), is known to have an important physiological upregulation during embryogenesis, and sufficient amounts of its protein product are necessary for normal breathing at birth[14,15]. The second principal component (Y-axis or $PC_2$), explaining another 17% of the variation in the dataset, could be assigned to gene expression differences in cellular origin. Some of the most extreme probe sets on the $PC_2$ axis represent genes that are known to be highly characteristic for either pulmonary epithelium or endothelium. Among the eight most extreme probe sets, we identified CD 93 antigen (CD93)[16] and claudin 5 (Cldn5)[17] as illustrative endothelial genes, and on the opposite side of the Y-axis, forkhead box A1 (Foxa1)[18] and keratin 8 (Krt8)[19] as expressive epithelial genes. Superposition of the different samples on the spectral map showed their distribution along the first two principal components. The ker+ and il+ groups were clearly separated according to their cellular origin along $PC_2$ (FIG. 3). Ker+ samples grouped towards epithelial type genes and il+ samples assembled towards endothelial type genes. Both cellular origins gathered together on $PC_1$ at the same embryonic ages. This indicates that the overall developmental gene expression changes are similar for epithelial (ker+) and endothelial (il+) cells. As a whole, the samples cluster together with respect to cellular origin (ker+ versus il+ cells) and embryonic age when applying an unsupervised data-driven analysis. The spectral map analysis underscores that selective laser capture microdissection revealed a good resolution of gene expression profiles. An independent supervised univariate (gene-by-gene) analysis of the effect of tissue origin of the samples (ker+ versus il+) further confirmed that ker+ and il+ cells corresponded at the genomic level with epithelial or endothelial cells, respectively (FIG. 1).

Next, the transcriptional profile associated with abnormal branching morphogenesis in the Vegfl20/120 knockout phenotype was charted in il+ and ker+ cells. For every gene, we tested whether its expression profile over embryonic age differed significantly between Vegfl20/120 knockout and wild type (Vegf+/+) littermates. This difference in age dependent expression profile between Vegf+/+ and Vegfl20/120 unfolded a genomic roadmap in three directions. There were several genes identified with only in the Vegf+/+ genotype a clear upregulation over embryonic age, e.g. Hmr (FIGS. 2A-2G). The Vegfl20/120 genotype showed an impairment in that age dependent induction.

Figures 4A, 4B, 4C:
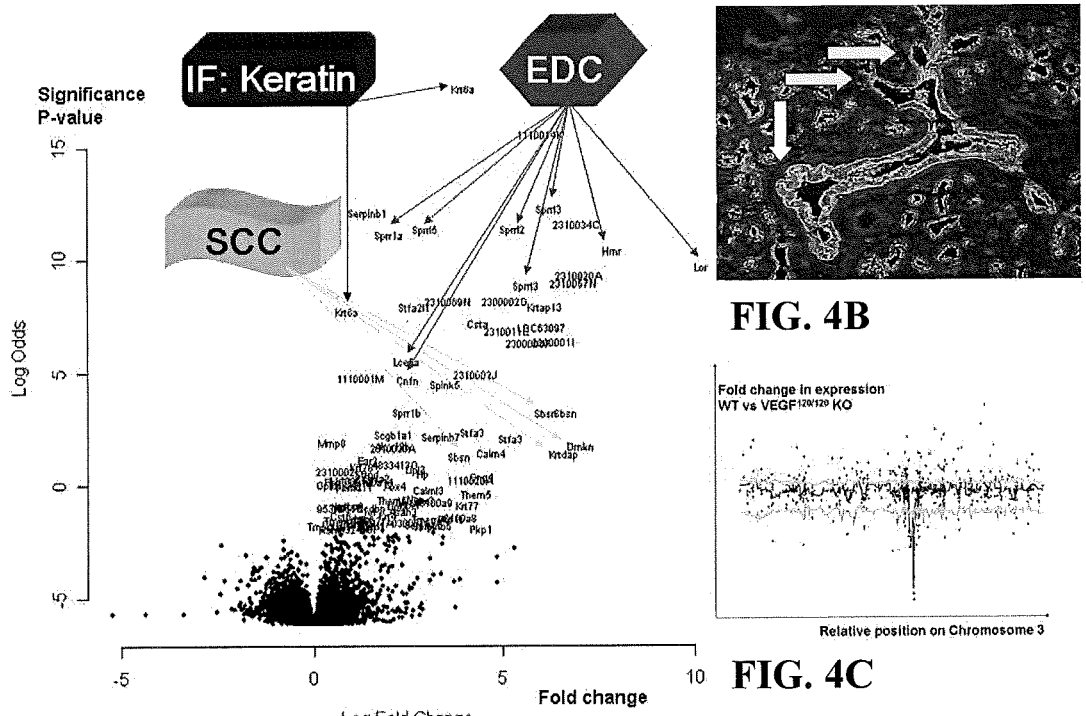
FIGS. 4A-4C: Comparison of epithelial cells from Vegf+/+ and Vegf120/120 genotypes.

First, the cause of the structural deficit in the airways of Vegfl20/120 knockout lungs became apparent. Wild type ker+ cells highly expressed a surplus of 44 epithelial-specific genes on E16.5 compared to their Vegfl20/120 knockout counterparts. A group of genes of the Epidermal Differentiation Complex (EDC) dominated the expression profile (FIGS. 4A-4C). S100a8 and S100a9 figured among this EDC subset and are known to be VEGF-A responsive[20] chemoattractants. Other elements of the EDC such as small proline rich region (Sprr) genes and late constituents of the epidermal cornified envelope were also present. Cytoskeletal keratin Krt2-6 was co-expressed with this EDC subset in wild type ker+ cells on E16.5. Serine-cysteine proteinase inhibitors and the three genes of the SCC (stratified epithelium-secreted protein gene) complex completed the cohort of upregulated genes (FIGS. 4A-4C).

Figure 5A:
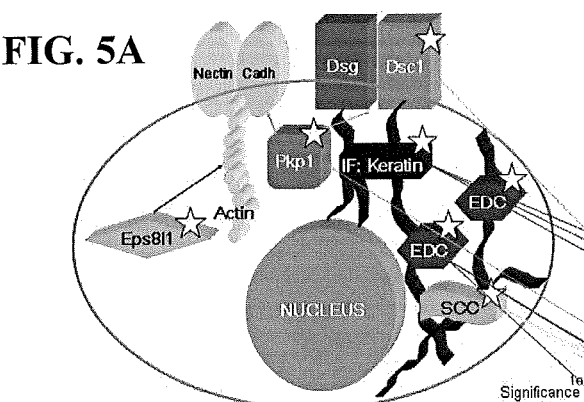
FIGS. 5A-5C.
Figure 5C:
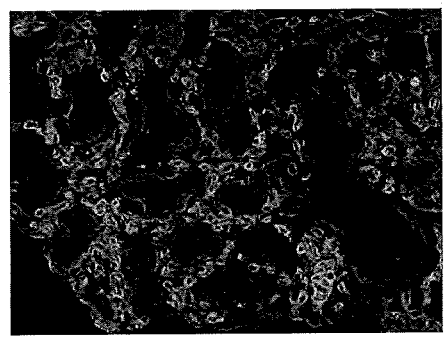
Figure 5B:
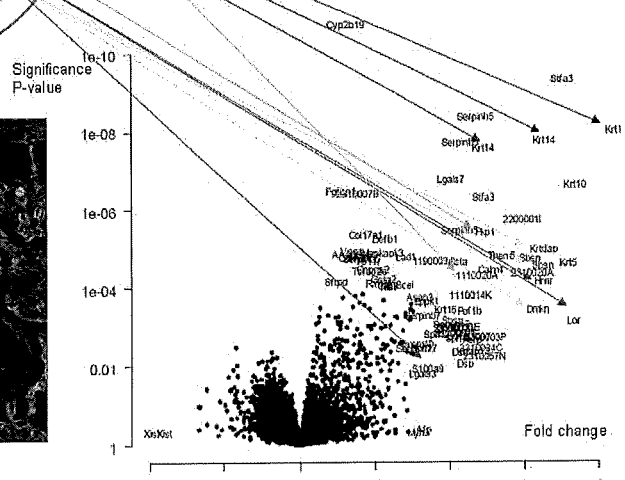

Study of the interaction between embryonic age and genotype in wild type il+ cells uncovered again a profound upregulation of a limited set of genes on E16.5. This response led towards adoption of an epithelial-specific transformation program in wild type il+ cells on E16.5 compared to Vegf120/120 knockout cells. As in wild type ker+ cells, the EDC cluster, the SCC cluster, the cysteine proteinase inhibitors and exclusive keratin genes were clearly upregulated over embryonic age. Riken1110020A410, corresponding to the Dsc1 gene, was highly upregulated in wild type il+ cells on E16.5. Furthermore, Pkp1 (plakophilin 1) displayed an identical transcriptional profile on E16.5 (FIGS. 5A-5C). A highly logical pattern appeared to drive the clustered upregulation of these genes. Keratins are intermediate filament proteins lending structural strength to the cell, most typically in epithelial cells[21]. Proteins encoded by the EDC and SCC cluster, and serine-cysteine proteinase inhibitors fortify this keratin network. Dsc1 (desmocollin 1) codes for one of the proteins shaping the desmosomes[22,23]. Intermediate keratin filaments are linked to intercellular desmosomes that form the cell junction together with gap and adherens junctions. The protein encoded by Pkp1 is most of all a positive regulator of desmosomal protein content[24,25] and is a constituent of the desmosomal complex itself. Pkp1 also links intermediate keratin filaments to the cadherin proteins of the adherens junctions. These results identify receptor tyrosine kinase stimulation by VEGF-A isoforms 164 and 188 as a master switch in the assembly of the desmosomal/intermediate filament machinery in the lung. This mechanism adds another building block to the cytoskeletal and intercellular architecture on top of the Wnt/β-catenin-dependent adherens junction (E-cadherin). In fact, the upregulation of Eps8l1 on E16.5 in wild type il+ cells revealed even direct interference with actin, a key structural protein unrelated to the intermediate filament system. The coordinated and clustered expression of these cytoskeletal and desmosomal genes permits shaping of flat or squamous cellular arrangements in distal airways.

Second, aside from activation of genes coding for specific structural proteins, an intriguing finding was the upregulation of Mapkapk3 in wild type il+ cells on E16.5. Mapkapk3 integrates ERK and p38 signaling[26] pathways in stress and mitogen responses such as VEGF-A stimulation of the endothelial cell. Cdkn2b (p15$^{ink4b}$ or Ink4b), part of the Ink4b-ARF-Ink4a tumor suppressor locus, was simultaneously upregulated. Substantial evidence points to suppression of this locus by associated polycomb group (Pcg) repressor complexes. Derepression of the locus occurs upon dissociation of Pcg complexes by activation or overexpression of Mapkapk3[27]. This brake pedal in the cell cycle allows differentiation during proliferative stimuli[28] and was demonstrated here for the first time in vivo. In effect, cell cycle arrest permitting epithelial transformation of il+ cells is VEGF164- and VEGF188-dependent in the lung. Intriguingly, upregulation of Krt5, Krt14 and Tcfap2c was strikingly similar to the expression fingerprint of the basal cell progenitor in airway epithelium[29]. The basal cell phenotype only appears at birth in the pulmonary airway epithelium and typically binds isolectin. On the other hand, Krt1, EDC and SCC cluster gene expression is a squamous differentiation program. The protein ΔNp63 and TAap63 drive the keratin progenitor and squamous differentiation program respectively. The Trp63 gene coding for these two proteins was upregulated in the wild type il+ cells. As mentioned, staining of cells for both anti-cytokeratin (anti-4, 5, 6, 8, 10, 13, and 18) and isolectin GS-IB$_4$ was not observed at the time points studied. The lack of Krt1 and Krt14 binding by the anti-cytokeratin antibody, allowed therefore the identification of the specific epithelial transformation program of wild type il+ cells at E16.5. It seems unlikely that ker+ epithelial cells generate this epithelial transcriptional program. This would require losing the binding capacity for the anti-cytokeratin antibody in order to escape ker+ labeling. At the same time, the ker+ cells would have to acquire exclusive isolectin GS-IB4 staining. As a result, we propose that pulmonary i/+ cells harbor a reservoir of cells growing into epithelial maturity at E16.5. In other words, pulmonary mesenchymal il+ cells encompass cells with endothelial and epithelial competence.

Figure 6:
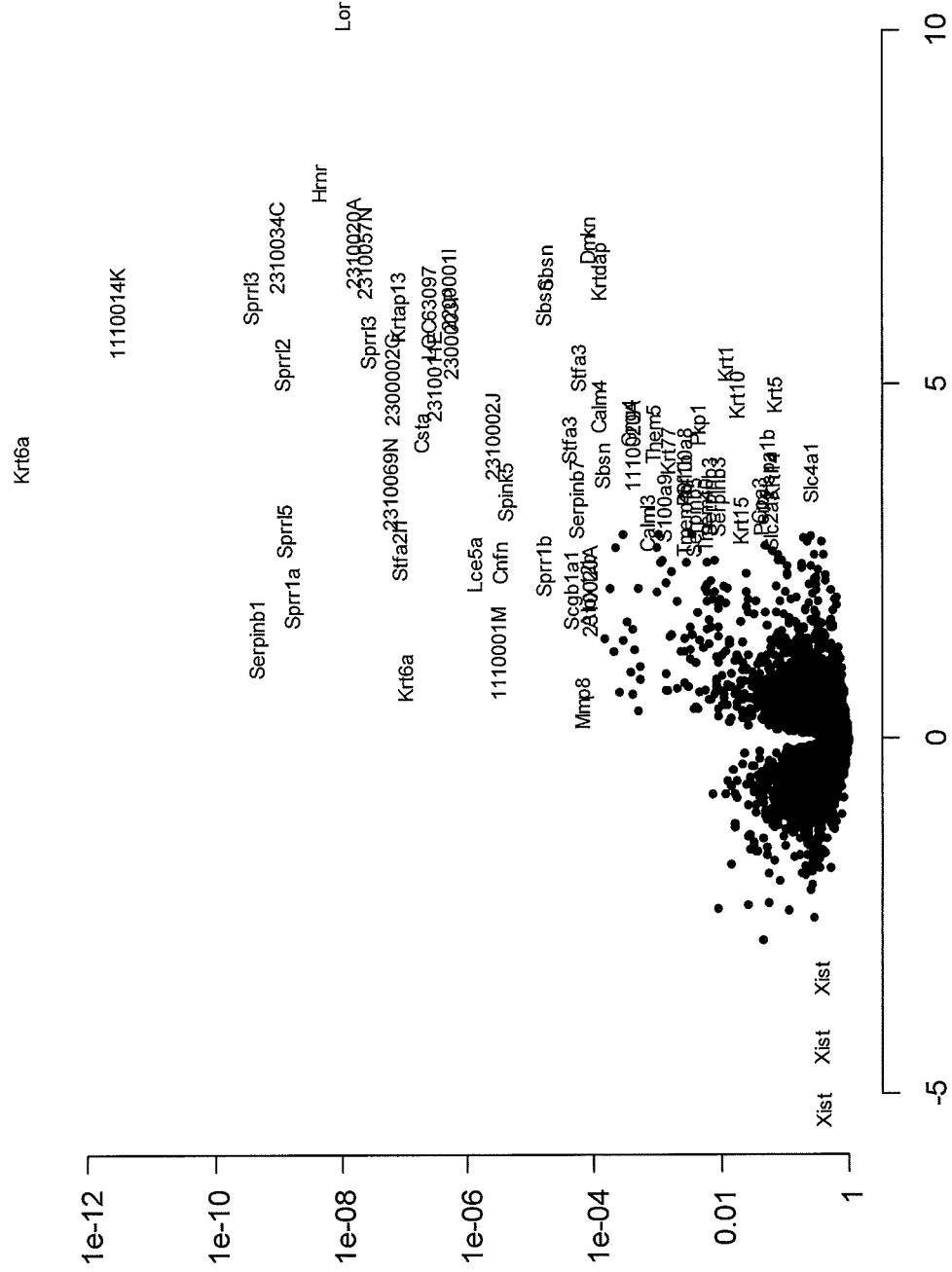
FIG. 6: Volcanoplot based on LIMMA analysis of the group of anti-cytokeratin 4-5-6-8-10-13-18 staining cells. (Linear Models for Microarray Data: differences between Vegf120/120 knockout and wild type littermates in expression profiles over embryonic age were tested through a two-way interaction of Vegf genotype and time). The RIKEN cDNA 2200001115 gene and RIKEN cDNA 2310002J15 gene are highlighted.
Figure 7:
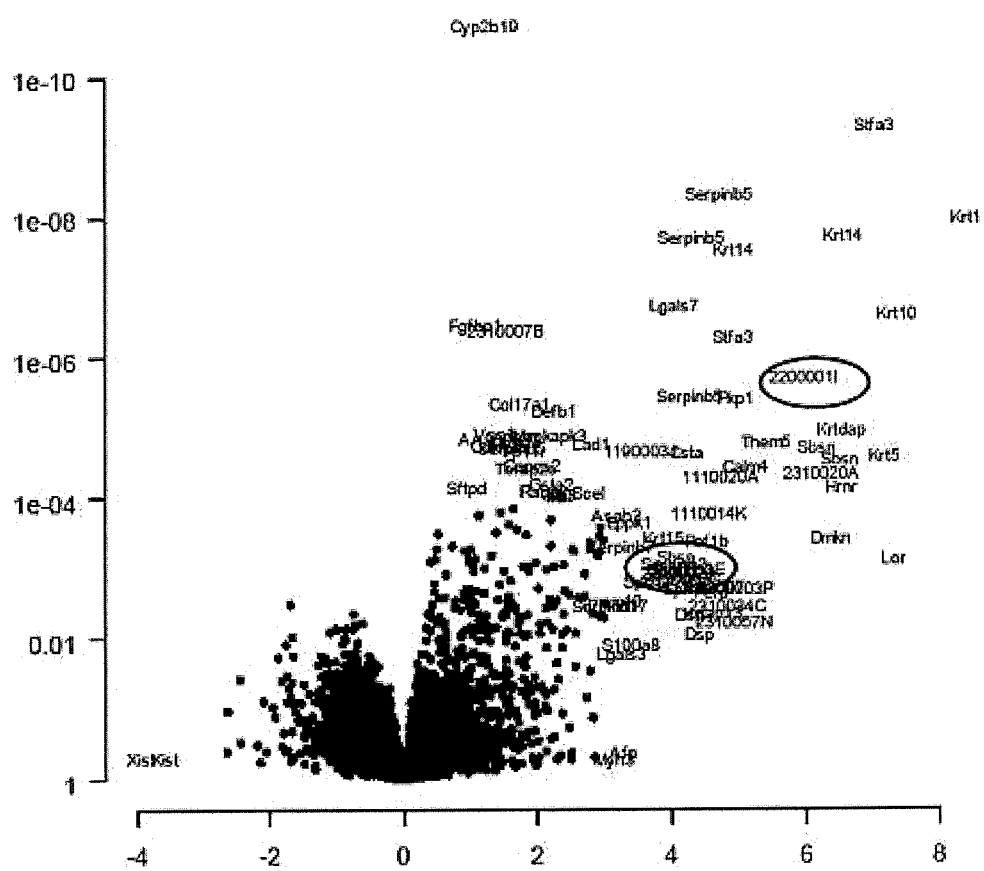
FIG. 7. Volcanoplot based on LIMMA analysis of the group of GS-IB4 binding cells. (Linear Models for Microarray Data: differences between Vegf120/120 knockout and wild type littermates in expression profiles over embryonic age were tested through a two-way interaction of Vegf genotype and time). The RIKEN cDNA 2200001115 gene and RIKEN cDNA 2310002J15 gene are highlighted.

Third, the gene represented by Affymetric probe 1437019_at (RIKEN cDNA 2200001115 gene) and the gene represented by Affymetrix probe 1437145_s_at (RIKEN cDNA 2310002J15 gene) were both upregulated on E16.5 in wild type anti-cytokeratin 4-5-6-8-10-13-18 staining epithelial cells and wild type GS-IB4 binding cells. We found these two genes (lacking biological annotation) to be tightly co-expressed with the squamous and basal cell transcriptional program. They play an important role in production and regeneration of differentiated airway cells (FIG. 6, FIG. 7, Table 1, Table 2). Starting from the longest contig constructed from sequenced clones, we discovered the human homologue of the RIKEN cDNA 2200001115 gene transcript (FIG. 8) and RIKEN cDNA 2310002J15 gene transcript (FIG. 10). Furthermore, protein sequence alignments confirmed the existence of a human homologous protein for the respective translated protein of the RIKEN cDNA 2200001115 gene (FIG. 9) and RIKEN cDNA 2310002J15 gene (FIG. 11). We suggest the name R2R' for the mammalian homologues of the RIKEN cDNA 2200001115 gene, transcript and protein, and R2R$^2$ for RIKEN cDNA 2310002J15 gene, transcript and protein as these genes and their protein products are responsible for regenerative function in the respiratory system.

Fourth, we found that VEGF-A is expressed in ker+ and il+ cells, independent of wild type or Vegf120/120 knockout status. Moreover, the gene coding for VEGF receptor 1 (Flk-1 or Kdr) was abundantly expressed in il+ cells, but also increased significantly as early as E14.5 in ker+ cells. This pattern of VEGF-A and VEGF receptor expression challenges the classic viewpoint of mesenchyme passively waiting for a VEGF-A stimulus from pulmonary epithelium. It coincides essentially with recent work demonstrating the need of endogenous VEGF-A expression and autocrine signaling in survival of endothelial cells[30,31]. From the genomic footprint of wild type versus Vegf120/120 knockout il+ cells, it became also apparent that the il+ cells are the ones responsible for sending epithelial transformation stimuli. Upregulation of Fgfbp1, Lgals7, Lgals3 and Il18 in wild type il+ cells on E16.5 represented these stimuli. The upregulation of the gene encoding fibroblast growth factor-binding protein 1 (Fgfbp1) indicates that primordial FGF-controlled lung budding is also at work in the final stages of lung differentiation. Fgfbp1 acts by concentrating FGF2 and is a fine modulator of growth and differentiation of epithelial tissues in response to FGF stimuli from mesenchyme. The FGF receptor 2 gene (Fgfr2) was in this respect richly expressed in the ker+ and il+ compartment.

In summary, selective laser capture microdissection of cells sharing a specific marker at different embryonic ages was performed. This allowed differentiation of gene expression profiles with respect to embryonic age, cellular origin and Vegf genotype. The transcriptional program revealed by this approach highlighted the importance of the intermediate filament and desmosomal network in the refinement of pulmonary architecture. This mechanism adds another building block to the cytoskeletal and intercellular architecture on top of the Wnt/β-catenin-dependent adherens junction (E-cadherin). Intermediate filaments provide the necessary strength to cells that will be exposed to vast amounts of mechanical and oxidant stress. Not surprisingly, pulmonary cells adopt the same defensive genomic program as skin cells, which are exposed to the same challenges. In parallel with cytoskeletal sophistication, the basal cell progenitor program is acquired by il+ cells late in embryonic life, and is VEGF164-188-dependent.

We have demonstrated that downregulation of FAM25 family and downregulation of C9orf169 gene expression lowers KRT14 expression. Further, we know that expression of the FAM25 family (the human $R2R^1$ homologue) and C9orf169 (the human $R2R^2$ homologue) is upregulated by VEGFA/VEGF$^{165}$. How do these genes act in the VEGFA/VEGF$^{165}$ pathway? siRNA mediated knockdown of the R2R homologues can be used to uncover the specific role of the R2R homologues in the pathway. Indeed the R2R homologues' role is to modulate the VEGFA/VEGF$^{165}$ response in the cell. The basal expression of VEGFA and the VEGF$^{165}$ isoform is high in the pulmonary epithelium. Epithelial functions and structures are far more complex than their endothelial counterparts. Therefore, the typical VEGFA/VEGF$^{165}$ effects of 'grow and multiply' in the endothelium need to be more refined in the endothelium. How is this realized? Expression R2R homologues leads to simultaneous modulation of HIF1A signaling (conferring oxygen tolerance), AND modulation of a specific (PERP) anti-apoptotic pathway. This will permit the (re)generation of strong epithelial cells (with a major defense barrier against stress), without the installment of unlimited growth potential. In other words, the modulation of a specific anti-apoptotic pathway is not a 'permit' for general tolerance to apoptosis. General tolerance to apoptosis would lead to the dangerous situation of immortalization of the cell: the cell develops into a cancer cell.

This study sheds new light on certain human lung diseases. In preterm neonates, late embryonic pulmonary development is disrupted when the infant is prematurely delivered. Insufficient levels of surfactant protein in pulmonary alveoli lead to severe respiratory distress in a large group of premature infants. Instillation of surfactant in the neonatal lung has aided the prevention and treatment of respiratory failure in premature infants. However, high oxygen levels and tensile stress-forces of mechanical ventilation still lead to chronic lung damage or bronchopulmonary dysplasia (BPD). Accelerating squamous differentiation in distal airways of premature infants may prevent this debilitating condition. The intermediate filament network and synchronized replenishment of the basal cell pool may also be of paramount importance in the search for a cure of certain adult lung diseases. Adoption of a squamous phenotype with expression of some EDC cluster genes characterizes squamous metaplasia in the airways of adults with chronic obstructive pulmonary disease (COPD). This defense mechanism against noxious stimuli is however accompanied with loss of regenerative basal cells[32]. In contrast, the embryo succeeds in developing a squamous differentiation program while simultaneously building a basal cell reservoir by a well-defined roadmap. This roadmap serves as a guide in pharmacological intervention in the intermediate filament or basal cell transcriptional machinery. It also points to transformed il+ cells as a source for pulmonary epithelial cells.

Functional Characteristics of $R2R^1$ and $R2R^2$

The VEGF-A (mouse isoform VEGF164=isoform VEGF$^{165}$) dependent expression of the intermediate filament group of genes has been confirmed in the mouse embryo. Expression of these intermediate filament genes leads to differentiation of pulmonary epithelial cells and development of the basal cell program in pulmonary mesenchymal cells.

Furthermore, VEGF-A (mouse isoform VEGF$^{164}$=isoform VEGF$^{165}$) dependent expression of intermediate filament genes has also been confirmed in adult human primary epithelial cells. Stimulation of these cells by VEGF-A isoform VEGF$^{165}$ leads to upregulation of intermediate filament gene expression. Intermediate filament gene expression in these cells is downregulated by isoform VEGF$^{165}$ specific siRNA's. In summary, the expression of intermediate filament genes serves as a paradigm of airway differentiation and regeneration. $R2R^1$ and $R2R^2$ play a specific role in this expression program.

$R2R^1$

The expression of $R2R^1$ is VEGF-A (mouse isoform VEGF$^{164}$=human isoform VEGF$^{165}$) dependent in the mouse. Mesenchymal cells of the lung (GS-IB4 positive staining cells) acquire a basal epithelial cell gene expression program. The expression of $R2R^1$ is essential for mesenchymal to epithelial transition (MET).

Figure 12:
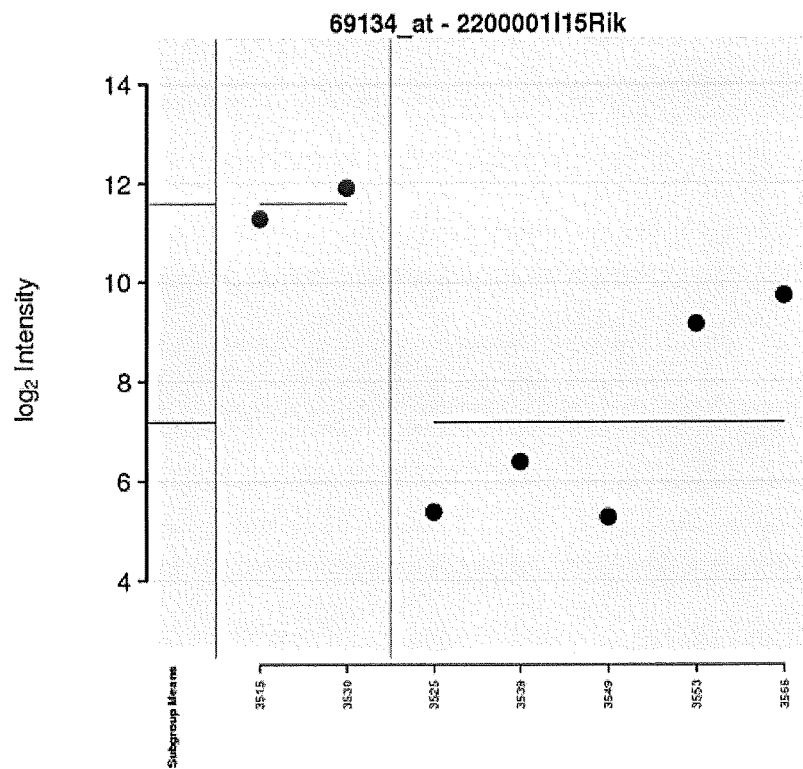
FIG. 12: VEGF-A ($VEGF^{164}$ dependent upregulation of $R2R^1$ in the developing ventricular septum of the mouse embryo. Red=wild type, blue=$VEGF^{120/120}$ knockout mouse, lacking the $VEGF^{164}$ isoform.

The role of $R2R^1$ in MET has now been confirmed in embryonic tissue other than the lung: completion of the ventricular septum of the heart is accomplished by MET. In the mouse, $R2R^1$ is highly expressed in the developing ventricular septum and is VEGF-A (mouse isoform VEGF$^{164}$=human isoform VEGF$^{165}$) dependent. Contrary, $R2R^1$ expression is not found in the developing right ventricular outflow tract: development of this structure is known to be MET independent (see FIG. 12)

$R2R^1$ is a candidate gene in mouse and human for mesenchymal to epithelial transition: the expression of this gene transduces the VEGF-A (mouse isoform VEGF$^{164}$=human isoform VEGF$^{165}$) effect on MET. The reverse process of MET is EMT (epithelial to mesenchymal transition). EMT is an essential part of cancer progression and metastasis. $R2R^1$ may therefore play an important role in cancer biology and therapy.

Furthermore, in silico analysis revealed that the protein product of $R2R^1$ likely interacts with the ribosome. Aside from the scientific impact, the interaction of the $R2R^1$ protein structure with the ribosome has implications for drug development in the field of cancer biology and MET.

Figure 13:
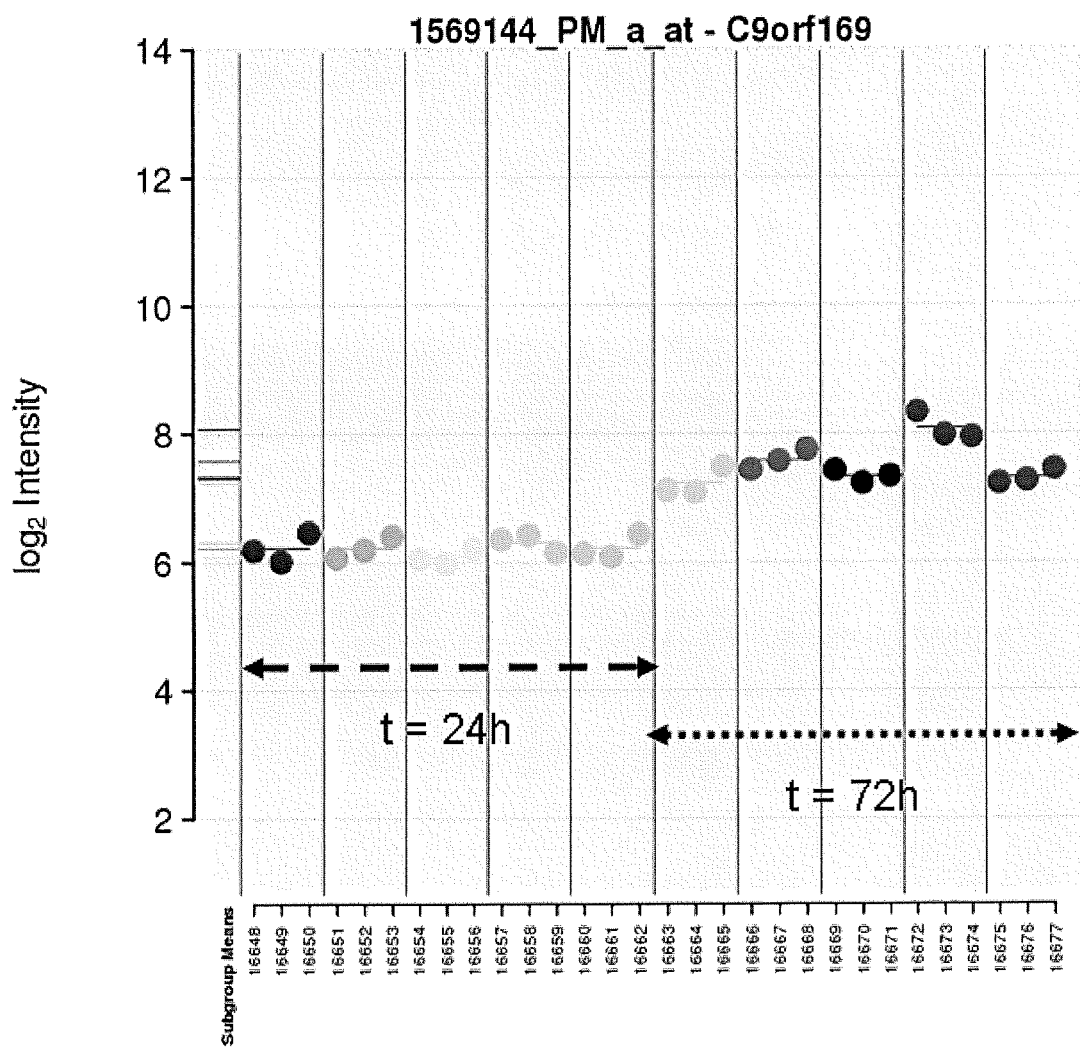
FIG. 13: Human $R2R^2$ homologue (=C9orf196) expression over time (24-72 h) in human adult primary lung epithelial cells.
Figure 14A:
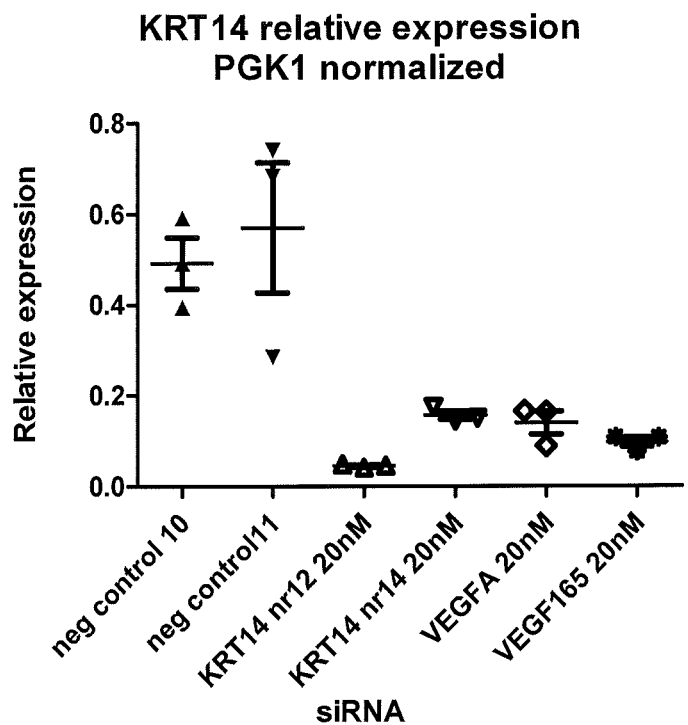
FIGS. 14A-14C: siRNA knockdown of $VEGF^{165}$ leads to knockdown of the genes responsible for the basal cell program and squamous differentiation program. siRNA knockdown in human Primary Bronchial Epithelial Cells (PBEC's) reliably models the effect of gene knockdown of genes of interest.
Figure 14B:
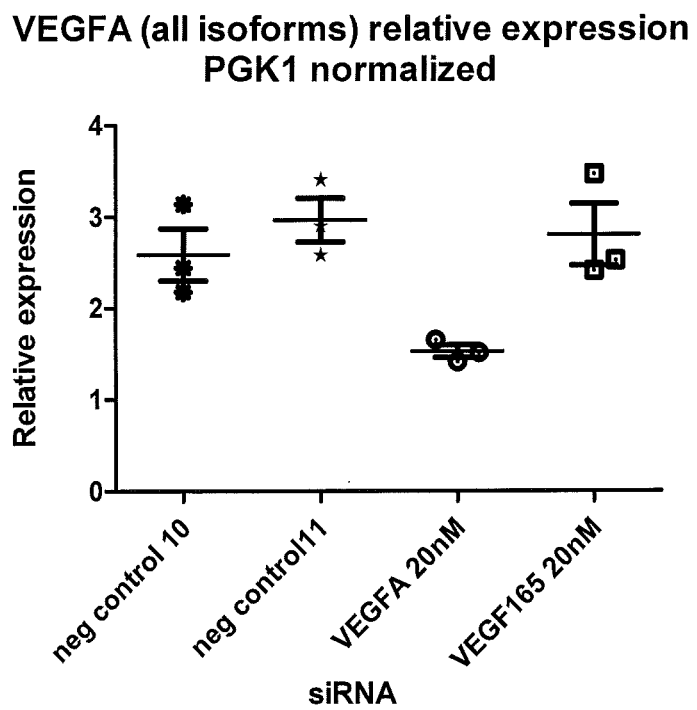
Figure 14C:
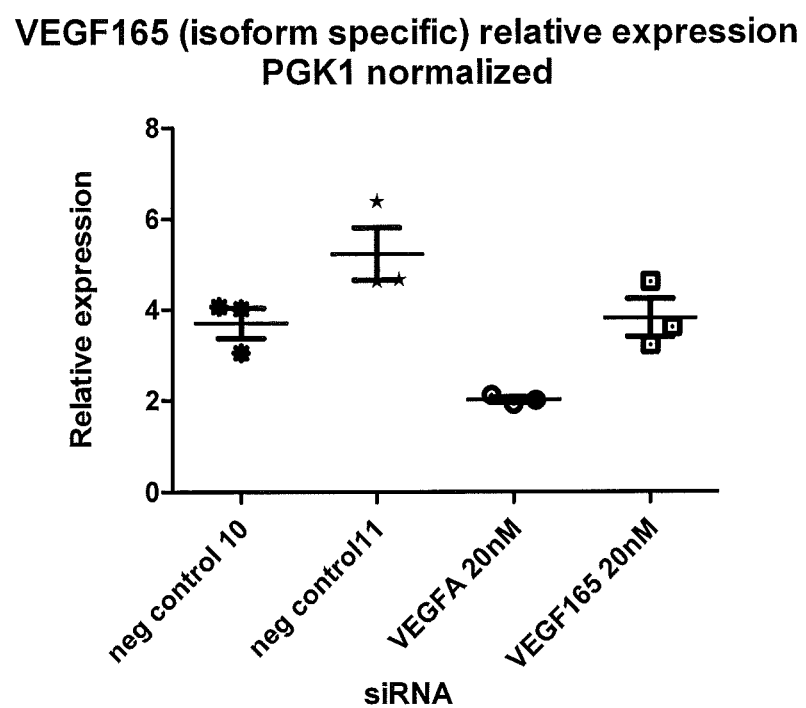
Figure 15A:
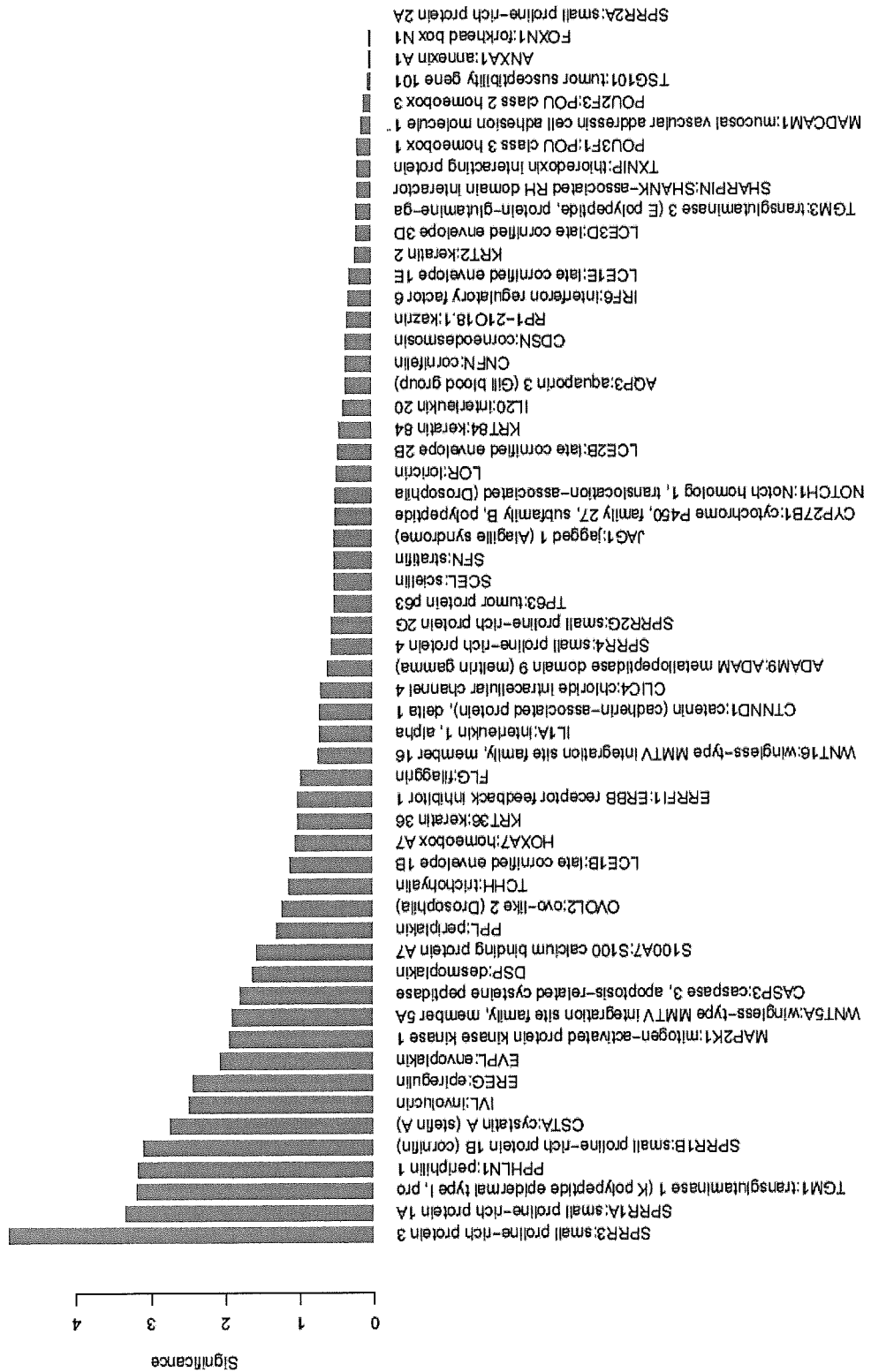
FIGS. 15A-15J: Global gene expression changes brought about by siRNA mediated knockdown of VEGFA in PBEC's. Changes in global gene expression match exactly the changes observed in the Vegf120/120 knockout mouse.
Figure 15B:
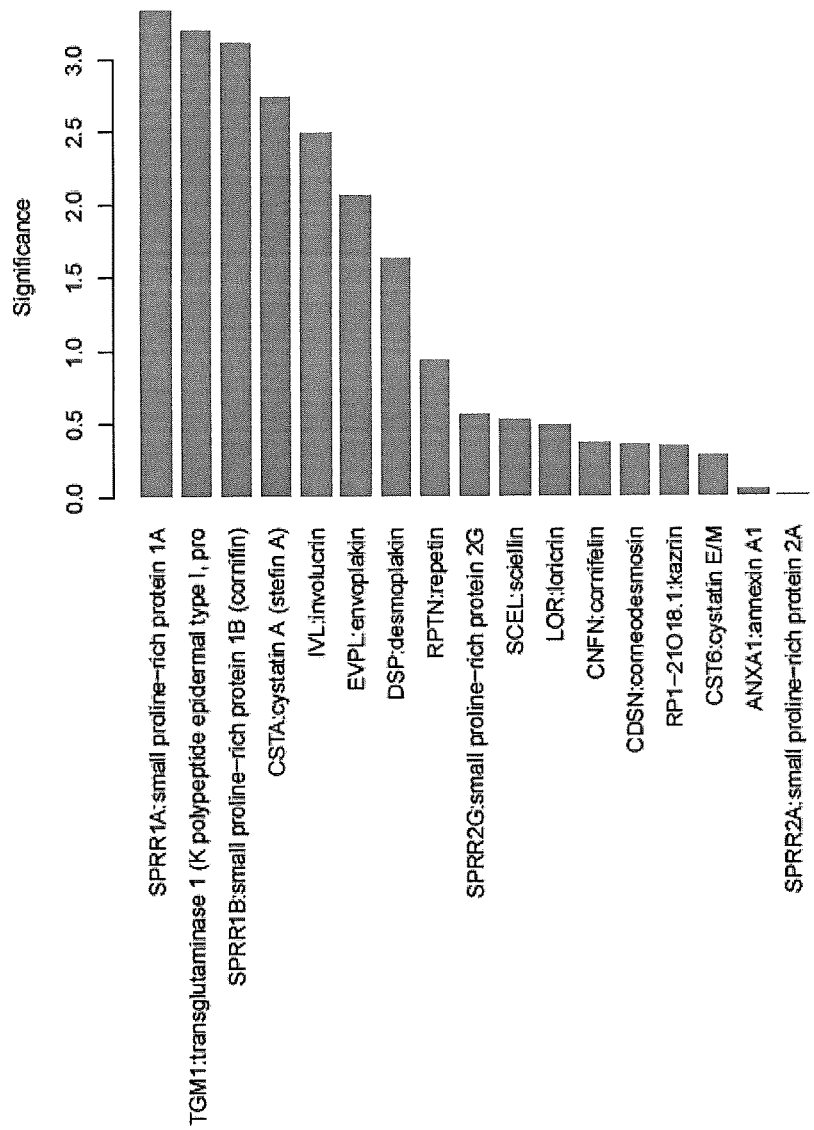
Figure 15C:
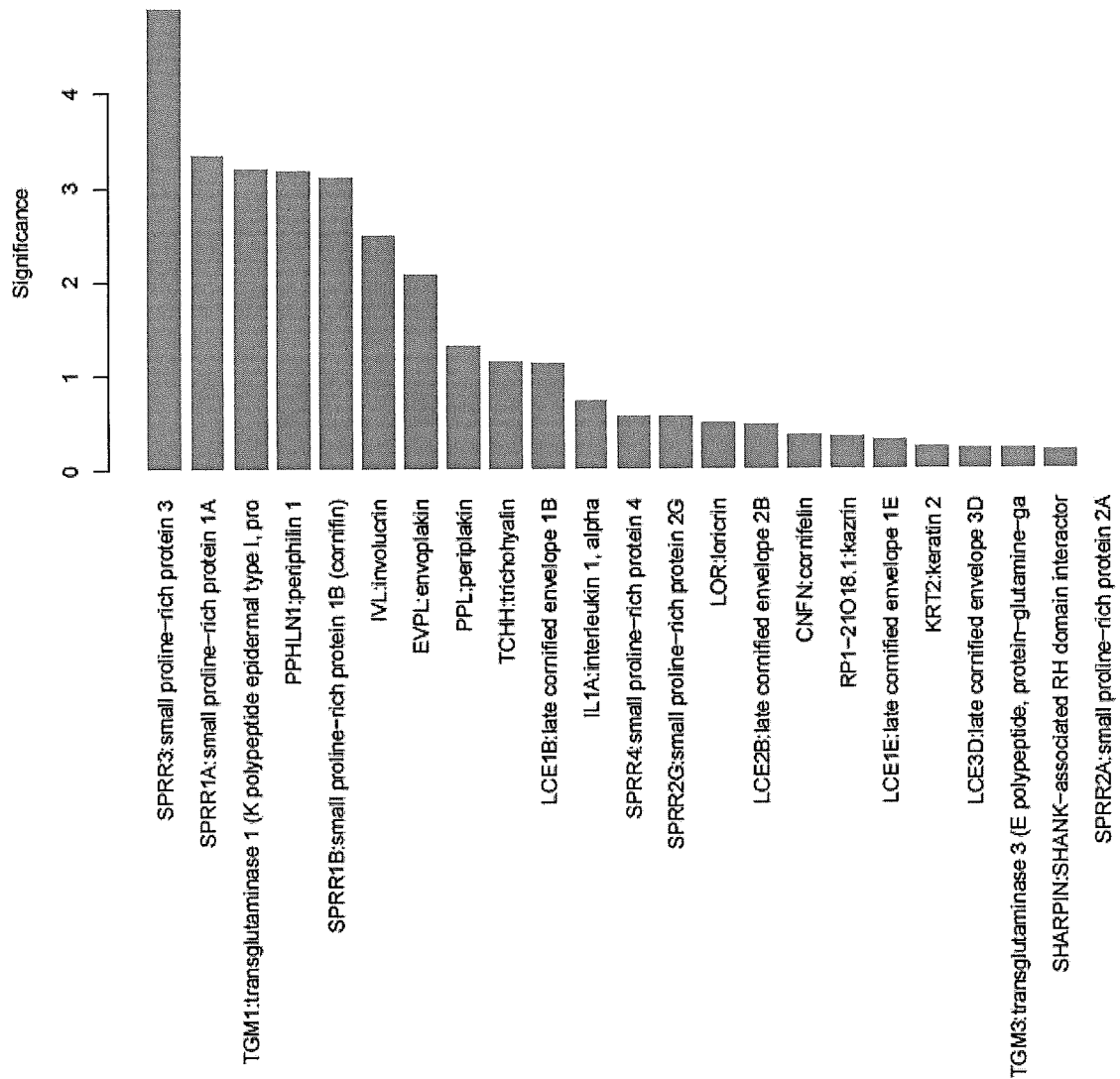
Figure 15D:
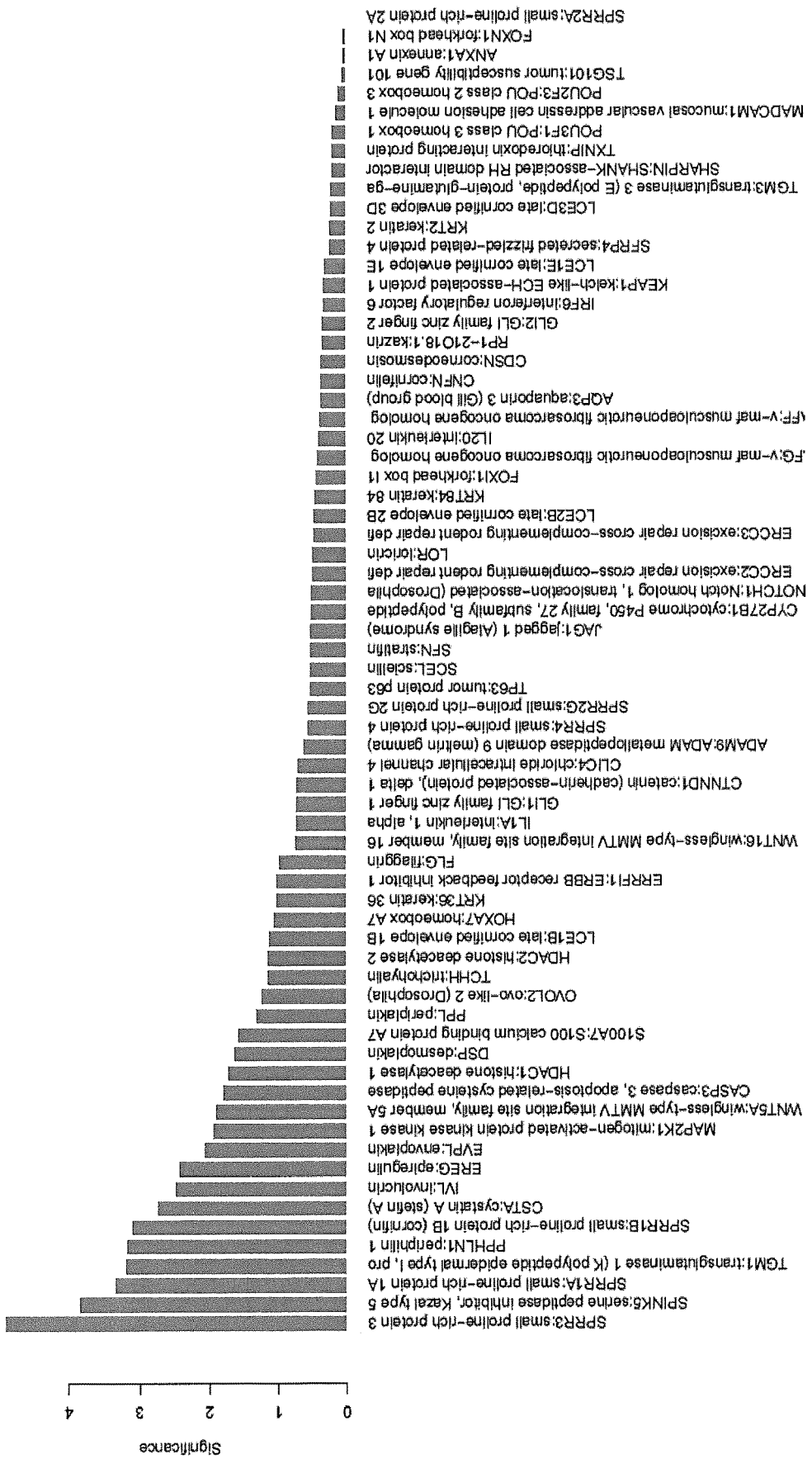
Figure 15E:
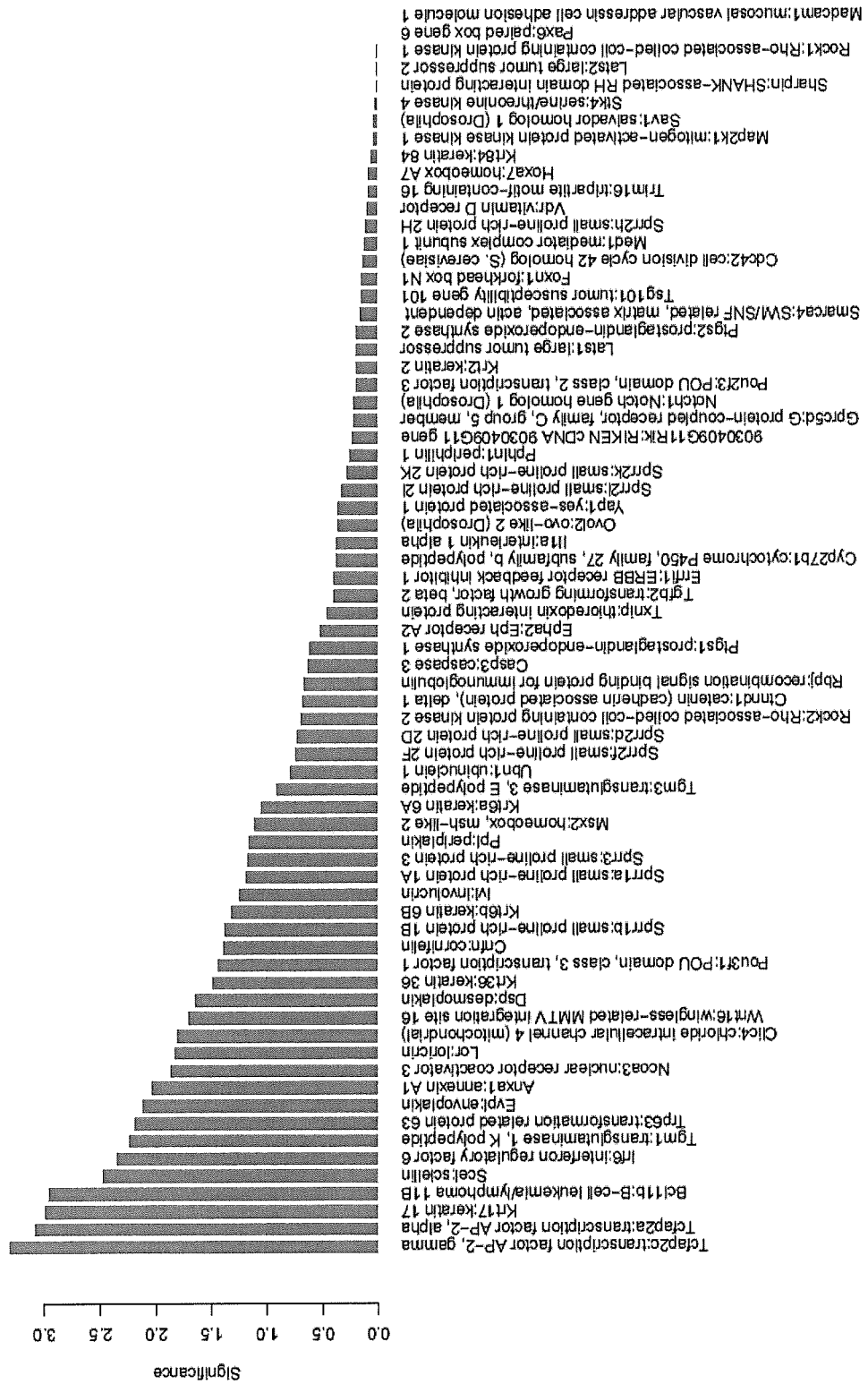
Figure 15F:
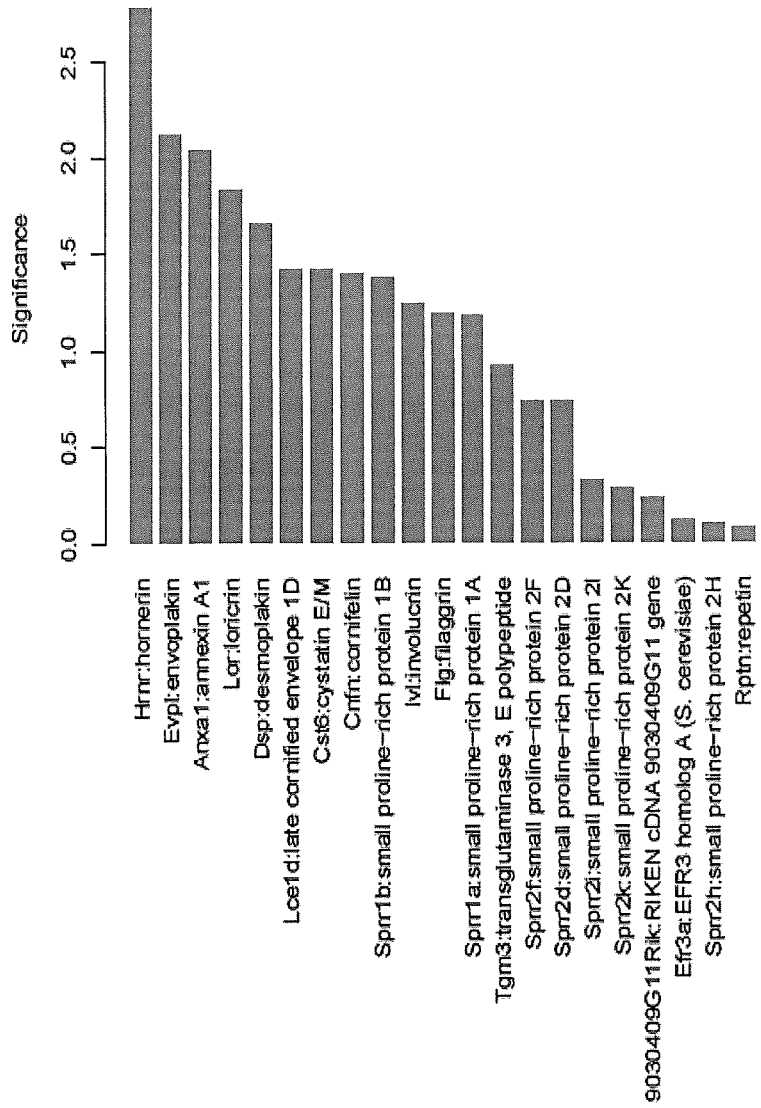
Figure 15G:
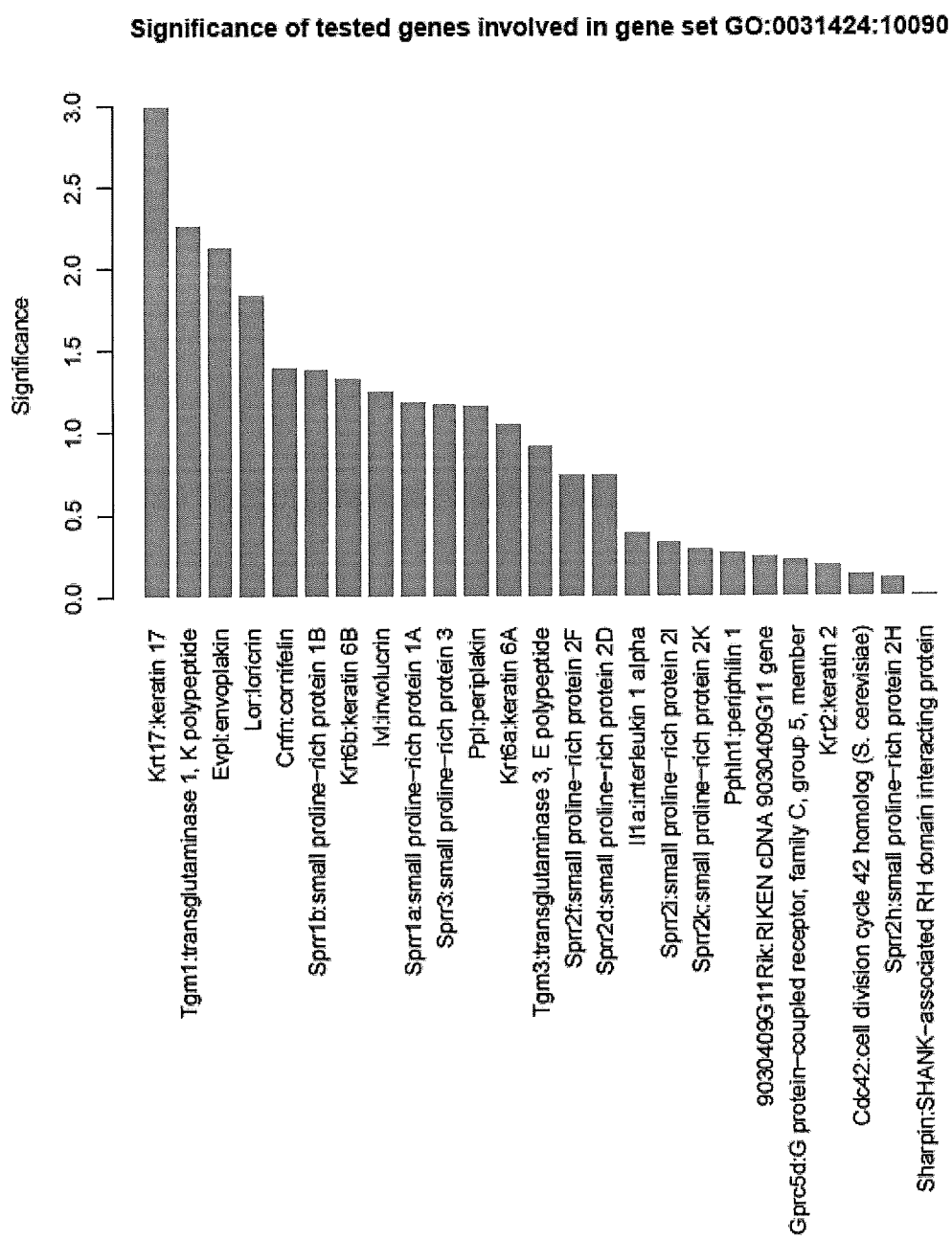
Figure 15H:
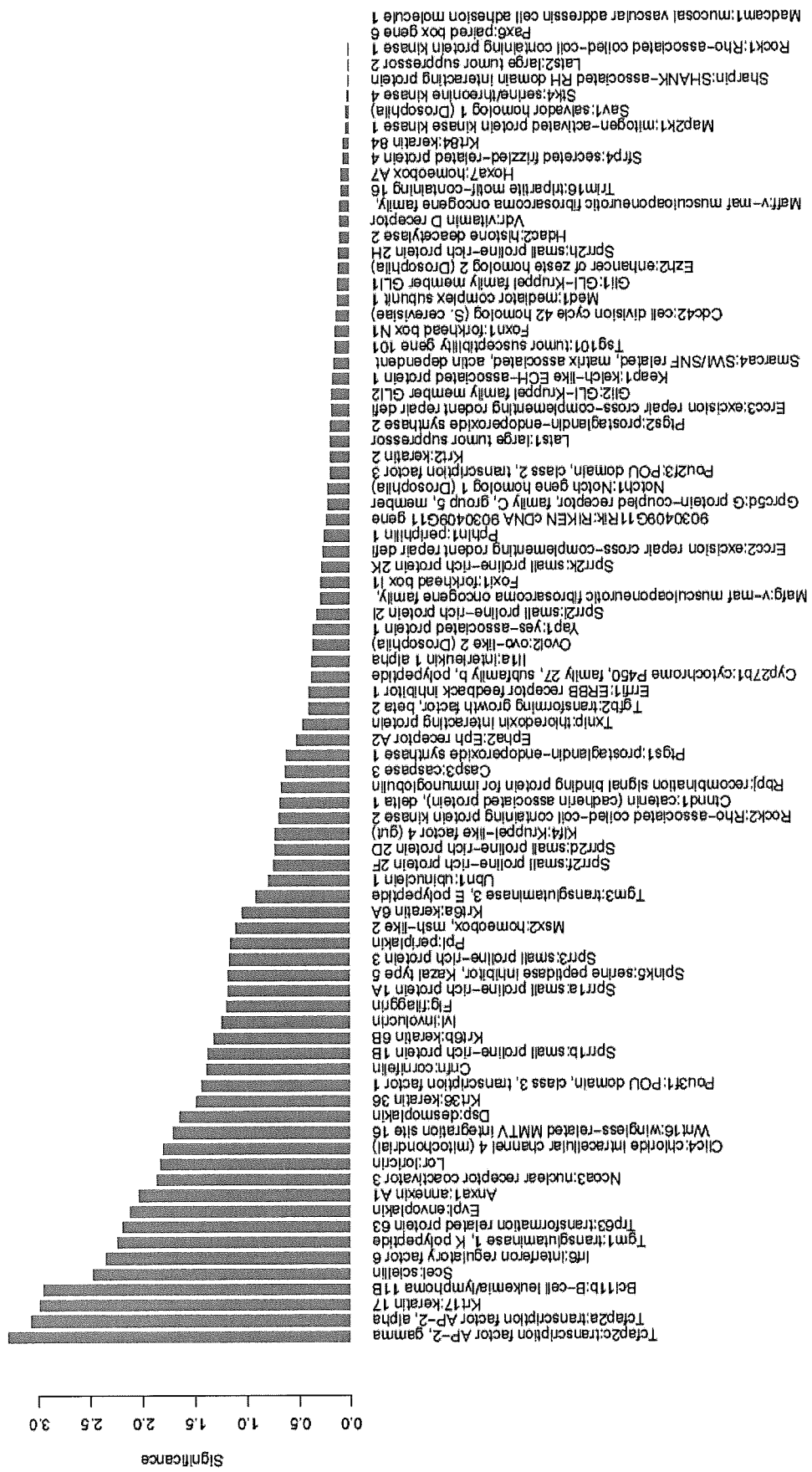
Figure 15I:
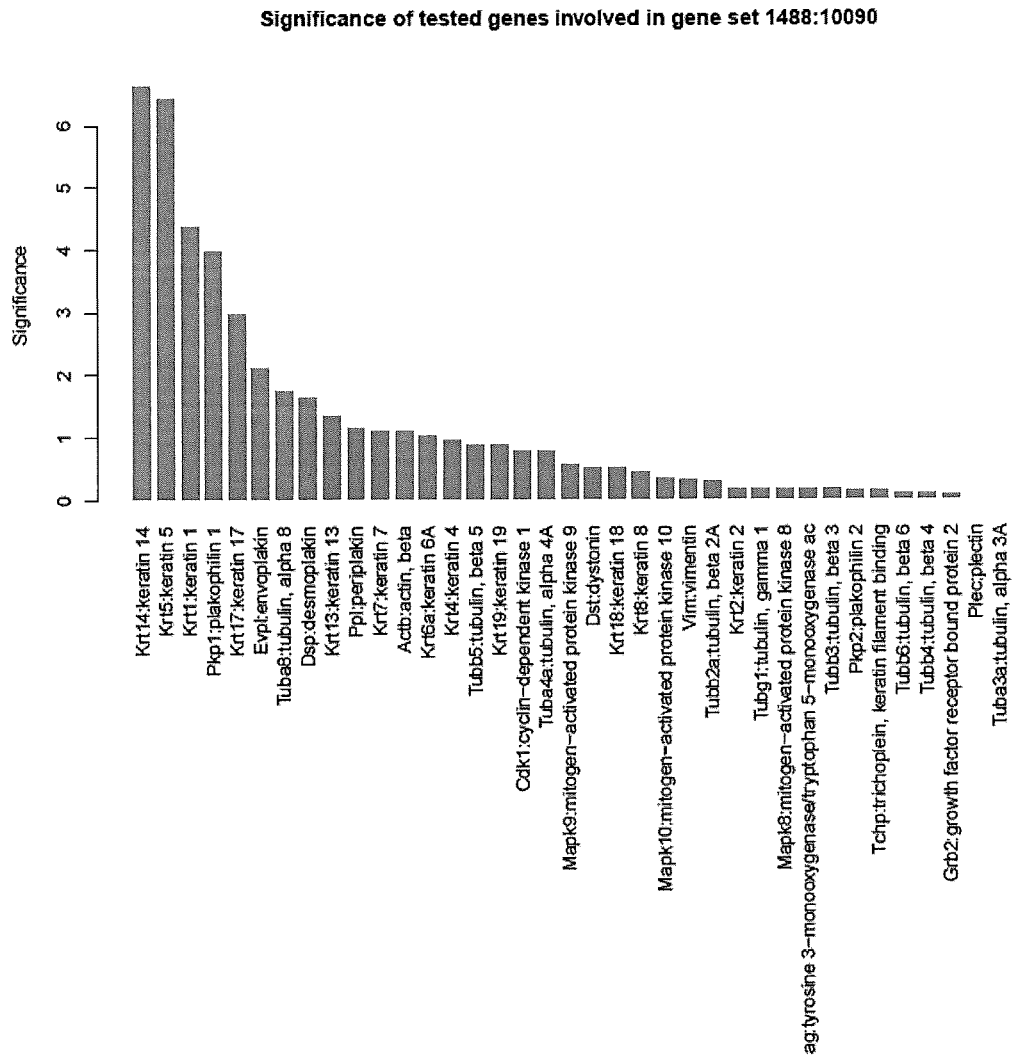
Figure 15J:
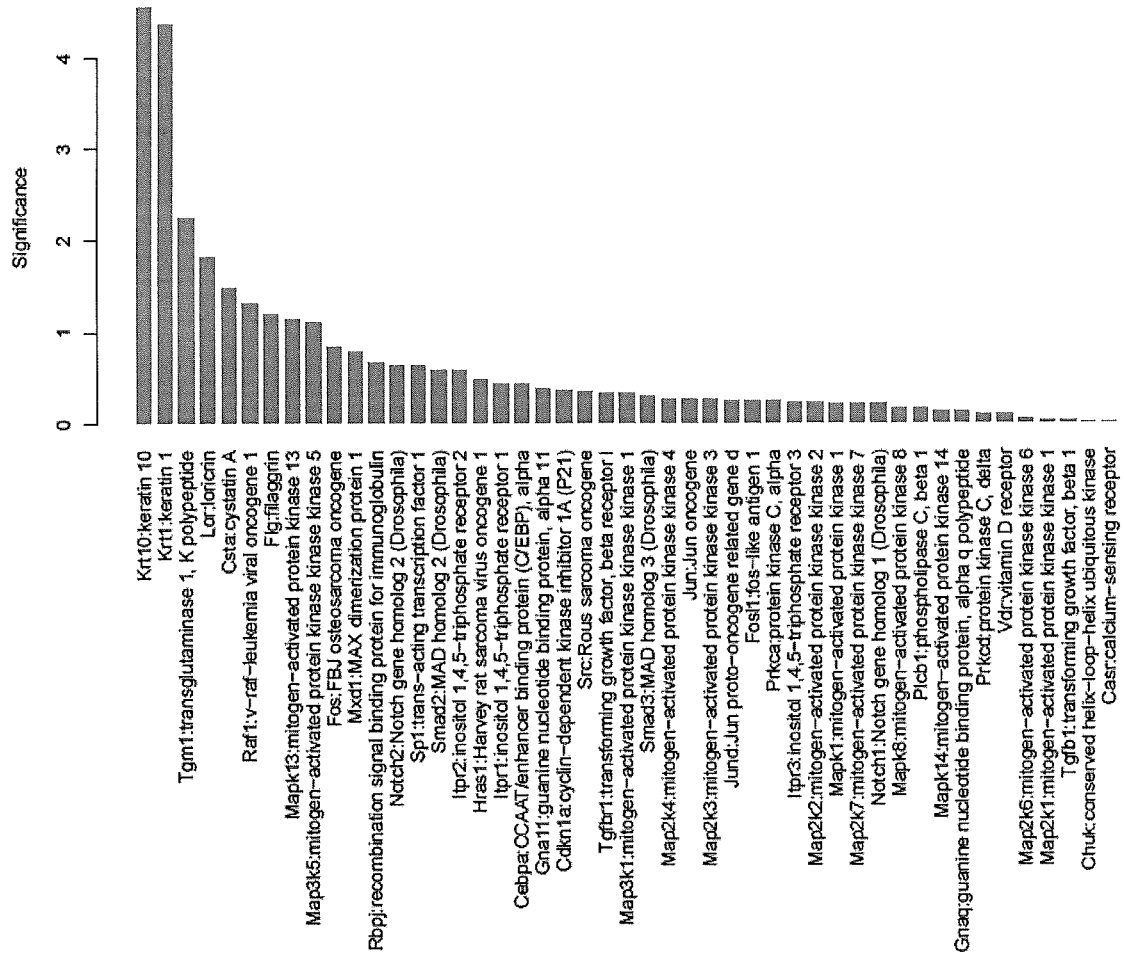
Figure 16A:
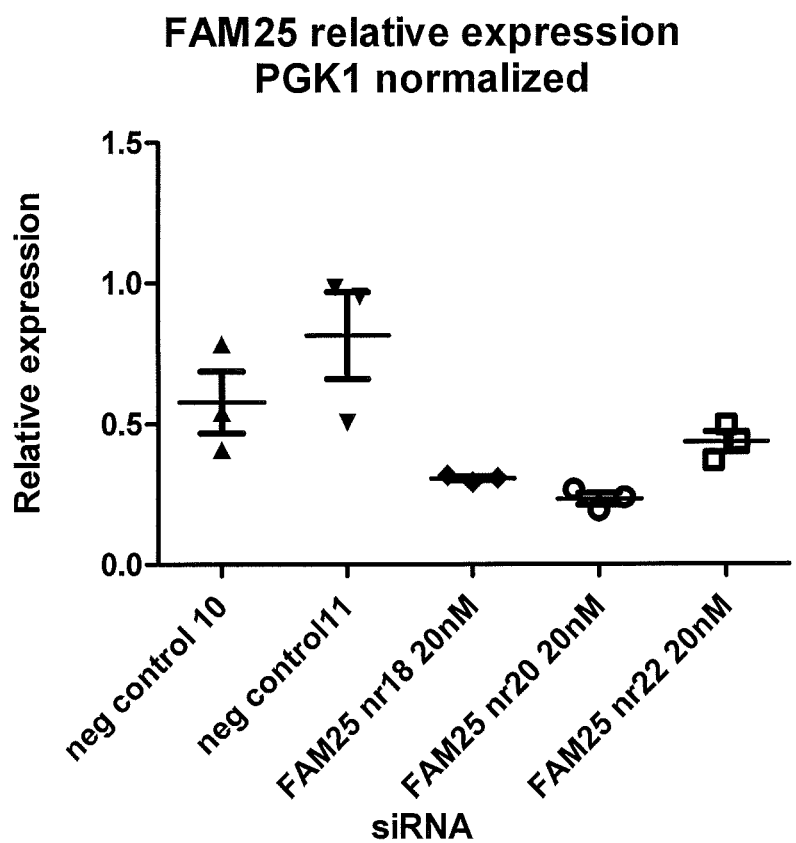
FIGS. 16A-16C: siRNA's against the human $R2R^1$ and $R2R^2$ homologues. The human $R2R^1$ homologue(s) comprise the FAM25 family encompassing the seven human paralogues designated FAM25A, FAM25B, FAM25C, FAM25D, FAM25E, FAM25G and FAM25HP. These are the human homologues of mouse the murine sequence encoded by the cDNA sequences designated 2200001I15Rik or RIKEN cDNA 2200001115. The similarity of the FAM25 paralogues precludes specific RTqPCR of the different paralogues. The FAM25 paralogues are also absent on Affymetrix Human Gene expression arrays such as HT HG-U133 or HT HG-U219. We have selected the RTqPCR primer-probe set Hs04194072 ml (Applied Biosystems) for the measurement of differential gene expression of the FAM25 family. Applied Biosystems states that this primer-probe set doesn't differentiate between the different paralogues. Three siR-NA's designed against the FAM25 family were selected on their ability to downregulate Hs04194072_m1 expression in PBEC's. We have numbered the siRNA's nr 18, 20 and 22 respectively.
Figure 16B:
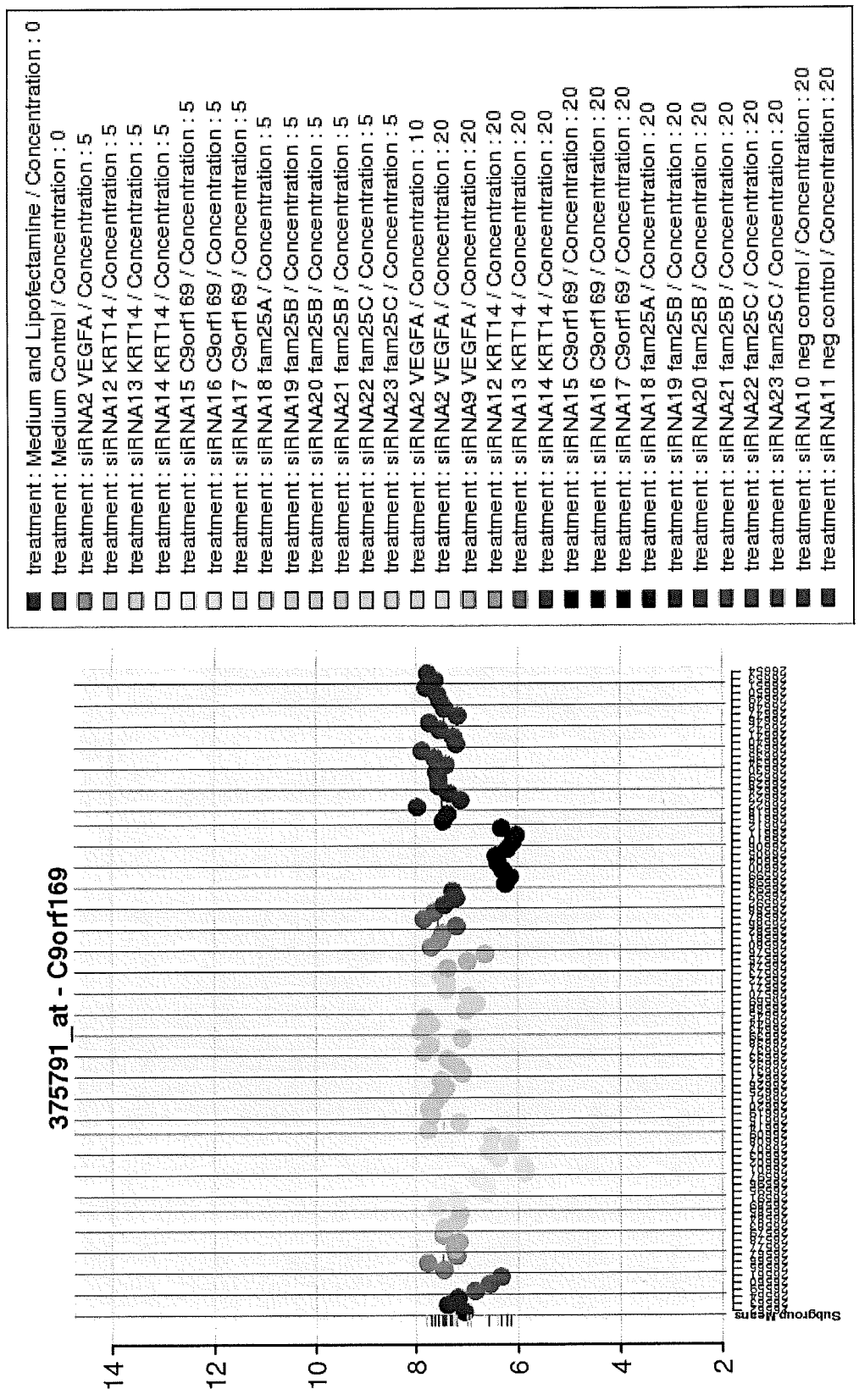
Figure 16C:
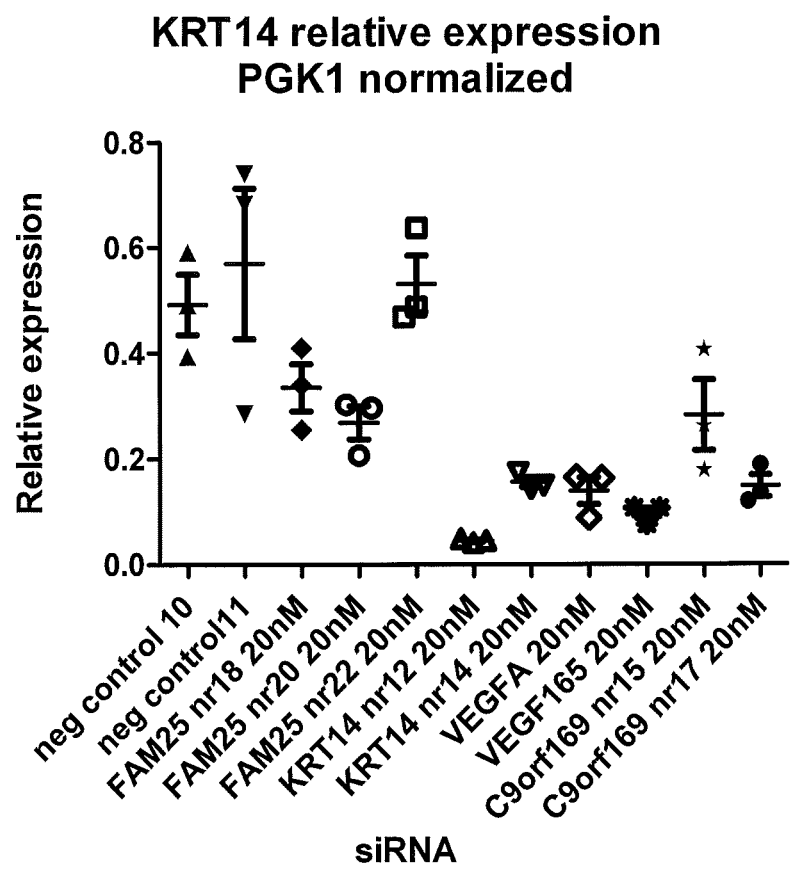
Figure 17:
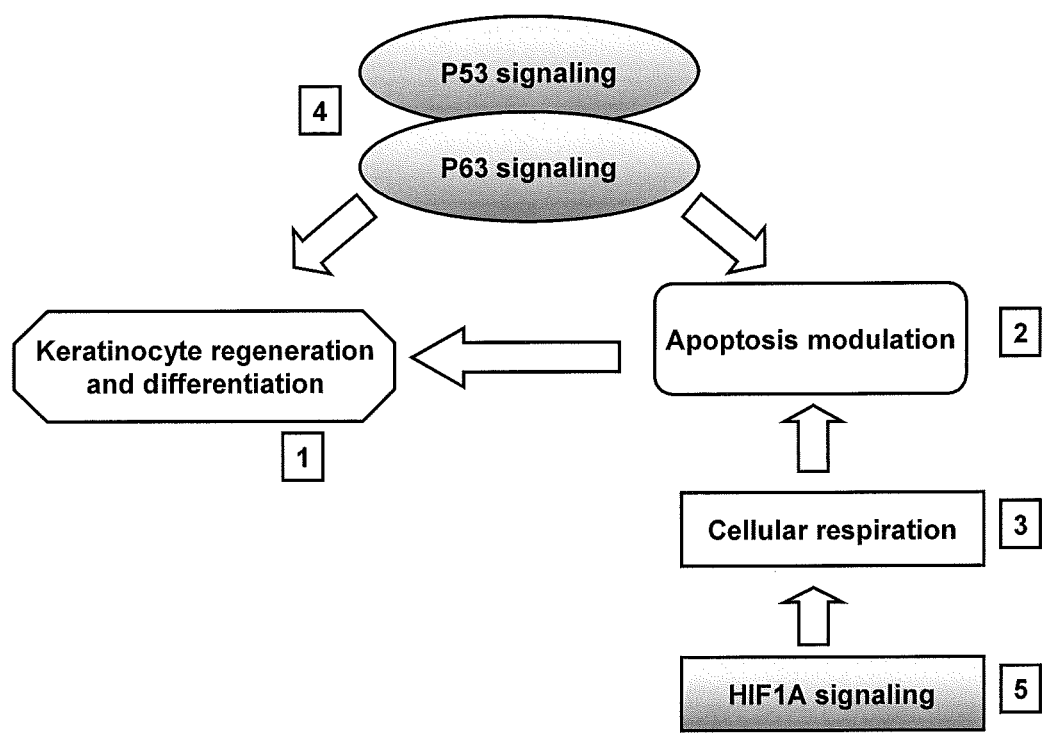
FIG. 17: is a schematic representation of the effects of the R2R homologues. Expression R2R homologues leads to simultaneous modulation of HIF1A signaling (conferring oxygen tolerance) (Box 5), AND modulation of a specific (PERP) anti-apoptotic pathway (Box 4). This will permit the (re)generation of strong epithelial cells (with a major defense barrier against stress), without the installment of unlimited growth potential. In other words, the modulation of a specific anti-apoptotic pathway is not a 'permit' for general tolerance to apoptosis. General tolerance to apoptosis would lead to the dangerous situation of immortalization of the cell: the cell develops into a cancer cell. The pathway was constructed on the basis of microarray analysis of siRNA mediated knockdown of the human $R2R^1$ homologue (FAM25 family) and human $R2R^2$ homologue (C9orf169).
Figure 18A:
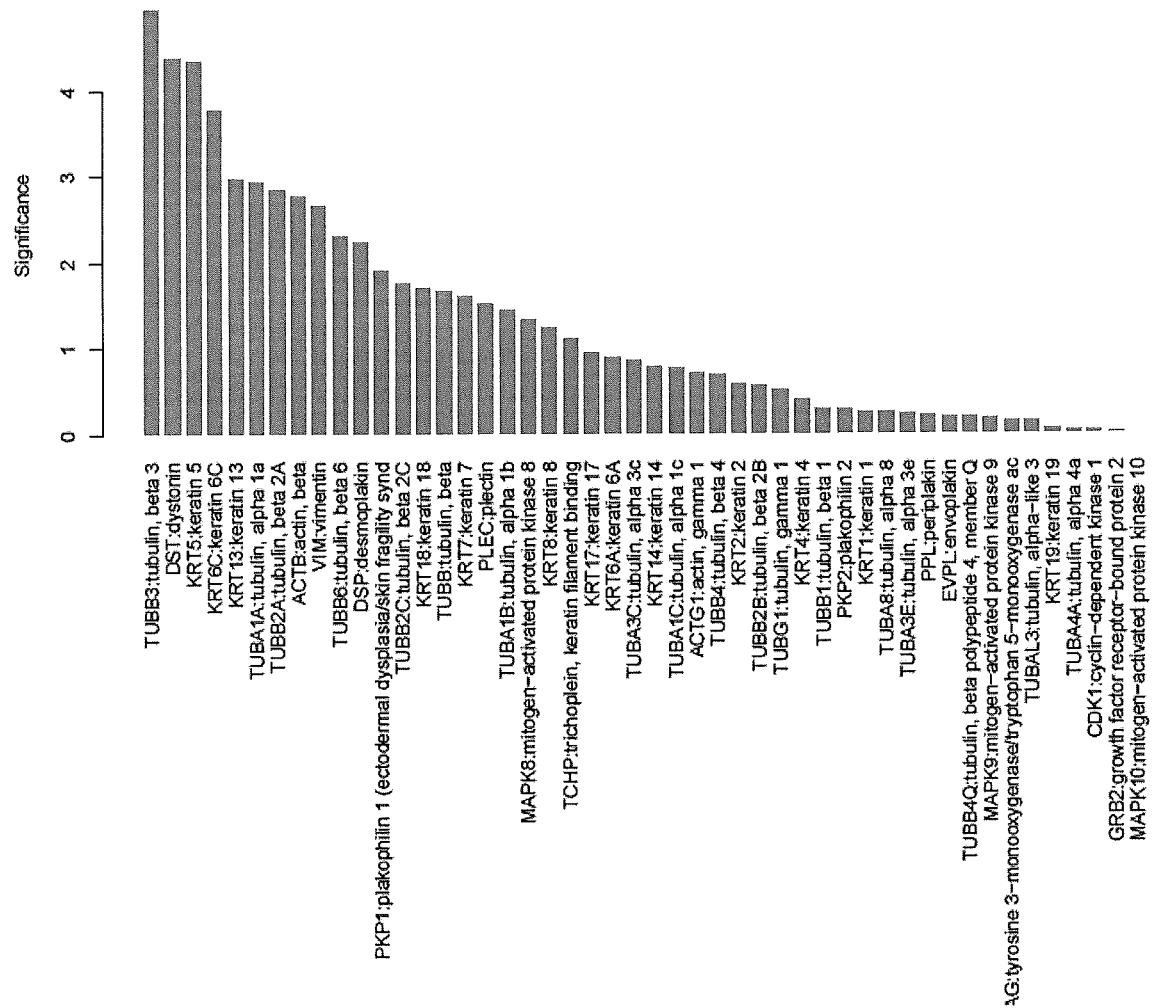
FIGS. 18A-18C: The R2R homologues are essential for 'Keratinocyte regeneration and differentiation'(Box 1) and 'Apoptosis modulation'(Box 2) in the VEGFA—$VEGF^{165}$ pathway. The effects on gene expression by the R2R homologues on 'Keratinocyte regeneration and differentiation' (Box 1) are apparent in FIGS. 18A and 18B. The effects on gene expression by the R2R homologues on 'Apoptosis modulation'(Box 2) are apparent in FIG. 18C. They are the final end-effects of Box 3, 4 and 5.
Figure 18B:
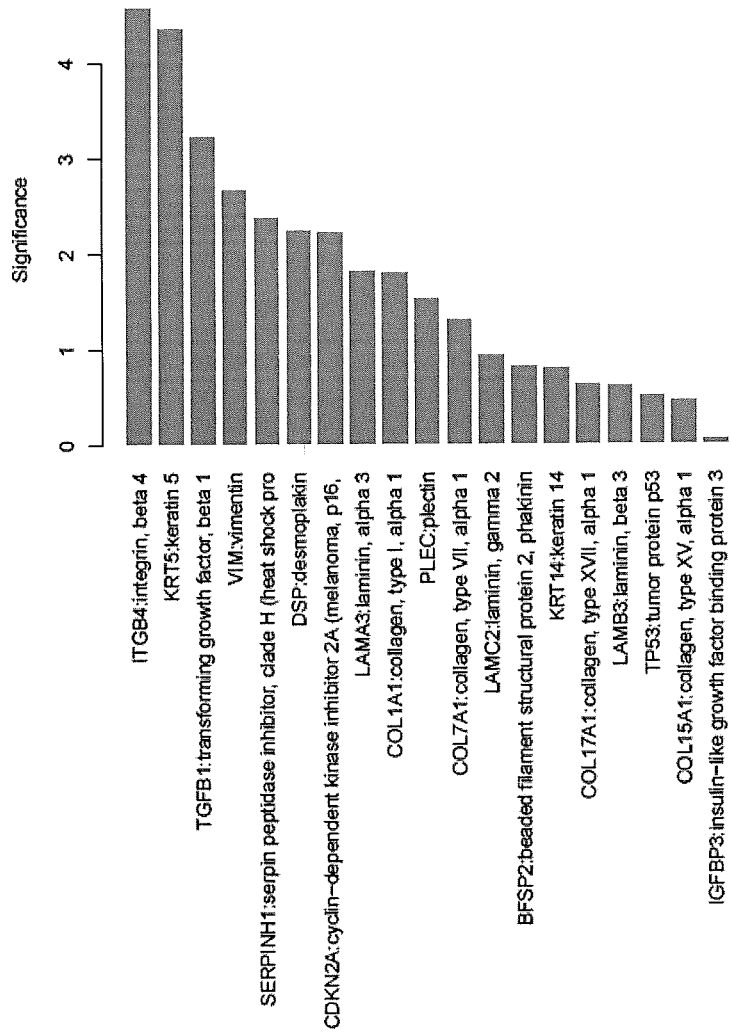
Figure 18C:
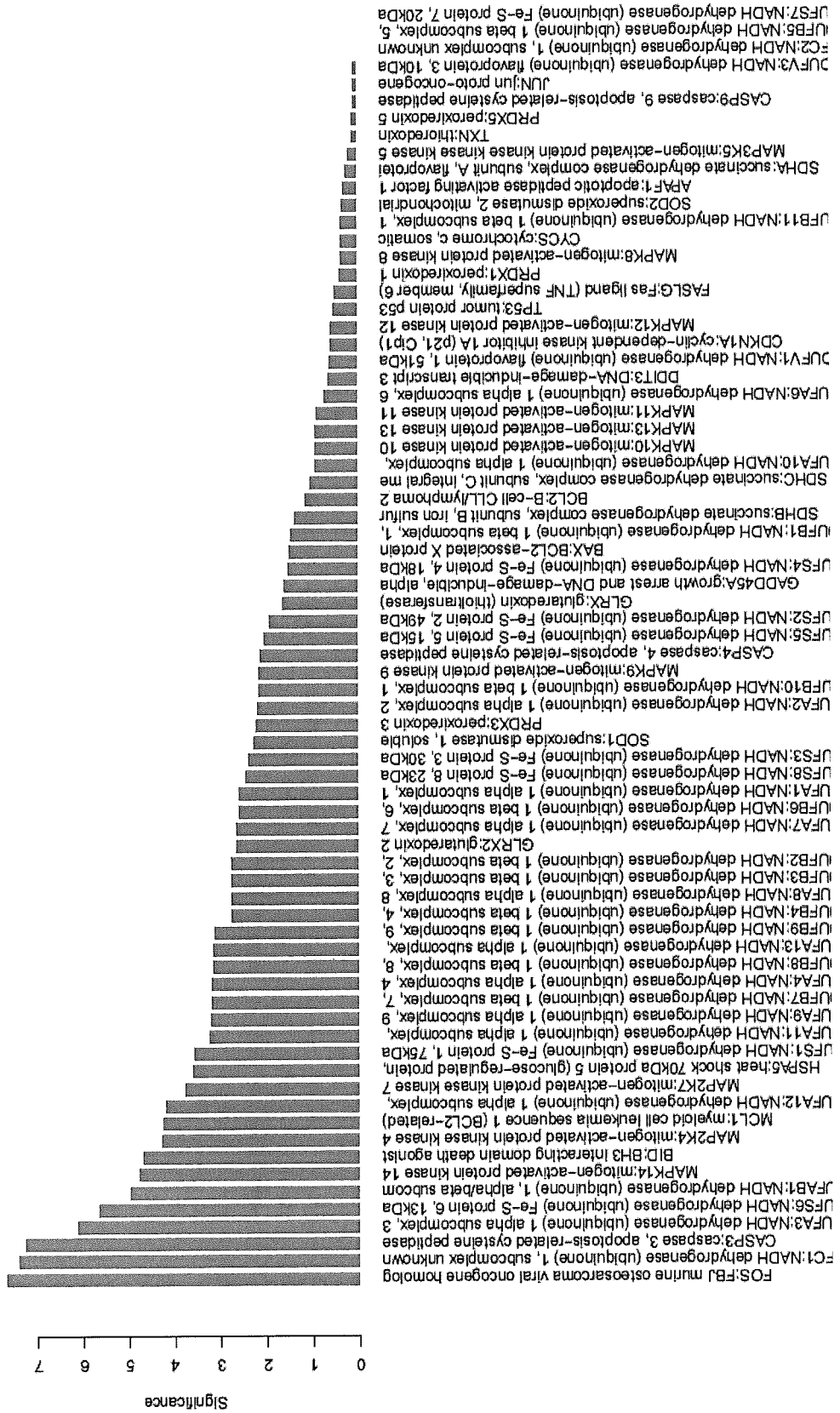
Figure 19A:
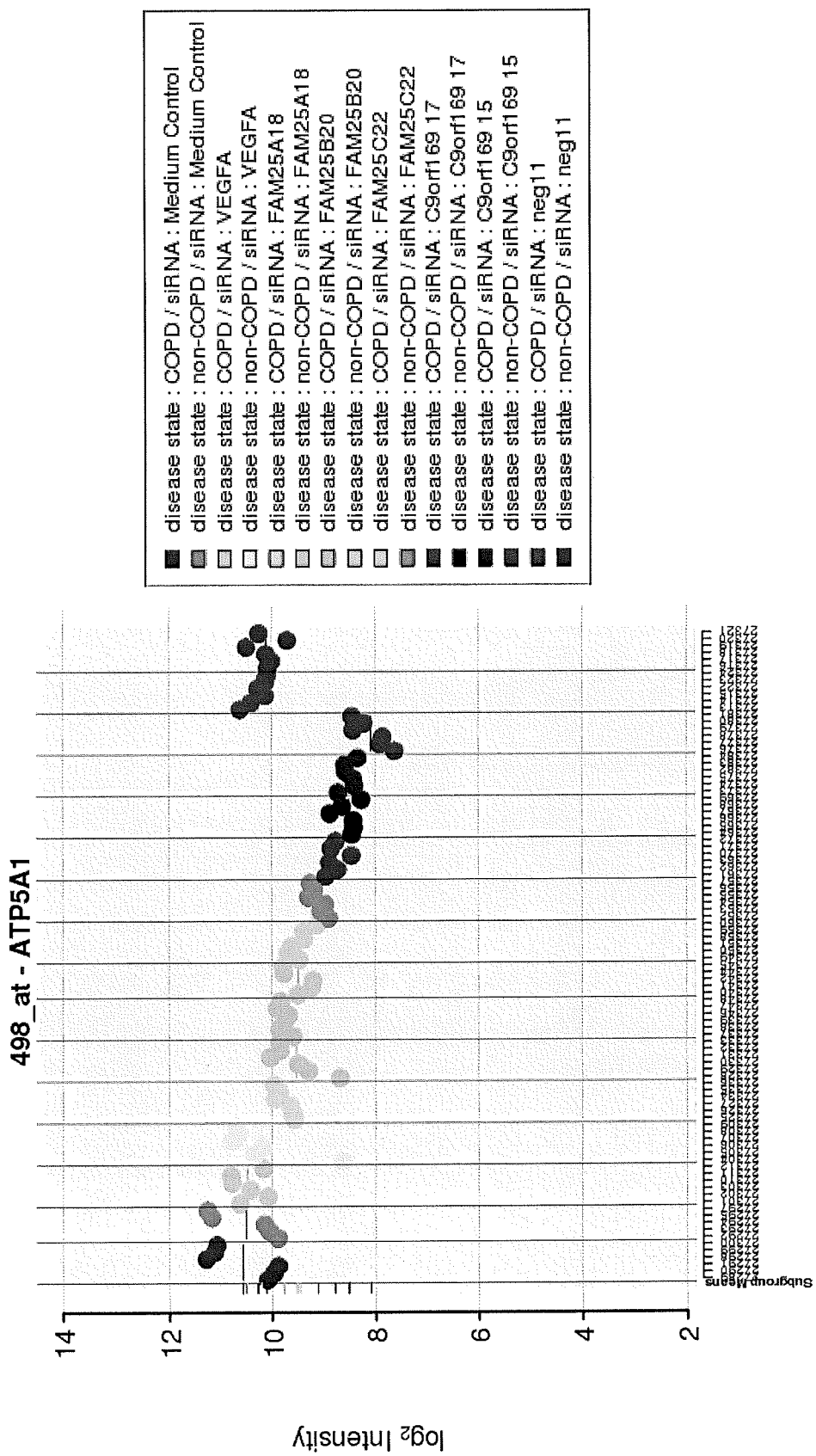
FIGS. 19A and 19B: The effect on cellular respiration (see Box 3 in FIG. 17) is highly specific: siRNA mediated knockdown of the R2R homologues will downregulate oxidative phosphorylation. Expression of the R2R homologues will upregulate oxidative phosphorylation. We can observe this effect at it's most profound in the expression of mitochondrial ATP5A1—ATP synthase (H+ transporting) (FIG. 19A). siRNA's directed at the R2R homologues will downregulate ATP5A1 expression.
Figure 19B:
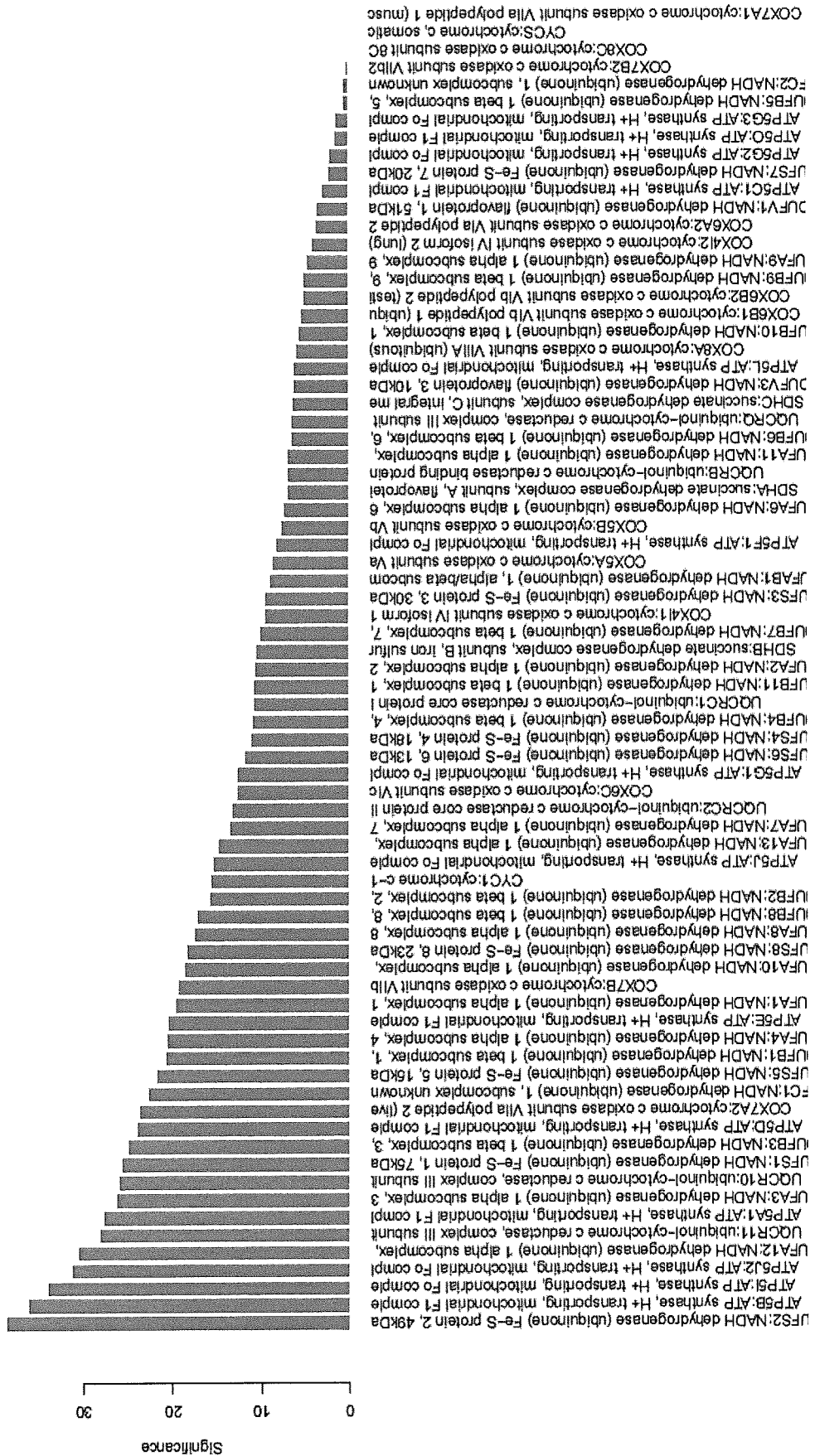
Figure 20:
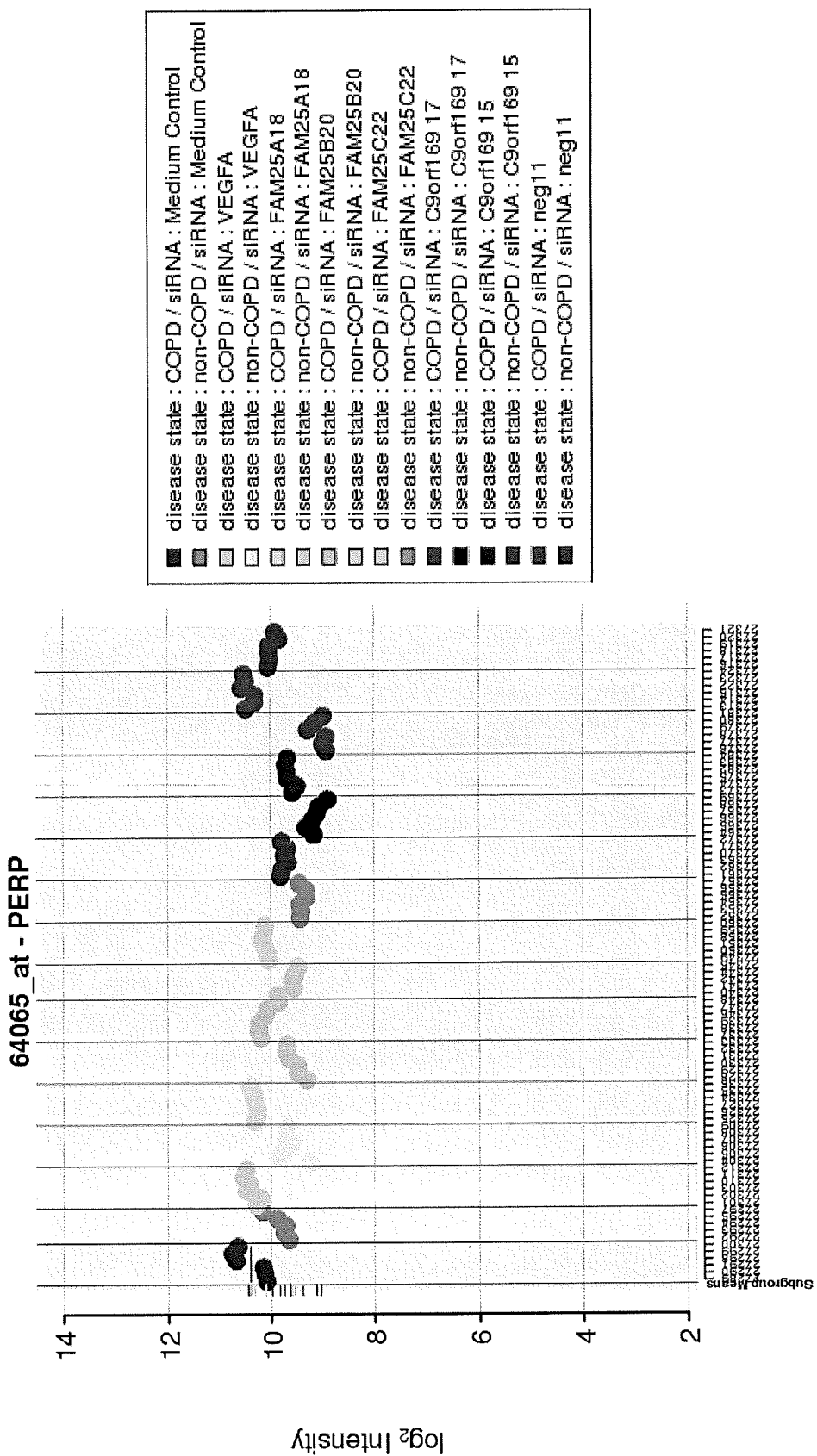
FIG. 20: The effects of the R2R homologues on P53—P63 signaling (see Box 4 in FIG. 17). PERP (TP53 apoptosis effector) is downregulated by siRNA mediated knockdown of the human R2R homologues. 'PERP is a p63-Regulated Gene Essential for Epithelial Integrity. p63 is a master regulator of stratified epithelial development that is both necessary and sufficient for specifying this multifaceted program. Perp, a tetraspan membrane protein originally identified as an apoptosis-associated target of the p53 tumor suppressor, is the first direct target of p63 clearly involved in mediating this developmental program in vivo': this was demonstrated by Rebecca A. Ihrie et al. in 2005 (Cell, Vol. 120, 843-856, Mar. 25, 2005) (italics quoting author in the abstract of the paper). The graph demonstrates the downregulation of PERP expression after siRNA mediated knockdown of the human R2R homologues.
Figure 21:
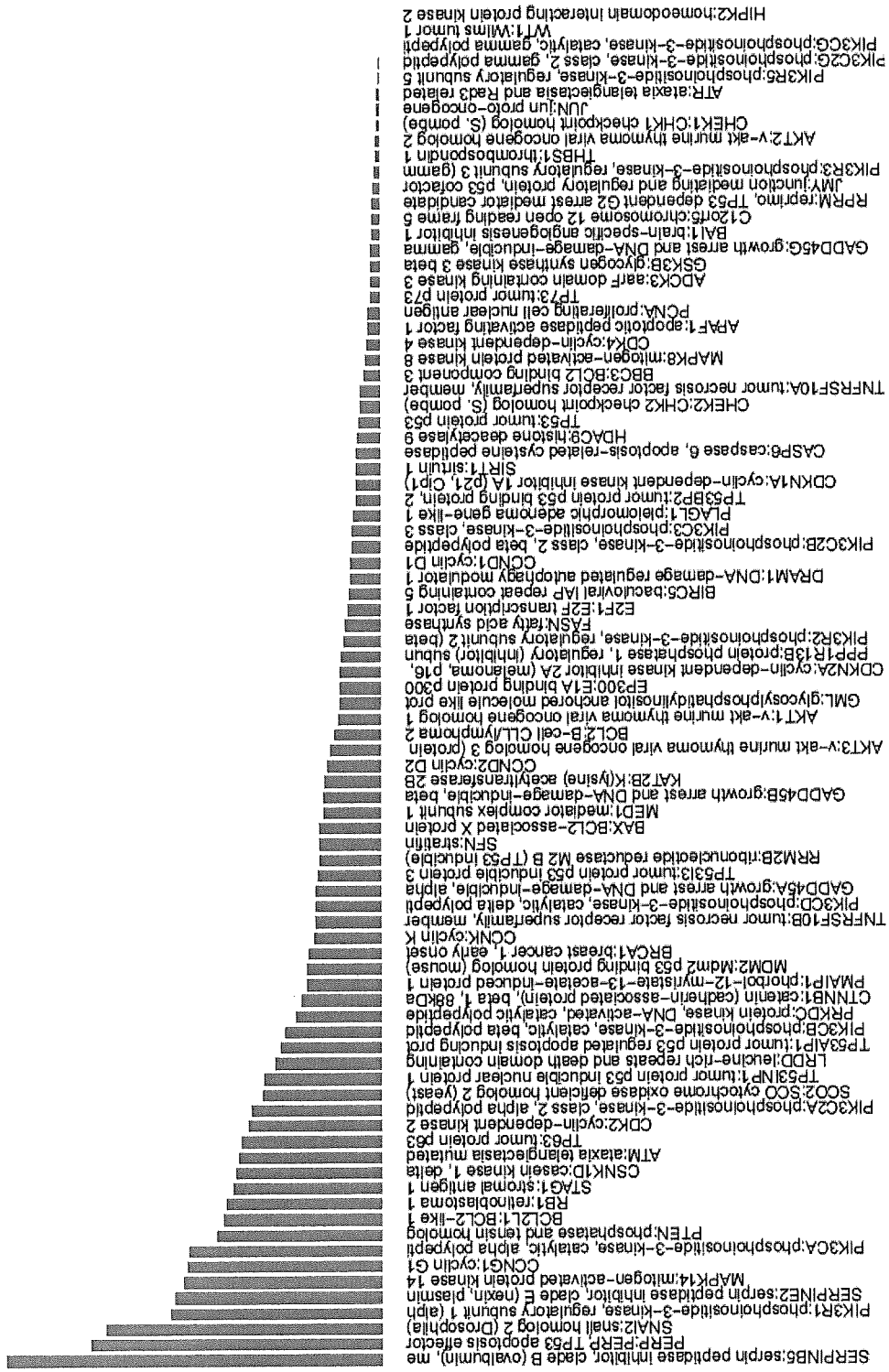
FIG. 21: An overview of the expression of PERP among global changes in gene expression of the P53 pathway after administration of FAM25 nr 20 (directed at human homologue R2R[1])
Figure 22:
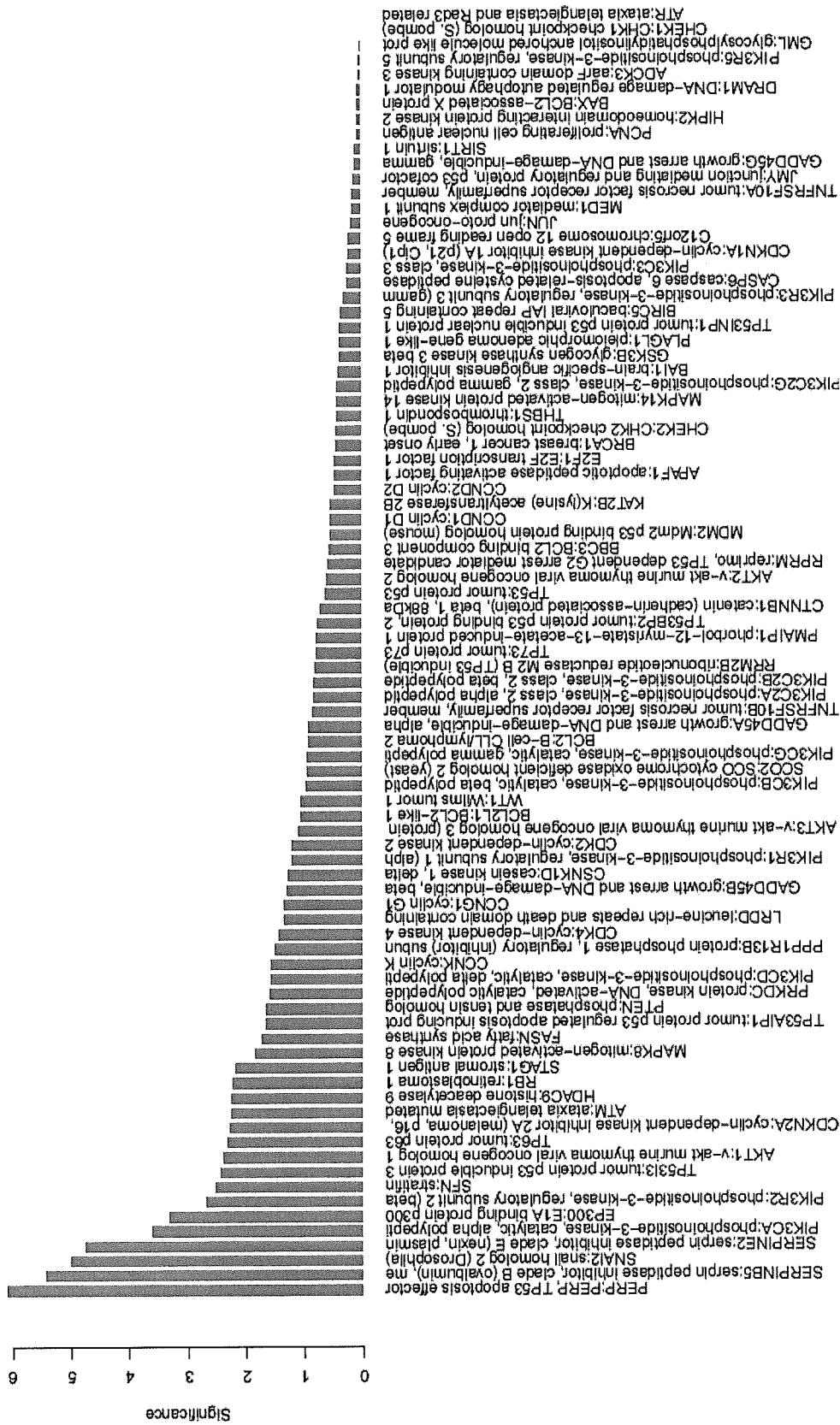
FIG. 22: An overview of the expression of PERP among global changes in gene expression of the P53 pathway after administration of FAM25 nr 18 (directed at human homologue R2R[1])
Figure 23:
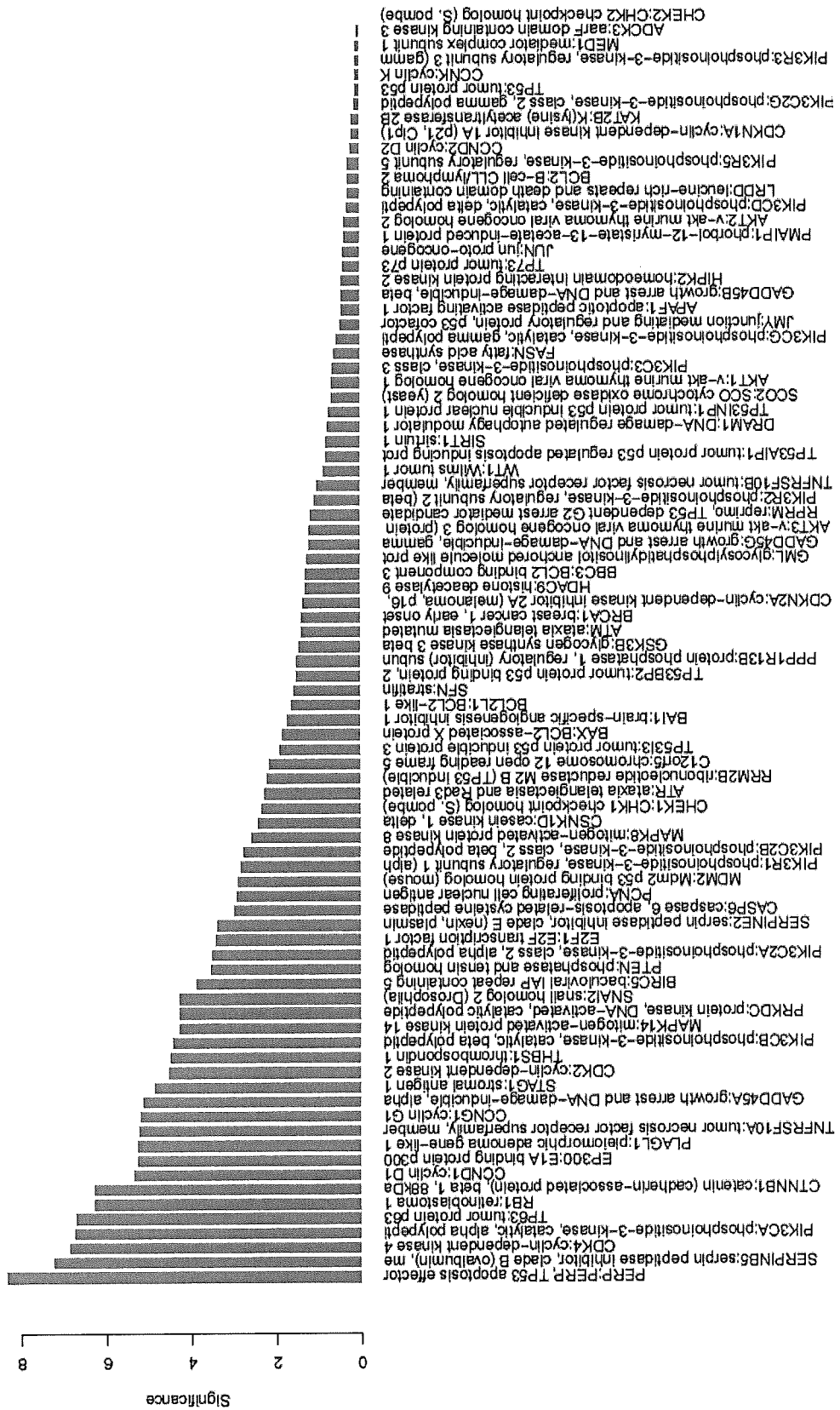
FIG. 23: An overview of the expression of PERP among global changes in gene expression of the P53 pathway after administration of C9orf169 nr 15 (directed at human homologue R2R[2])
Figure 24:
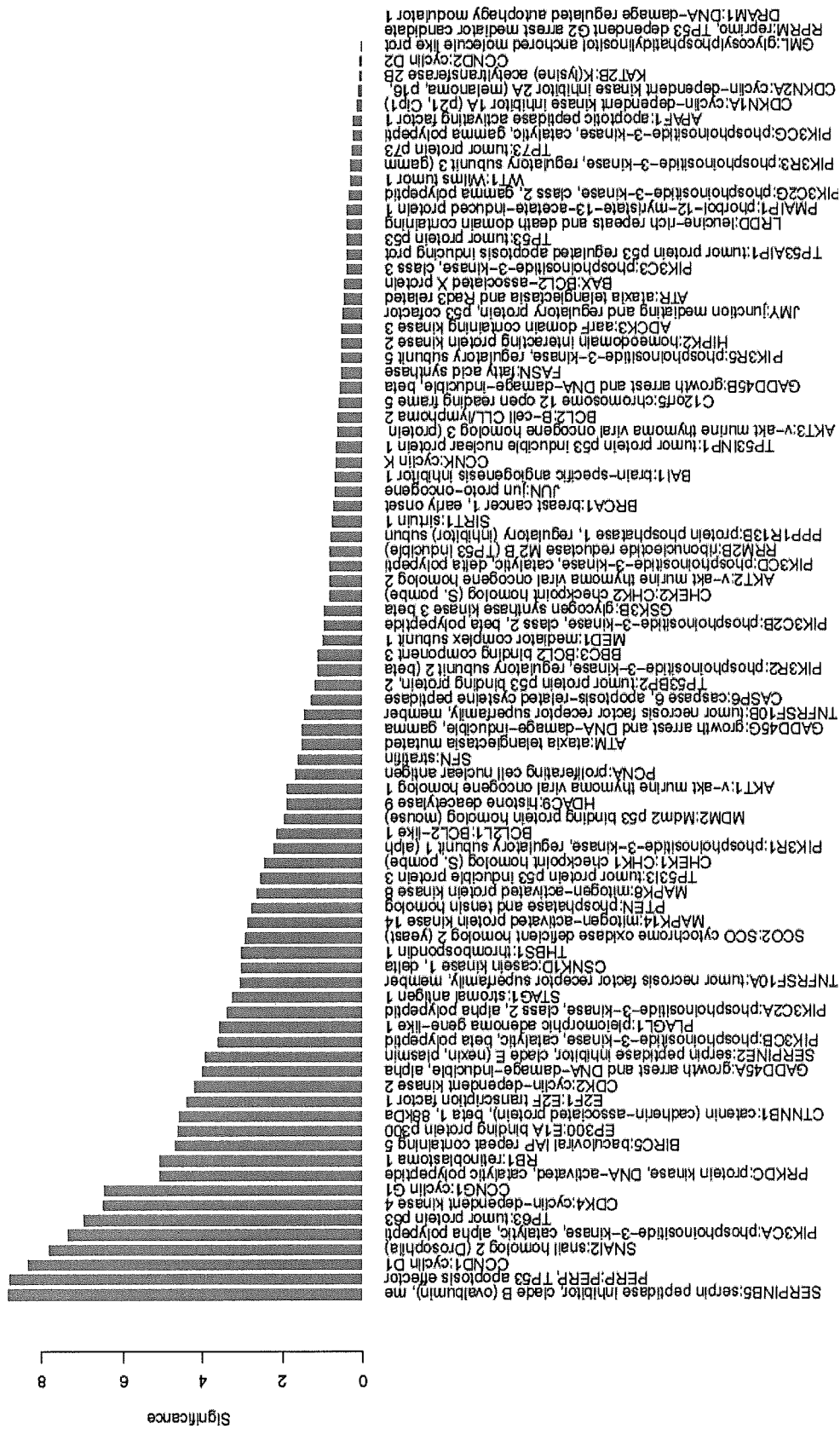
FIG. 24: An overview of the expression of PERP among global changes in gene expression of the P53 pathway after administration of C9orf169 nr 17 (directed at human homologue R2R[2])

$R2R^2$ $R2R^2$ has been found to be very highly expressed in adult human primary lung epithelial cells. In vitro, the expression of $R2R^1$ has been found to be upregulated over time and to be VEGF-A (isoform VEGF$^{165}$) dependent. The $R2R^2$ protein product is important for normal differentiation and maintenance of the adult pulmonary epithelium (see FIG. 13).

The invention claimed is:

1. A method of identifying or obtaining agents which modulate the expression of a gene sequence encoding a protein having the sequence of SEQ ID NO: 3, SEQ ID NO: 6, SEQ ID NO: 9 or SEQ ID NO: 12, said method comprising the steps of:
contacting a cell endogenously expressing said gene sequence with a test agent; and
detecting any modulation of the expression of the gene sequence encoding the protein having the sequence of SEQ ID NO: 3, SEQ ID NO: 6, SEQ ID NO: 9 or SEQ ID NO: 12 when compared to a non-contacted control cell, wherein a difference in expression levels indicates the agent modulates the expression of the gene sequence encoding the protein having the sequence of SEQ ID NO:3, SEQ ID NO:6, SEQ ID NO:9 or SEQ ID NO:12.

2. The method of claim 1, further comprising comparing results with those results obtained from a control method in which the cell has not been contacted with a test agent.

3. The method of claim 2, wherein if the level of said protein is less or greater than the level of expression of said protein detected in the control method, the test agent may be useful as a modulator of the expression of said gene sequence.

4. The method of claim 1, wherein the test agents is selected from the group consisting of nucleic acids, antisense oligonucleotides, proteins, peptides, amino acids, antibodies, carbohydrates and small organic molecules.

5. The method of claim 1, wherein the cell endogenously expressing said gene sequence is a primary bronchial epithelial cell (PBEC).

6. The method of claim 1, wherein said contacting is carried out in vitro.

7. The method of claim 1, wherein said contacting is carried out in vivo.

8. The method of claim 1, wherein the detecting comprises detecting a level of the protein having the sequence of SEQ ID NO: 3, SEQ ID NO: 6, SEQ ID NO: 9 or SEQ ID NO: 12.

* * * * *

UNITED STATES PATENT AND TRADEMARK OFFICE
CERTIFICATE OF CORRECTION

PATENT NO. : 10,975,441 B2  
APPLICATION NO. : 15/383085  
DATED : April 13, 2021  
INVENTOR(S) : Aerssens et al.

Page 1 of 1

It is certified that error appears in the above-identified patent and that said Letters Patent is hereby corrected as shown below:

On the Title Page

Item (30) Foreign Application Priority Data: Please correct "1250127" to read -- 11250127.5 --

In the Specification

Column 2, Line 43: Please correct "2200001115Rik" to read -- 2200001I15Rik --

Column 2, Line 44: Please correct "2200001115" to read -- 2200001I15 --

Column 22, Line 27: Please correct "2200001115" to read -- 2200001I15 --

Column 22, Line 32: Please correct "2200001115" to read -- 2200001I15 --

Column 29, Line 11: Please correct "121413" to read -- I21413 --

Column 34, Line 9: Please correct "i/+ cells" to read -- il+ cells --

Column 34, Line 14: Please correct "2200001115" to read -- 2200001I15 --

Column 34, Line 25: Please correct "2200001115" to read -- 2200001I15 --

Column 34, Line 30: Please correct "2200001115" to read -- 2200001I15 --

Column 34, Line 33: Please correct "2200001115" to read -- 2200001I15 --

In the Claims

Column 47, Line 4, Claim 4: Please correct "agents is" to read -- agent is --

Signed and Sealed this  
Third Day of August, 2021

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 12

<210> SEQ ID NO 1
<211> LENGTH: 425
<212> TYPE: DNA
<213> ORGANISM: Mus musculus

<400> SEQUENCE: 1

| | | | | | |
|---|---|---|---|---|---|
| acactgacac | ggaccgaagg | agtggaaaaa | gctttacctg | tcactgtctg | ctgccatacg | 60 |
| atgctgggag | gcctggggaa | gctggcggcc | gagggcctgg | cccaccgcac | agagaaagcc | 120 |
| actggggag | cagttcacgc | agtggaagag | gtggtgagcg | aggtggtggg | ccacgccaag | 180 |
| gaggttggag | agaagaccat | taatgacgcc | ctaaagaaag | cccaagaatc | aggagacagg | 240 |
| gtggtgaagg | aggtcactga | aaggtcacc | cacaccatca | ctgatgctgt | tacccatgcg | 300 |
| gcagaaggcc | tgggaagact | gggacagtga | gcctgcctac | cagcatggct | ggcccttcct | 360 |
| gaaggtcaat | aaagagtgtg | aaacgtgaaa | aaaaaaaaa | aaataacaaa | aaaaaaaaaa | 420 |
| aaaaa | | | | | | 425 |

<210> SEQ ID NO 2
<211> LENGTH: 267
<212> TYPE: DNA
<213> ORGANISM: Mus musculus

<400> SEQUENCE: 2

| | | | | | |
|---|---|---|---|---|---|
| atgctgggag | gcctggggaa | gctggcggcc | gagggcctgg | cccaccgcac | agagaaagcc | 60 |
| actggggag | cagttcacgc | agtggaagag | gtggtgagcg | aggtggtggg | ccacgccaag | 120 |
| gaggttggag | agaagaccat | taatgacgcc | ctaaagaaag | cccaagaatc | aggagacagg | 180 |
| gtggtgaagg | aggtcactga | aaggtcacc | cacaccatca | ctgatgctgt | tacccatgcg | 240 |
| gcagaaggcc | tgggaagact | gggacag | | | | 267 |

<210> SEQ ID NO 3
<211> LENGTH: 89
<212> TYPE: PRT
<213> ORGANISM: Mus musculus

<400> SEQUENCE: 3

Met Leu Gly Gly Leu Gly Lys Leu Ala Ala Glu Gly Leu Ala His Arg
1               5                   10                  15

Thr Glu Lys Ala Thr Gly Gly Ala Val His Ala Val Glu Glu Val Val
            20                  25                  30

Ser Glu Val Val Gly His Ala Lys Glu Val Gly Glu Lys Thr Ile Asn
        35                  40                  45

Asp Ala Leu Lys Lys Ala Gln Glu Ser Gly Asp Arg Val Val Lys Glu
    50                  55                  60

Val Thr Glu Lys Val Thr His Thr Ile Thr Asp Ala Val Thr His Ala
65                  70                  75                  80

Ala Glu Gly Leu Gly Arg Leu Gly Gln
                85

<210> SEQ ID NO 4
<211> LENGTH: 342
<212> TYPE: DNA
<213> ORGANISM: Homo sapiens

<400> SEQUENCE: 4

| | | | | | |
|---|---|---|---|---|---|
| actgtctgct | gccacacgat | gctggagggc | ctggggaagc | tggctgccga | aggcctggcc | 60 | caccgcaccg agaaggccac cgagggagcc attcatgccg tggaagaagt ggtgaaggag    120 gtggtgggac acgccaagga gactggagag aaagccattg ctgaagccat aaagaaagcc    180 caagagtcag gggacaaaaa gatgaaggaa atcactgaga cagtgaccaa cacagtcaca    240 aatgccatca cccatgcagc agagagtctg gacaaacttg gacagtgagt gcacctgcta    300 ccacggccct tccccagtct caataaaaag ccatgacatg tg    342

```
<210> SEQ ID NO 5
<211> LENGTH: 267
<212> TYPE: DNA
<213> ORGANISM: Homo sapiens
```

<400> SEQUENCE: 5
atgctgggag gcctggggaa gctggctgcc gaaggcctgg cccaccgcac cgagaaggcc     60
accgagggag ccattcatgc cgtggaagaa gtggtgaagg aggtggtggg acacgccaag    120
gagactggag agaaagccat tgctgaagcc ataaagaaag cccaagagtc aggggacaaa    180
aagatgaagg aaatcactga cagtgacc aacacagtca caaatgccat cacccatgca    240
gcagagagtc tggacaaact tggacag    267

```
<210> SEQ ID NO 6
<211> LENGTH: 89
<212> TYPE: PRT
<213> ORGANISM: Homo sapiens
```

<400> SEQUENCE: 6

Met Leu Gly Gly Leu Gly Lys Leu Ala Ala Glu Gly Leu Ala His Arg
1               5                   10                  15

Thr Glu Lys Ala Thr Glu Gly Ala Ile His Ala Val Glu Glu Val Val
            20                  25                  30

Lys Glu Val Val Gly His Ala Lys Glu Thr Gly Glu Lys Ala Ile Ala
        35                  40                  45

Glu Ala Ile Lys Lys Ala Gln Glu Ser Gly Asp Lys Lys Met Lys Glu
    50                  55                  60

Ile Thr Glu Thr Val Thr Asn Thr Val Thr Asn Ala Ile Thr His Ala
65                  70                  75                  80

Ala Glu Ser Leu Asp Lys Leu Gly Gln
                85

```
<210> SEQ ID NO 7
<211> LENGTH: 1078
<212> TYPE: DNA
<213> ORGANISM: Mus musculus
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (887)..(888)
<223> OTHER INFORMATION: n is a, c, g, or t
<220> FEATURE:
<221> NAME/KEY: misc_feature
<222> LOCATION: (893)..(893)
<223> OTHER INFORMATION: n is a, c, g, or t
<220> FEATURE:
<221> NAME/KEY: misc_feature
<222> LOCATION: (900)..(900)

<223> OTHER INFORMATION: n is a, c, g, or t

<400> SEQUENCE: 7

```
gtgactggct gctgtctcta gttgttgagg cctcttggga tctyggcgct macmccwtgc      60
tytagwgact ccgatagctc ccrmggctcc agtgsasmcc tcggkcggng gnagggaaaa     120
ggcacttgct ggtagctctg ctcacccgca ctgggacctg gagctggagg actaagaaga    180
cagacggctg ctgcttgcca cagcctggac catggacccc catgagatgg ttgtgaagaa    240
tccatatgcc cacatcagca ttcctcgggc tcacctgcgc tctgacctgg ggcagcagtt    300
agaggaggtt ccttcttcat cttcctcctc tgagactcag cctctgcctg caggaacatg    360
tatcccagag ccagtgggcc tcttacaaac tactgaagcc cctgggccca aggtatcaa    420
gggcatcaag gtactgctc ctgagcacgg ccagcagacc tggcagtcac cctgcaatcc    480
ctatagcagt gggcaacgtc catcgggact gacttatgct ggcctgccac ctgtagggcg    540
tggtgatgac attgcccacc actgctgctg ctgcccttgc tgctcctgct gccactgtcc    600
tcgcttctgc cgttgtcaca gctgttgtgt tatctcctag ctgactattg aacctccagg    660
gctgtgcagc ccaggttcct gctcaatgcc aaagtgttgc tggacatcag gagcagccgt    720
tgtcatgagc atcagccatt tcctgccctg agcaggggag cctgtccacc agcgttcagc    780
tgtagccttc tggaataggg ttccagccac tagccatgtt ggcaacaaca gggacaccct    840
tcacgtcctg caagactttg gcaataaagc aggatgagcg ttgctgnncc tgntgaaaan    900
aaamwaaawa cwgccgttgt cacarcygtt rtgttatctm mkagstgacw attgtaammt    960
ycagrgctgt rmagcccrgg kksckgctca atgccaaagt gttgmtgsmc mtcrggrgsr   1020
gccaagcttt acgcggtacc cgggattttt tttgtacaaa aaggggcccc ctattagg     1078
```

<210> SEQ ID NO 8
<211> LENGTH: 426
<212> TYPE: DNA
<213> ORGANISM: Mus musculus

<400> SEQUENCE: 8

```
atggaccccc atgagatggt tgtgaagaat ccatatgccc acatcagcat tcctcgggct     60
cacctgcgct ctgacctggg gcagcagtta gaggaggttc cttcttcatc ttcctcctct    120
gagactcagc ctctgcctgc aggaacatgt atcccagagc cagtgggcct cttacaaact    180
actgaagccc ctgggcccaa ggtatcaagg gcatcaagg gtactgctcc tgagcacggc    240
cagcagacct ggcagtcacc ctgcaatccc tatagcagtg ggcaacgtcc atcgggactg    300
acttatgctg gcctgccacc tgtagggcgt ggtgatgaca ttgcccacca ctgctgctgc    360
tgcccttgct gctcctgctg ccactgtcct cgcttctgcc gttgtcacag ctgttgtgtt    420
atctcc                                                                426
```

<210> SEQ ID NO 9
<211> LENGTH: 142
<212> TYPE: PRT
<213> ORGANISM: Mus musculus

<400> SEQUENCE: 9

```
Met Asp Pro His Glu Met Val Val Lys Asn Pro Tyr Ala His Ile Ser
1               5                   10                  15

Ile Pro Arg Ala His Leu Arg Ser Asp Leu Gly Gln Gln Leu Glu Glu
            20                  25                  30

Val Pro Ser Ser Ser Ser Ser Ser Glu Thr Gln Pro Leu Pro Ala Gly
```

```
             35                  40                  45
Thr Cys Ile Pro Glu Pro Val Gly Leu Leu Gln Thr Thr Glu Ala Pro
         50                  55                  60

Gly Pro Lys Gly Ile Lys Gly Ile Lys Gly Thr Ala Pro Glu His Gly
 65                  70                  75                  80

Gln Gln Thr Trp Gln Ser Pro Cys Asn Pro Tyr Ser Ser Gly Gln Arg
                 85                  90                  95

Pro Ser Gly Leu Thr Tyr Ala Gly Leu Pro Pro Val Gly Arg Gly Asp
            100                 105                 110

Asp Ile Ala His His Cys Cys Cys Cys Pro Cys Cys Ser Cys Cys His
            115                 120                 125

Cys Pro Arg Phe Cys Arg Cys His Ser Cys Cys Val Ile Ser
            130                 135                 140

<210> SEQ ID NO 10
<211> LENGTH: 1291
<212> TYPE: DNA
<213> ORGANISM: Homo sapiens

<400> SEQUENCE: 10
```

| | | | | |
|---|---|---|---|---|
| cttgaacccg ggaggcagag gttgcagtga gccgagatcg cgcagctgca ctccagcctg | 60 |
| ggcaacagag caagactcca tctcagaaaa gaagcagaaa gcctccaaga gccaatggct | 120 |
| ctcaagcatc ttggtctctg ctaagaagag gctcagaggc ttagaagccc tgcctcgccg | 180 |
| gggctttgag gtgtgtgagc aatggctggg gactgcaggc ccgggaatct gagggcctca | 240 |
| ccccacttcc tttccagagc cgtgacctca ggctcacctc ctgccctcct ctcaggcaag | 300 |
| ctgcagatgc cctttagggc ccaggccatg ccccggatgt gaggggctga gtcactggtt | 360 |
| tggcagtgcc cctcagagcc caggcctggg ctgccaccca cctgaggacg agggctgggc | 420 |
| cagctgtcgt gctccagttg ctggggcctc ttgggatctt gggaacccca tctctgagcc | 480 |
| ccgcccatg gccccgcccc tcccaaggag ggaaaaggcg gctgccagtc gctcaactca | 540 |
| ggcactggga cctagagctc agaagaccga gaggacagac tgccgtgttg ccaccacagg | 600 |
| ctggaccatg gacccccaag agatggtcgt caagaaccca tatgcccaca tcagcatccc | 660 |
| ccgggctcac ctgcggcctg acctggggca gcagttagag gtggcttcca cctgttcctc | 720 |
| atcctcggag atgcagcccc tgccagtggg gccctgtgcc ccagagccaa cccacctctt | 780 |
| gcagccgacc gaggtcccag ggcccaaggg cgccaagggt aaccagggg ctgcccccat | 840 |
| ccagaaccag caggcctggc agcagcctgg caaccctac agcagcagtc agcgccaggc | 900 |
| cggactgacc tacgctggcc ctccgcccgc ggggcgcggg gatgacatcg cccaccactg | 960 |
| ctgctgctgc ccctgctgcc actgctgcca ctgccccccc ttctgccgct gccacagctg | 1020 |
| ctgctgctgt gtcatctcct agcccagccc accctgccag ggccaggacc cagacttcag | 1080 |
| caaatgtggc tcacacagtg ccgggacatg ccgggacatg cggggtggct gttgtcatgg | 1140 |
| gcgtctgccc cttcacacca ggcactgggg ctcagaccca ccaggaaggt ggccgttcag | 1200 |
| cccgagctcc tgaaacggaa tcccaggtcc tggctggaga gggacacccc tgattacctt | 1260 |
| aaggcccagg caataaagca gggtgatctt c | 1291 |

```
<210> SEQ ID NO 11
<211> LENGTH: 552
<212> TYPE: DNA
<213> ORGANISM: Homo sapiens

<400> SEQUENCE: 11
```

```
atggccccgc ccctcccaag gagggaaaag gcggctgcca gtcgctcaac tcaggcactg    60
ggacctagag ctcagaagac cgagaggaca gactgccgtg ttgccaccac aggctggacc   120 atggacccc aagagatggt cgtcaagaac ccatatgccc acatcagcat cccccgggct   180
cacctgcggc ctgacctggg gcagcagtta gaggtggctt ccacctgttc ctcatcctcg   240
gagatgcagc ccctgccagt ggggccctgt gccccagagc caacccacct cttgcagccg   300
accgaggtcc cagggcccaa gggcgccaag ggtaaccagg gggctgcccc catccagaac   360
cagcaggcct ggcagcagcc tgcaaccccc tacagcagca gtcagcgcca ggccggactg   420
acctacgctg gccctccgcc cgcggggcgc ggggatgaca tcgcccacca ctgctgctgc   480
tgcccctgct gccactgctg ccactgcccc cccttctgcc gctgccacag ctgctgctgc   540
tgtgtcatct cc                                                        552
```

<210> SEQ ID NO 12
<211> LENGTH: 184
<212> TYPE: PRT
<213> ORGANISM: Homo sapiens

<400> SEQUENCE: 12

```
Met Ala Pro Pro Leu Pro Arg Arg Glu Lys Ala Ala Ser Arg Ser
1               5                   10                  15

Thr Gln Ala Leu Gly Pro Arg Ala Gln Lys Thr Glu Arg Thr Asp Cys
            20                  25                  30

Arg Val Ala Thr Thr Gly Trp Thr Met Asp Pro Gln Glu Met Val Val
        35                  40                  45

Lys Asn Pro Tyr Ala His Ile Ser Ile Pro Arg Ala His Leu Arg Pro
    50                  55                  60

Asp Leu Gly Gln Gln Leu Glu Val Ala Ser Thr Cys Ser Ser Ser Ser
65                  70                  75                  80

Glu Met Gln Pro Leu Pro Val Gly Pro Cys Ala Pro Glu Pro Thr His
                85                  90                  95

Leu Leu Gln Pro Thr Glu Val Pro Gly Pro Lys Gly Ala Lys Gly Asn
            100                 105                 110

Gln Gly Ala Ala Pro Ile Gln Asn Gln Gln Ala Trp Gln Gln Pro Gly
        115                 120                 125

Asn Pro Tyr Ser Ser Ser Gln Arg Gln Ala Gly Leu Thr Tyr Ala Gly
    130                 135                 140

Pro Pro Pro Ala Gly Arg Gly Asp Asp Ile Ala His His Cys Cys Cys
145                 150                 155                 160

Cys Pro Cys Cys His Cys Cys His Cys Pro Pro Phe Cys Arg Cys His
                165                 170                 175

Ser Cys Cys Cys Cys Val Ile Ser
            180
```